United States Patent
Cashman et al.

(10) Patent No.: US 12,173,055 B2
(45) Date of Patent: *Dec. 24, 2024

(54) N-TERMINAL EPITOPES IN AMYLOID BETA AND CONFORMATIONALLY-SELECTIVE ANTIBODIES THERETO

(71) Applicant: The University of British Columbia, Vancouver (CA)

(72) Inventors: Neil R. Cashman, Vancouver (CA); Steven S. Plotkin, Vancouver (CA)

(73) Assignee: The University of British Columbia, Vancouver (CA)

(*) Notice: Subject to any disclaimer, the term of this patent is extended or adjusted under 35 U.S.C. 154(b) by 13 days.

This patent is subject to a terminal disclaimer.

(21) Appl. No.: 17/014,425

(22) Filed: Sep. 8, 2020

(65) Prior Publication Data
US 2021/0154315 A1 May 27, 2021

Related U.S. Application Data

(63) Continuation of application No. 15/774,805, filed as application No. PCT/CA2016/051300 on Nov. 9, 2016, now Pat. No. 10,772,969.

(60) Provisional application No. 62/393,615, filed on Sep. 12, 2016, provisional application No. 62/365,634, filed on Jul. 22, 2016, provisional application No. 62/331,925, filed on May 4, 2016, provisional application No. 62/253,044, filed on Nov. 9, 2015.

(51) Int. Cl.
| | | |
|---|---|---|
| C07K 7/64 | (2006.01) |
| A61K 38/00 | (2006.01) |
| A61K 39/00 | (2006.01) |
| A61K 39/385 | (2006.01) |
| A61K 47/64 | (2017.01) |
| A61K 51/10 | (2006.01) |
| A61P 25/28 | (2006.01) |
| A61P 37/06 | (2006.01) |
| C07K 5/10 | (2006.01) |
| C07K 5/11 | (2006.01) |
| C07K 5/113 | (2006.01) |
| C07K 5/117 | (2006.01) |
| C07K 7/06 | (2006.01) |
| C07K 14/47 | (2006.01) |
| C07K 16/18 | (2006.01) |
| G01N 33/68 | (2006.01) |

(52) U.S. Cl.
CPC .......... *C07K 16/18* (2013.01); *A61K 39/0007* (2013.01); *A61K 39/0008* (2013.01); *A61K 39/385* (2013.01); *A61K 47/643* (2017.08); *A61K 47/646* (2017.08); *A61K 51/10* (2013.01); *A61P 25/28* (2018.01); *A61P 37/06* (2018.01); *C07K 5/10* (2013.01); *C07K 5/1019* (2013.01); *C07K 5/1021* (2013.01); *C07K 5/1024* (2013.01); *C07K 7/06* (2013.01); *C07K 7/64* (2013.01); *C07K 14/4711* (2013.01); *G01N 33/6896* (2013.01); *A61K 38/00* (2013.01); *A61K 2039/6081* (2013.01); *C07K 2317/34* (2013.01); *C07K 2317/76* (2013.01); *G01N 2333/4709* (2013.01)

(58) Field of Classification Search
CPC .............. A61K 47/6803; A61K 47/643; A61K 47/646; A61K 39/0007; A61K 39/385; A61K 2039/6081; A61K 38/00; C07K 5/10; C07K 5/1019; C07K 5/1021; C07K 5/1024; C07K 7/06; C07K 7/64; C07K 14/4711
See application file for complete search history.

(56) References Cited

U.S. PATENT DOCUMENTS

| | | |
|---|---|---|
| 5,283,185 A | 2/1994 | Epand et al. |
| 5,593,846 A | 1/1997 | Schenk et al. |
| 5,770,429 A | 6/1998 | Lonberg et al. |
| 5,814,014 A | 9/1998 | Elsberry et al. |
| 6,043,283 A | 3/2000 | Giulian |
| 6,071,493 A | 6/2000 | Giulian |
| 6,114,598 A | 9/2000 | Kucherlapati et al. |
| 6,150,584 A | 11/2000 | Kucherlapati et al. |
| 6,451,544 B2 | 9/2002 | Giulian |
| 6,475,742 B2 | 11/2002 | Giulian |
| 6,475,745 B1 | 11/2002 | Giulian |
| 6,890,535 B1 | 5/2005 | Schenk |
| 7,012,061 B1 | 3/2006 | Reiss et al. |
| 7,179,892 B2 | 2/2007 | Basi et al. |
| 7,189,819 B2 | 3/2007 | Basi et al. |

(Continued)

FOREIGN PATENT DOCUMENTS

| | | |
|---|---|---|
| CN | 102858796 A | 1/2013 |
| CN | 102869680 A | 1/2013 |

(Continued)

OTHER PUBLICATIONS

Zola, Stuart M. et al. "A Behavioral Task Predicts Conversion to Mild Cognitive Impairment and Alzheimer's Disease." American Journal of Alzheimer's Disease & Other Dementias. 28(2) 179-184 (2012).

(Continued)

*Primary Examiner* — Kimberly Ballard
(74) *Attorney, Agent, or Firm* — SMART & BIGGAR LP; Carmela De Luca

(57) ABSTRACT

The disclosure pertains to N-terminal epitopes identified in A-beta, including conformational epitopes, antibodies thereto and methods of making and using immunogens and antibodies specific thereto.

16 Claims, 29 Drawing Sheets
Specification includes a Sequence Listing.

(56) References Cited

U.S. PATENT DOCUMENTS

| | | | |
|---|---|---|---|
| 7,256,273 B2 | 8/2007 | Basi et al. | |
| 7,288,523 B2 | 10/2007 | Nordstedt et al. | |
| 7,575,880 B1 | 8/2009 | Schenk | |
| 7,582,733 B2 | 9/2009 | Basi et al. | |
| 7,588,766 B1 | 9/2009 | Schenk | |
| 7,625,560 B2 | 12/2009 | Basi et al. | |
| 7,700,751 B2 | 4/2010 | Basi et al. | |
| 7,790,856 B2 | 9/2010 | Schenk | |
| 7,871,615 B2 | 1/2011 | Basi et al. | |
| 7,893,214 B2 | 2/2011 | Schenk | |
| 7,932,048 B2 | 4/2011 | Mendez | |
| 7,964,192 B1 | 6/2011 | Schenk | |
| 7,977,316 B2 | 7/2011 | Schenk | |
| 8,003,097 B2 | 8/2011 | Schroeter et al. | |
| 8,034,339 B2 | 10/2011 | Schenk | |
| 8,124,081 B2 | 2/2012 | Schenk | |
| 8,128,928 B2 | 3/2012 | Basi et al. | |
| 8,216,577 B2 | 7/2012 | Bardoff et al. | |
| 8,613,920 B2 | 12/2013 | Liberburg et al. | |
| 8,623,365 B2 | 1/2014 | Davies | |
| 8,784,810 B2 | 7/2014 | Liberburg et al. | |
| 8,916,165 B2 | 12/2014 | Basi et al. | |
| 9,051,363 B2 | 6/2015 | Basi et al. | |
| 9,067,981 B1 | 6/2015 | Basi | |
| 9,084,832 B2 | 7/2015 | Nordstrom et al. | |
| 9,221,812 B2 | 12/2015 | Kroth et al. | |
| 9,334,303 B2 | 5/2016 | Mediannikov et al. | |
| 9,493,496 B2 | 11/2016 | Geng et al. | |
| 9,535,076 B2 | 1/2017 | Kayed et al. | |
| 9,644,025 B2 | 5/2017 | Black et al. | |
| 2001/0016326 A1 | 8/2001 | Giulian | |
| 2001/0016327 A1 | 8/2001 | Giulian | |
| 2005/0169925 A1* | 8/2005 | Bardroff | A61P 25/00 530/388.26 |
| 2005/0267029 A1 | 12/2005 | Ancsin et al. | |
| 2007/0110750 A1 | 5/2007 | Glabe et al. | |
| 2008/0299111 A1 | 12/2008 | Delacourte | |
| 2009/0246191 A1 | 10/2009 | O'Nuallain et al. | |
| 2010/0081613 A1 | 4/2010 | Arancio et al. | |
| 2011/0171243 A1 | 7/2011 | Mandler et al. | |
| 2011/0182928 A1* | 7/2011 | Hoogerhout | C07K 14/4711 424/193.1 |
| 2013/0136747 A1 | 5/2013 | Bardroff et al. | |
| 2013/0252901 A1 | 9/2013 | Mediannikov et al. | |
| 2015/0105344 A1 | 4/2015 | Geng et al. | |
| 2015/0322143 A1 | 11/2015 | Kayed | |
| 2017/0021020 A1 | 1/2017 | Bollyky et al. | |
| 2018/0125920 A1 | 5/2018 | Cashman et al. | |
| 2018/0319856 A1 | 11/2018 | Cashman et al. | |
| 2018/0346535 A1 | 12/2018 | Cashman | |

FOREIGN PATENT DOCUMENTS

| | | | |
|---|---|---|---|
| EP | 1676859 A1 | 7/2006 | |
| EP | 2377860 A1 | 10/2011 | |
| JP | 2011-522841 A | 8/2011 | |
| WO | 88/09336 A1 | 5/1988 | |
| WO | 90/14387 A1 | 5/1990 | |
| WO | 91/17271 A1 | 5/1991 | |
| WO | 92/01047 A1 | 7/1991 | |
| WO | 96/14831 A1 | 11/1994 | |
| WO | 95/17211 A1 | 12/1994 | |
| WO | 1995/006477 A1 | 3/1995 | |
| WO | 95/34323 A1 | 6/1995 | |
| WO | 96/06627 A1 | 7/1995 | |
| WO | 01/62801 A2 | 2/2001 | |
| WO | 2001062801 A2 | 8/2001 | |
| WO | 2004/058239 A1 | 7/2003 | |
| WO | 2003070760 A2 | 8/2003 | |
| WO | 2004/013172 A2 | 2/2004 | |
| WO | 2004/029629 A1 | 4/2004 | |
| WO | 2004/071408 A2 | 8/2004 | |
| WO | 2006/066089 A1 | 12/2005 | |
| WO | 2006/069718 A1 | 7/2006 | |
| WO | 2006/095041 A1 | 9/2006 | |
| WO | 2006125324 A1 | 11/2006 | |
| WO | 2007/068429 A1 | 12/2006 | |
| WO | 2007/059000 A2 | 5/2007 | |
| WO | 2008/060364 A2 | 5/2008 | |
| WO | 2008/088983 A1 | 7/2008 | |
| WO | 2008088983 A2 | 7/2008 | |
| WO | 2008/156622 A1 | 12/2008 | |
| WO | 2009086539 A2 | 12/2008 | |
| WO | 2009/048537 A2 | 4/2009 | |
| WO | 2009/048538 A2 | 4/2009 | |
| WO | 2009/052439 A2 | 4/2009 | |
| WO | 2009/065054 A2 | 5/2009 | |
| WO | 2009/149486 A2 | 12/2009 | |
| WO | 2009149487 A2 | 12/2009 | |
| WO | 2010002251 A1 | 1/2010 | |
| WO | 2010/040209 A1 | 4/2010 | |
| WO | 2010119704 A1 | 10/2010 | |
| WO | 2010/128139 A1 | 11/2010 | |
| WO | 2011016238 A1 | 2/2011 | |
| WO | 2011/033046 A1 | 3/2011 | |
| WO | 2011/104696 A1 | 9/2011 | |
| WO | 2011/106885 A1 | 9/2011 | |
| WO | 2012/104824 A1 | 8/2012 | |
| WO | 2002/096937 A2 | 12/2012 | |
| WO | 2013/020723 | 2/2013 | |
| WO | 2013071267 A1 | 5/2013 | |
| WO | 2014/031697 A3 | 2/2014 | |
| WO | 2014/161875 A1 | 4/2014 | |
| WO | 2015/017900 A1 | 2/2015 | |
| WO | 2015031698 A1 | 3/2015 | |
| WO | 2015/113169 A1 | 8/2015 | |
| WO | 2017/079832 A1 | 5/2017 | |
| WO | 2017/079833 A1 | 5/2017 | |
| WO | 2017/079834 A1 | 5/2017 | |
| WO | 2017/079835 A1 | 5/2017 | |
| WO | 2017/079836 A1 | 5/2017 | |
| WO | 2018/014126 A1 | 1/2018 | |
| WO | 2019/014768 A1 | 1/2019 | |

OTHER PUBLICATIONS

Lu, J.X. et al. "Molecular Structure of Beta-Amyloid Fibrils in Alzheimer's Disease Brain Tissue" Cell vol. 154(6) p. 1257 (2013).

Xiao, Y. et al. A Beta (1-42) Fibril Structure Illuminates Self-Recognition and Replication of Amyloid in Alzheimer's Disease. Nat.Struct.Mol.Biol. vol. 22(6) p. 499-505 (2015).

Petkova, A. et al. Experimental Constraints on Quaternary Structure in Alzheimer's Beta-Amyloid Fibrils Biochemistry. vol. 45 p. 498 (2006).

Giulian, D. "The HHQK domain of β-amyloid provides a structural basis for the immunopathology of Alzheimer's disease." J. Biol. Chem. 1998, 273(45), 29719-26.

Winkler, K. "Competition of Aβ amyloid peptide and apolipoprotein E for receptor-mediated endocytosis." J. Lipid Res. 1999, 40(3), 447-55.

Crespi, Gabriela A. N. et al. "Molecular basis for mid-region amyloid-b capture by leading Alzheimer's disease immunotherapies." Scientific Reports. 5 : 9649, 2015.

Hilser, Vincent J. et al. "Structure-based calculation of the equilibrium folding pathway of proteins. correlation with hydrogen exchange protection factors." J. Mol. Biol., 262:756-772, 1996.

Cohen, Samuel I. A. et al. Proliferation of amyloid-β42 aggregates occurs through a secondary nucleation mechanism. Proc. Natl.l Acad. Sci. USA, 110(24):9758-9763, 2013.

Sormanni, Pietro et al. The camsol method of rational design of protein mutants with enhanced solubility. Journal of Molecular Biology, 427(2):478-490, 2015.

Blacker, Deborah et al. Reliability and Validity of NINCDS-ADRDA Criteria for Alzheimer's Disease The National Institute of Mental Health Genetics Initiative. Arch Neurol. 51(12):1198-1204 (1994).

Hamley, I.W. "PEG-Peptide Conjugates" 2014; 15, 1543-1559; dx.doi.org/10.1021/bm500246w.

(56) References Cited

OTHER PUBLICATIONS

Roberts, MJ. et al. "Chemistry for peptide and protein PEGylation" 64: 116-127.
Karlin, Samuel et al. Methods for assessing the statistical significance of molecular sequence features by using general scoring schemes. Proc. Natl. Acad. Sci. U.S.A. 87:2264-2268.
Karlin, Samuel et al. Applications and statistics for multiple high-scoring segments in molecular sequences. 1993, Proc. Natl. Acad. Sci. U.S.A. 90:5873-5877.
Altschul et al. Basic Local Alignment Search Tool. 1990, J. Mol. Biol. 215:403.
Altschul et al. Gapped BLAST and PSI-BLAST: a new generation of protein database search programs. 1997, Nucleic Acids Res. 25:3389-3402.
Myers et al. Optimal alignments in linear space. 1988, CABIOS 4:11-17.
Kohler G. et al. Continuous cultures of fused cells secreting antibody of predefined specificity. Nature 256:495-497, 1975.
Ward et al. Binding activities of a repertoire of single immunoglobulin variable domains secreted from *Escherichia coli.* Nature 41:544-546 1989.
Riechmann et al. Reshaping human antibodies for therapy. Nature, 332:323-327, 1988.
Yu Yz, et al. Strikingly reduced amyloid burden and improved behavioral performance in Alzheimer's disease mice immunized with recombinant chimeric vaccines by hexavalent foldable A_1-15 fused to toxin-derived carrier proteins. J Alzheimers Dis 2014;41:243-60.
Wang, Hc, et al. Peripherally administered sera antibodies recognizing amyloid-beta oligomers mitigate Alzheimer's disease-like pathology and cognitive decline in aged $3^x$ Tg-AD mice, Vaccine 2016.
Paganetti PA et al. Amyloid precursor protein truncated at any of the γ-secretase sites is not cleaved to β-amyloid, J.Neurosci. Res. 46 (1996) 283-293.
Kahlert H. et al. Characterization of major allergens of Parietaria officinalis. Int Arch Allergy Immunol Feb. 1996; 109 (2):141-9.
Kaplan, Johanne. Targeting of Toxic Amyloid-Beta Oligomer Species by Monoclonal Antibody PMN310: Precision Drug Design for Alzheimer's Disease. Abstract and slides presented at the Alzheimer's Association International Conference Jul. 17, 2017 in London, England.
NCBI Blast: Protein Sequence (8 letters). CDR-H1 GYSFTSYW. Retrieved on Feb. 8, 2017 from blast.ncbi.nlm.nih.gov/Blast.cgi.
NCBI Blast: Protein Sequence (9 letters). CDR-H2 VHPGRGVST. Retrieved on Feb. 8, 2017 from blast.ncbi.nlm.nih.gov/Blast.cgi.
NCBI Blast: Protein Sequence (13 letters). CDR-H3 SRSHGNTYWFFDV. Retrieved on Feb. 8, 2017 from blast.ncbi.nlm.nih.gov/Blast.cgi.
NCBI Blast: Protein Sequence (11 letters). CDR-L1 QSIVHSNGNTY. Retrieved on Feb. 8, 2017 from blast.ncbi.nlm.nih.gov/Blast.cgi.
NCBI Blast: Protein Sequence (3 letters). CDR-L2 KVS. Retrieved on Feb. 8, 2017 from blast.ncbi.nlm.nih.gov/Blast.cgi.
NCBI Blast: Protein Sequence (9 letters). CDR-L3 FQGSHVPFT. Retrieved on Feb. 8, 2017 from blast.ncbi.nlm.nih.gov/Blast.cgi.
Tjernberg L.O., et al. Arrest of Amyloid Fibril Formation by a Pentapeptide Ligand. The Journal of Biological Chemistry. vol. 271, No. 15, Issue of Apr. 12, pp. 8545-8548, 1996.
European Patent Application No. 16863264.4 Extended European Search Report dated Apr. 15, 2019.
Rudikoff et al., Single amino acid substitution altering antigen-binding specificity. Proc Natl Acad Sci USA 1982; 79:1979-1983.
MacCallum et al., Antibody-antigen Interactions: Contact Analysis and Binding Site Topography. J. Mol. Biol., 1996;262:732-745.
Pascalis et al., Grafting of "Abbreviated" Complementarity-Determining Regions Containing Specificity-Determining Regions Containing Specificity-Determining Residues Essential for Ligand Contact to Engineer a Less Immunogenic Humanized Monoclonal Antibody. The Journal of Immunology, 2002; 169: 3076-3084.

Casset et al., A peptide mimetic of an anti-CD4 monoclonal antibody by rational design. BBRC, 2003; 307:198-205.
Vajdos et al., Comprehensive Functional Maps of the Antigen-binding Site of an Anti-ErbB2 Antibody Obtained with Shotgun Scanning Mutagenesis. J. Mol. Med., 2002; 320: 415-428.
Holm et al., Functional mapping and single chain construction of the anti-cytokeratin 8 monoclonal antibody TS1. Mol. Immunol., 2007; 44: 1075-1084.
Chen et al., Selection and Analysis of an Optimized Anti-VEGF Antibody: Crystal Structure of an Affinity-matured Fab in Complex with Antigen. J. Mol. Bio., 1999; 293: 865-881.
Wu et al., Humanization of a Murine Monoclonal Antibody by Simultaneousl Optimization of Framework and CDR Residues. J. Mol. Biol.,1999; 294: 151-162.
Burgess et al., Possible Dissociation of the Heparin-binding and Mitogenic Activities of Heparin-binding (Acidic Fibroblast) Growth Factor-1 from its Receptor-binding Activities by Site-directed Mutagenesis of a Single Lysine Residue. J of Cell Bio. 1990, 111:2129-2138.
Bowie et al., Deciphering the Message in Protein Sequences: Tikerance to Amino Acid Substitutions. Science, 1990, 247:1306-1310.
Pawson et al., Assembly of Cell Regulatory Systems Through Protein Interaction Domains. Science, 2003, 300:445-452.
Alaoui-Ismaili et al., Design of second generation therapeutic recombinant bone morphogenetic proteins. Cytokine Growth Factor Rev. 2009; 20:501-507.
Guo et al., Protein tolerance to random amino acid change. PNAS 2004; 101:9205-9210.
Krafft, Grant et al. ACU-193: A candidate therapeutic antibody that selectively targets soluble beta-amyloid bligomers, Alzheimer's & Dementia: The Journal of the Alzheimer's Association, Jan. 1, 2013, p. p. 326-p. 326.
Hillen, Heinz et al. Generation and Therapeutic Efficacy of Highly Oligomer-Specific beta-Amyloid Antibodies, The Journal of Neuroscience, Society for Neuroscience, US, vol. 30, No. 31, Aug. 4, 2010, pp. 10369-10379.
Hoogerhout, Peter et al. A Cyclic Undecamer Peptide Mimics a Turn in Folded Alzheimer Amyloid β and Elicits Antibodies against Oligomeric and Fibrillar Amyloid and Plaques, Plos One, vol. 6, No. 4, Jan. 1, 2011, pp. e19110-e19110.
Manea, Marilena et al. Antibodiy Recognition and Conformational Flexibility of a Plaque-Specific β-Amyloid Epitope Modulated by Non-Native Peptide Flanking Regions. Journal of medicinal chemistry. 51(2008), p. pp. 1150-1161.
Fritschi, Sarah K. et al. Highly potent soluble amyloid- seeds in human Alzheimer brain but not cerebrospinal fluid. Brain: a journal of neurology 137: Pt 11. 2909-2915 Nov. 2014.
Kaplan Johanne. Harnessing the Power of Precision Medicine to Conquer Neurodegenerative Diseases. Presented Sep. 14, 2016.
Wilcock, Donna M. et al. Passive immunotherapy against Aβ in aged APP-transgenic mice reverses cognitive deficits and depletes parenchymal amyloid deposits in spite of increased vascular amyloid and microhemorrhage. Journal of Neuroinflammation, 2004, 1:24.
Racke, Margaret M. et al. Exacerbation of Cerebral Amyloid Angiopathy-Associated Microhemorrhage in Amyloid Precursor Protein Transgenic Mice by Immunotherapy Is Dependent on Antibody Recognition of Deposited Forms of Amyloid β. The Journal of Neuroscience, Jan. 19, 2005. 25(3):629-636.
Pfeifer M. et al. Cerebral Hemorrhage After Passive Anti-Aβ Immunotherapy. Science. vol. 298 Nov. 15, 2002.
Wilcock, Donna M. et al. Deglycosylated Anti-Amyloid-β Antibodies Eliminate Cognitive Deficits and Reduce Parenchymal Amyloid with Minimal Vascular Consequences in Aged Amyloid Precursor Protein Transgenic Mice. Journal of Neuroscience. May 17, 2006. 26(20):5340-5346.
Goni, Fernando et al. Production of Monoclonal Antibodies to Pathologic β-sheet Oligomeric Conformers in Neurodegenerative Diseases. Scientific Reports. Aug. 2017.
Anger, Franziska et al. Soluble Aβ Seeds Are Potent Inducers of Cerebral β-Amyloid Deposition. J Neurosci 31: 41. 14488-14495 Oct. 2011.

(56) References Cited

OTHER PUBLICATIONS

Sardar Sinha, Maitrayee et al. Alzheimer's disease pathology propagetion by exosomes containing toxic amyloid-beta oligomers. Acta Neuropathologica. Jun. 2018.

Kaplan, Johanne. Pre-Clinical: Basic Therapeutics—Targeting Amyloid or TAU. Presented at the Alzheimer's International Conference Jul. 2007.

Aprile, Francesco A. et al. Selective targeting of primary and secondary nucleation pathways in Aβ42 aggregation using a rational antibody scanning method. Molecular Neuroscience, Science Advances; 2017, 3. Jun. 21, 2017.

Wang, J. et al. Effects of an amyloid-beta 1-42 oligomers antibody screened from a phage display library in APP/PS1 transgenic mice. Brain Res. Mar. 15, 2016, vol. 1635, pp. 169-179.

Silverman, Judith et al. Novel Amyloid-β Oligomer-Specific Epitopes: A Hypothesis Drivin Aproach to Alzheimer's Immunotherapeutics. Abstract presented at the Alzheimer's Association International Conference Jul. 2016.

Gibbs, Ebrima et al. Rational generation of Aβ oligomer-specific antibodies through computational identification of conformational epitopes. Abstract presented at the Alzheimer's Association International Conference on Jul. 2017.

Plotkin, Steven et al. A computational Method to Predict Disease-Specific Epitopes in Aβ, and its Application to Oligomer-Selective Antibodies for Alzheimer's Immunotherapy. Presented at the Alzheimer's association international conference on Jul. 27, 2016.

Hollta, Mikko et al. Evaluating Amyloid-β Oligomers in Cerebrospinal Fluid as a Biomarker for Alzheimer's Disease. Plos One. Jun. 2013, vol. 8, Issue 6.

Plotkin, Steven et al. Achieving the optimal profile for Alzheimer's immunotherapy: Rational generation of antibodies specific for toxic Aβ oligomers. Abstract presented at the American Academy of Neurology conference on Apr. 2017.

Cashman, Neil et al. Epitope Identification of Toxic Propagating Strains of Aβ Oligomers. presented at PRION 2017, the International Conference Deciphering Neurodegenerative Disorders in Edinburgh, Scottland on May 25, 2017.

Fukumoto, H. et al. High-molecular-weight beta-amyloid oligomers are elevated in cerebrospinal fluid of Alzheimer patients. The FASEB Journal 24, 2716-2726, 2010.

Lesne, S. E. et al. Brain amyloid-beta oligomers in ageing and Alzheimer's disease. Brain 136, 1383-1398, 2013.

Ferreira, S. T. et al. Soluble amyloid-b oligomers as synaptotoxins leading to cognitive impairment in Alzheimer's disease. Frontiers in Cellular Neuroscience 9, (2015).

Figueiredo, C. P. et al. Memantine rescues transient cognitive impairment caused by high-molecular-weight abeta pligomers but not the persistent impairment induced by low-molecular-weight oligomers. J Neurosci 33, 9626-9634, 2013.

Tapiola, Tero, et al. Cerebrospinal Fluid β-Amyloid 42 and Tau Proteins as Biomarkers of Alzheimer-Type Pathologic Changes in the Brain. Arch Neurol. 2009, 66(3):382-389.

Arai, Tadamasa et al. A Cyclic KLVFF-Derived Peptide Aggregation Inhibitor Induces the Formation of Less-Toxic Off-Pathway Amyloid-β Oligomers, Chembiochem, vol. 15, No. 17, Sep. 26, 2014, pp. 2577-2583.

Cho, Patricia Y. et al. A Cyclic Peptide Mimic of the β-Amyloid Binding Domain on Transthyretin, ACS Chemical Neuroscience, vol. 6, No. 5, Mar. 9, 2015, pp. 778-789.

Liu, Cong et al. Characteristics of Amyloid-Related Oligomers Revealed by Crystal Structures of Macrocyclic β-Sheet Mimics, Journal of the American Chemical Society, vol. 133, No. 17, May 4, 2011, pp. 6736-6744.

Perez De La Lastra, J. M. et al. Epitope mapping of 10 monoclonal antibodies against the pig analogue of human membrane cofactor protein (MCP), Immunology, vol. 96, No. 4, Apr. 1, 1999, pp. 663-670.

\* cited by examiner

FIG. 11 A: Two views of the side chain orientations superimposed for the linear peptide (black) and cyclic peptide (light grey)
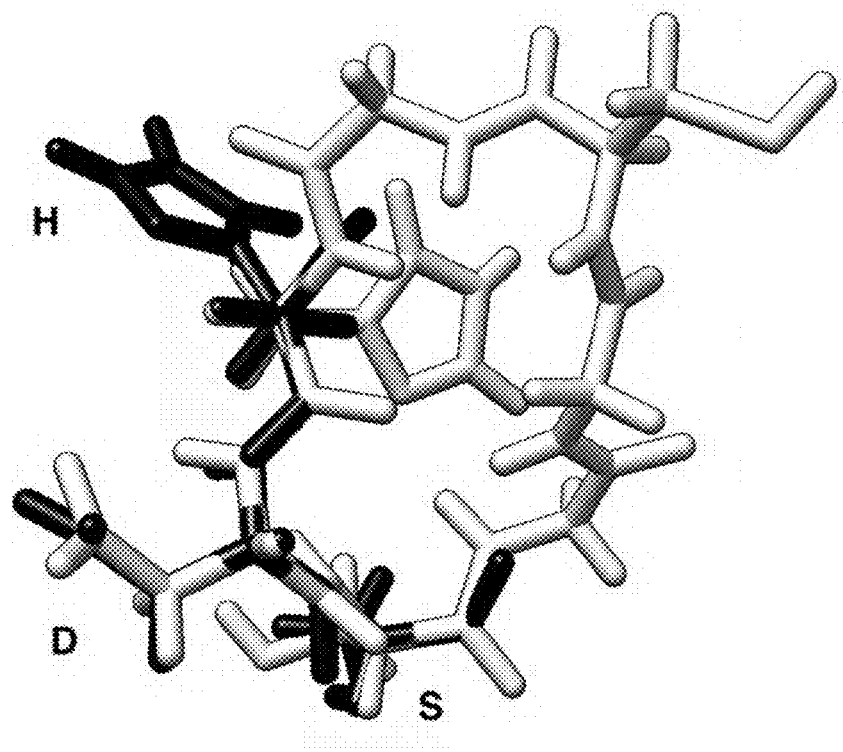
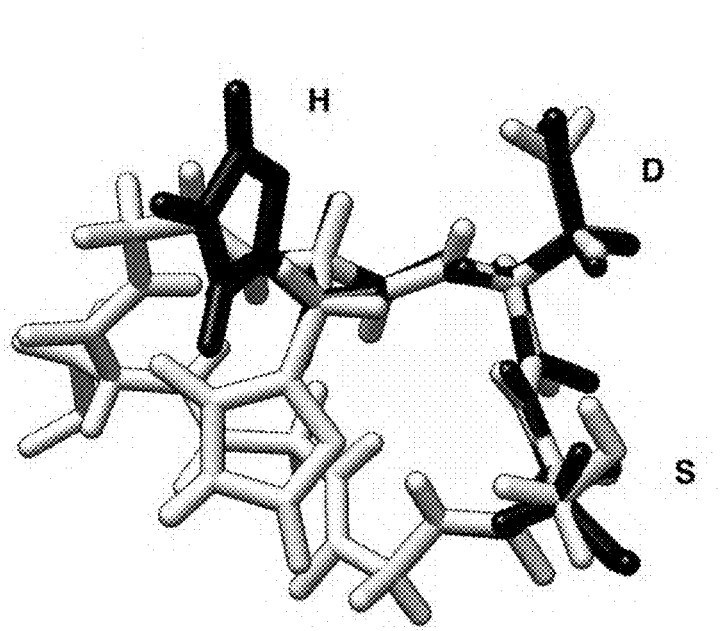

Cyclo(CGHDSGG)
Chemical Formula: $C_{22}H_{31}N_9O_{10}S$
Molecular Weight: 613.60

Cyclo(CGHDSG-PEG2)
Chemical Formula: $C_{26}H_{39}N_9O_{12}S$
Molecular Weight: 701.71

Cyclo(C-PEG2-HDSGG)
Chemical Formula: $C_{26}H_{39}N_9O_{12}S$
Molecular Weight: 701.71

Clustering of the cyclic peptide ensemble along with other strain fibril models.

A.

B.

A.

B.

C.

D.

SEQUENCE LISTING

<160> NUMBER OF SEQ ID NOS: 28

<210> SEQ ID NO 1
<211> LENGTH: 4
<212> TYPE: PRT
<213> ORGANISM: Homo sapiens

<400> SEQUENCE: 1

His Asp Ser Gly
1

<210> SEQ ID NO 2
<211> LENGTH: 7
<212> TYPE: PRT
<213> ORGANISM: Artificial Sequence
<220> FEATURE:
<223> OTHER INFORMATION: Synthetic Construct

<400> SEQUENCE: 2

Cys Gly His Asp Ser Gly Gly
1               5

<210> SEQ ID NO 3
<211> LENGTH: 42
<212> TYPE: PRT
<213> ORGANISM: Homo sapiens

<400> SEQUENCE: 3

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 4
<211> LENGTH: 5
<212> TYPE: PRT
<213> ORGANISM: Homo sapiens

<400> SEQUENCE: 4

His Asp Ser Gly Tyr
1               5

<210> SEQ ID NO 5
<211> LENGTH: 5
<212> TYPE: PRT
<213> ORGANISM: Homo sapiens

<400> SEQUENCE: 5

Arg His Asp Ser Gly
1               5

<210> SEQ ID NO 6
<211> LENGTH: 4
<212> TYPE: PRT
<213> ORGANISM: Homo sapiens

<400> SEQUENCE: 6

Arg His Asp Ser
1

<210> SEQ ID NO 7
<211> LENGTH: 5

```
<212> TYPE: PRT
<213> ORGANISM: Artificial Sequence
<220> FEATURE:
<223> OTHER INFORMATION: Synthetic Construct

<400> SEQUENCE: 7

Gly His Asp Ser Gly
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic Construct

<400> SEQUENCE: 8

Gly His Asp Ser Gly Gly
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic Construct

<400> SEQUENCE: 9

Gly Gly His Asp Ser Gly Gly
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic Construct

<400> SEQUENCE: 10

Gly His Asp Ser Gly Gly Gly
1               5

<210> SEQ ID NO 11
<211> LENGTH: 6
<212> TYPE: PRT
<213> ORGANISM: Homo sapiens

<400> SEQUENCE: 11

His Asp Ser Gly Tyr Glu
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic Construct

<400> SEQUENCE: 12

Cys Gly His Asp Ser Gly Gly Cys
1               5

<210> SEQ ID NO 13
<211> LENGTH: 6
<212> TYPE: PRT
<213> ORGANISM: Homo sapiens
```

```
<400> SEQUENCE: 13

Arg His Asp Ser Gly Tyr
1               5

<210> SEQ ID NO 14
<211> LENGTH: 4
<212> TYPE: PRT
<213> ORGANISM: Homo sapiens

<400> SEQUENCE: 14

Asp Ser Gly Tyr
1

<210> SEQ ID NO 15
<211> LENGTH: 6
<212> TYPE: PRT
<213> ORGANISM: Homo sapiens

<400> SEQUENCE: 15

Asp Ser Gly Tyr Glu Val
1               5

<210> SEQ ID NO 16
<211> LENGTH: 6
<212> TYPE: PRT
<213> ORGANISM: Homo sapiens

<400> SEQUENCE: 16

Phe Arg His Asp Ser Gly
1               5

<210> SEQ ID NO 17
<211> LENGTH: 8
<212> TYPE: PRT
<213> ORGANISM: Mus musculus

<400> SEQUENCE: 17

Gly Tyr Thr Phe Thr Ser Tyr Trp
1               5

<210> SEQ ID NO 18
<211> LENGTH: 8
<212> TYPE: PRT
<213> ORGANISM: Mus musculus

<400> SEQUENCE: 18

Ile Asp Pro Ser Asp Ser Gln Thr
1               5

<210> SEQ ID NO 19
<211> LENGTH: 5
<212> TYPE: PRT
<213> ORGANISM: Mus musculus

<400> SEQUENCE: 19

Ser Arg Gly Gly Tyr
1               5

<210> SEQ ID NO 20
<211> LENGTH: 6
<212> TYPE: PRT
<213> ORGANISM: Mus musculus

<400> SEQUENCE: 20
```

Gln Asp Ile Asn Asn Tyr
1               5

<210> SEQ ID NO 21
<211> LENGTH: 3
<212> TYPE: PRT
<213> ORGANISM: Mus musculus

<400> SEQUENCE: 21

Tyr Thr Ser
1

<210> SEQ ID NO 22
<211> LENGTH: 8
<212> TYPE: PRT
<213> ORGANISM: Mus musculus

<400> SEQUENCE: 22

Leu Gln Tyr Asp Asn Leu Trp Thr
1               5

<210> SEQ ID NO 23
<211> LENGTH: 393
<212> TYPE: DNA
<213> ORGANISM: Mus musculus

<400> SEQUENCE: 23

```
atgggatgga gctgtatcat cctcttcttg gtagcaacag ctacaggtgt ccactcccag      60
gtccaactgc agcagcctgg ggctgagctg gtgaggcctg gggcttcagt gaagctgtcc     120
tgcaaggctt ctggctacac cttcaccagc tactggatga actgggtgaa gcagaggcct     180
ggacaaggcc ttgaatggat tggtatgatt gatccttcag acagtcaaac tcactacaat     240
caaatgttca aggacaaggc cacattgact gtagacaaat cctccagcac agcctacctg     300
cagctcagca gcctgacatc tgaggactct gcggtctatt actgttcaag agggggctac     360
tggggccaag gcaccactct cacagtctcc tca                                  393
```

<210> SEQ ID NO 24
<211> LENGTH: 131
<212> TYPE: PRT
<213> ORGANISM: Mus musculus

<400> SEQUENCE: 24

Met Gly Trp Ser Cys Ile Ile Leu Phe Leu Val Ala Thr Ala Thr Gly
1               5                   10                  15

Val His Ser Gln Val Gln Leu Gln Gln Pro Gly Ala Glu Leu Val Arg
            20                  25                  30

Pro Gly Ala Ser Val Lys Leu Ser Cys Lys Ala Ser Gly Tyr Thr Phe
        35                  40                  45

Thr Ser Tyr Trp Met Asn Trp Val Lys Gln Arg Pro Gly Gln Gly Leu
    50                  55                  60

Glu Trp Ile Gly Met Ile Asp Pro Ser Asp Ser Gln Thr His Tyr Asn
65                  70                  75                  80

Gln Met Phe Lys Asp Lys Ala Thr Leu Thr Val Asp Lys Ser Ser Ser
                85                  90                  95

Thr Ala Tyr Leu Gln Leu Ser Ser Leu Thr Ser Glu Asp Ser Ala Val
            100                 105                 110

Tyr Tyr Cys Ser Arg Gly Gly Tyr Trp Gly Gln Gly Thr Thr Leu Thr
        115                 120                 125

Val Ser Ser
    130

<210> SEQ ID NO 25
<211> LENGTH: 378
<212> TYPE: DNA
<213> ORGANISM: Mus musculus

<400> SEQUENCE: 25
atgagaccgt ctattcagtt cctggggctc ttgttgttct ggcttcatgg tgctcagtgt      60
gacatccaga tgacacagtc tccatcctca ctgtctgcat ctctgggagg caaagtcacc     120
atcacttgca aggcaagcca agacattaac aactatatag cttggtacca acacaagcct     180
ggaaaaggtc ctaggcagct catatattac acatctacat tgcagccagg catcccatca     240
aggttcagtg aagtgggtc tgggagagat tattccttca ccatcagcga cctggagcct      300
gaagatattg caacttatta ttgtctacag tatgataatc tgtggacgtt cggtggaggc     360
accaagctgg aaatcaaa                                                   378

<210> SEQ ID NO 26
<211> LENGTH: 126
<212> TYPE: PRT
<213> ORGANISM: Mus musculus

<400> SEQUENCE: 26

Met Arg Pro Ser Ile Gln Phe Leu Gly Leu Leu Leu Phe Trp Leu His
1               5                   10                  15

Gly Ala Gln Cys Asp Ile Gln Met Thr Gln Ser Pro Ser Ser Leu Ser
            20                  25                  30

Ala Ser Leu Gly Gly Lys Val Thr Ile Thr Cys Lys Ala Ser Gln Asp
        35                  40                  45

Ile Asn Asn Tyr Ile Ala Trp Tyr Gln His Lys Pro Gly Lys Gly Pro
    50                  55                  60

Arg Gln Leu Ile Tyr Tyr Thr Ser Thr Leu Gln Pro Gly Ile Pro Ser
65                  70                  75                  80

Arg Phe Ser Gly Ser Gly Ser Gly Arg Asp Tyr Ser Phe Thr Ile Ser
                85                  90                  95

Asp Leu Glu Pro Glu Asp Ile Ala Thr Tyr Tyr Cys Leu Gln Tyr Asp
            100                 105                 110

Asn Leu Trp Thr Phe Gly Gly Gly Thr Lys Leu Glu Ile Lys
        115                 120                 125

<210> SEQ ID NO 27
<211> LENGTH: 6
<212> TYPE: PRT
<213> ORGANISM: Artificial Sequence
<220> FEATURE:
<223> OTHER INFORMATION: Synthetic Construct

<400> SEQUENCE: 27

Cys Gly His Asp Ser Gly
1               5

<210> SEQ ID NO 28
<211> LENGTH: 6
<212> TYPE: PRT

```
<213> ORGANISM: Artificial Sequence
<220> FEATURE:
<223> OTHER INFORMATION: Synthetic Construct

<400> SEQUENCE: 28

Cys His Asp Ser Gly Gly
1               5
```

N-TERMINAL EPITOPES IN AMYLOID BETA AND CONFORMATIONALLY-SELECTIVE ANTIBODIES THERETO

RELATED APPLICATIONS

This application is a continuation of U.S. patent application Ser. No. 15/774,805, filed May 9, 2018, which is a national phase entry of PCT/CA2016/051300, filed Nov. 9, 2016, which claims the benefit of priority of U.S. Patent Application Ser. No. 62/253,044, filed Nov. 9, 2015; U.S. Patent Application Ser. No. 62/331,925, filed on May 4, 2016; U.S. Patent Application Ser. No. 62/365,634, filed on Jul. 22, 2016; and U.S. Patent Application Ser. No. 62/393,615, filed on Sep. 12, 2016, each of which are incorporated herein by reference.

INCORPORATION OF SEQUENCE LISTING

A computer readable form of the Sequence Listing "P50440US02_SequenceListing.txt" (7,709 bytes), submitted via EFS-Web and created on Sep. 2, 2020, is herein incorporated by reference.

FIELD

The present disclosure relates to N-terminal Amyloid beta (A-beta or Aβ) epitopes and antibodies thereto and more specifically to conformational A-beta epitopes that are for example selectively accessible in A-beta oligomers, and related antibody compositions.

BACKGROUND

Amyloid-beta (A-beta), which exists as a 36-43 amino acid peptide, is a product released from amyloid precursor protein (APP) by the enzymes β and γ secretase. In Alzheimer's disease (AD) patients, A-beta can be present in soluble monomers, insoluble fibrils and soluble oligomers. In monomer form, A-beta exists as a predominantly unstructured polypeptide chain. In fibril form, A-beta can aggregate into distinct morphologies, often referred to as strains. Several of these structures have been determined by solid-state NMR.

For, example, structures for several strains of fibrils are available in the Protein Data Bank (PDB), a crystallographic database of atomic resolution three dimensional structural data, including a 3-fold symmetric Aβ structure (PDB entry, 2M4J); a two-fold symmetric structure of Aβ-40 monomers (PDB entry 2LMN), and a single-chain, parallel in-register structure of Aβ-42 monomers (PDB entry 2MXU).

The structure of 2M4J is reported in Lu et al [8], and the structure of 2MXU is reported in Xiao et al [9]. The structure of 2LMN is reported in Petkova et al [10].

A-beta oligomers have been shown to kill cell lines and neurons in culture and block a critical synaptic activity that subserves memory, referred to as long term potentiation (LTP), in brain slice cultures and living animals.

The structure of the oligomer has not been determined to date. Moreover, NMR and other evidence indicates that the oligomer exists not in a single well-defined structure, but in a conformationally-plastic, malleable structural ensemble with limited regularity. Moreover, the concentration of toxic oligomer species is far below either that of the monomer or fibril (estimates vary but are on the order of 1000-fold below or more), making this target elusive.

Antibodies that bind A-beta have been described.

U.S. Pat. No. 7,780,963 Anti-ADDL Antibodies relates to antibodies that differentially recognize multidimensional conformations of A-beta derived diffusible ligands U.S. Pat. No. 9,176,151 describes selective anti-Aβ oligomer antibodies, kits and an immunoassay method using a pair of anti-Aβ oligomer antibodies for detecting Aβ oligomers in a biological sample of a patient.

WO2003070760 titled ANTI-AMYLOID BETA ANTIBODIES AND THEIR USE is directed towards antibody molecules capable of specifically recognizing two regions of the β-A4 peptide.

WO2006066089 titled HUMANIZED AMYLOID BETA ANTIBODIES FOR USE IN IMPROVING COGNITION is directed to improved agents and methods for treatment of diseases associated with beta amyloid and in particular to the identification and characterization of a monoclonal antibody, 12A11, that specifically binds to Aβ peptide and is effective at reducing plaque burden associated with amyloidogenic disorders (e.g., AD).

WO2007068429 titled ANTIBODIES AGAINST AMYLOID BETA 4 WITH GLYCOSYLATED IN THE VARIABLE REGION is directed to a purified antibody molecule preparation being characterized in that at least one antigen binding site comprises a glycosylated asparagine (Asn) in the variable region of the heavy chain ($V_H$).

Yu et al. describes a hexavalent foldable Aβ1-15 (6Aβ15) fused to PADRE or toxin-derived carrier proteins. Wang et al. 2016 report that peripheral administration of this antibody mitigates Alzheimer's disease like pathology and cognitive decline in a transgenic animal model of aged Alzheimer Disease [11], [12].

Antibodies that preferentially or selectively bind A-beta oligomers over monomers or over fibrils or over both monomers and fibrils are desirable.

SUMMARY

Described herein are epitopes and more particularly conformational epitopes, in A-beta comprising and/or consisting of residues HDSG (SEQ ID NO:1) or related epitopes, and antibodies that specifically and/or selectively bind said epitopes. The epitopes may be selectively exposed in the oligomeric species of A-beta, in a conformation that distinguishes oligomeric species from that in the monomer and/or fibril.

An aspect includes a cyclic compound, preferably a cyclic compound, comprising: an A-beta peptide the peptide comprising HDS and up to 6 A-beta contiguous residues, and a linker, wherein the linker is covalently coupled to the A-beta peptide N-terminus residue and the A-beta C-terminus residue.

In an embodiment, the A-beta peptide is selected from a peptide having a sequence of any one of SEQ ID NOS: 1-16, optionally selected from HDSG (SEQ ID NO: 1), HDSGY (SEQ ID NO: 4), HDSGYE (SEQ ID NO: 11), RHDSGY (SEQ ID NO: 13), RHDSG (SEQ ID NO: 5), RHDS (SEQ ID NO: 6) and DSGY (SEQ ID NO: 14).

In another embodiment, the cyclic compound is a cyclic peptide.

In another embodiment, the cyclic compound described herein comprises i) a curvature increase of D and/or S in the compound of at least 10%, at least 20%, or at least 30% compared to D or S in the context of a corresponding linear compound; ii) at least one residue selected from H, D and S, wherein at least one dihedral angle of said residue is different by at least 30 degrees, at least 40 degrees, at least 50 degrees, at least 60 degrees, at least 70 degrees, or at least 80 degrees compared to the corresponding dihedral angle in the context of a corresponding linear compound; iii) an O-C-Cα-Cβ dihedral angle in D that is different by at least 30 degrees, at least 40 degrees, at least 50 degrees, at least 60 degrees, at least 70 degrees or at least 80 degrees compared to the corresponding dihedral angle in the context of a corresponding linear compound; and/or iv) a conformation for H and/or D as measured by entropy that is at least 10%, at least 20%, at least 25%, at least 30%, at least 35%, at least 40% more constrained compared to a corresponding linear compound.

In another embodiment, the A-beta peptide is selected from HDSG (SEQ ID NO: 1), HDSGY (SEQ ID NO: 4) and RHDSG (SEQ ID NO: 5).

In another embodiment, the compound further comprises a detectable label.

In another embodiment, the linker comprises or consists of 1-8 amino acids and/or equivalently functioning molecules and/or one or more functionalizable moieties.

In another embodiment, the linker amino acids are selected from A and G, and/or wherein the functionalizable moiety is C.

In another embodiment, the linker comprises or consists of amino acids GCG or CGC.

In another embodiment, the linker comprises a PEG molecule.

In another embodiment, the cyclic compound is selected from the structures shown in FIG. 11B.

An aspect includes an immunogen comprising the cyclic compound described herein.

In an embodiment, the compound is coupled to a carrier protein or immunogenicity enhancing agent.

In another embodiment, the carrier protein is bovine serum albumin (BSA) or the immunogenicity-enhancing agent is keyhole Keyhole Limpet Haemocyanin (KLH).

An aspect includes a composition comprising the compound described herein or the immunogen described herein.

In an embodiment, the immunogen comprising compositions described herein further comprises an adjuvant.

In another embodiment, the adjuvant is aluminum phosphate or aluminum hydroxide.

An aspect includes an isolated antibody that specifically binds to an A-beta peptide having a sequence of HDSG (SEQ ID NO: 1) or a related epitope sequence, optionally as set forth in any one of SEQ ID NOS: 1-16.

In an embodiment, the antibody specifically binds an epitope on A-beta, wherein the epitope comprises at least two consecutive amino acid residues predominantly involved in binding to the antibody, wherein the at least two consecutive amino acids are DS embedded within HDS, or wherein the at least two consecutive amino acids are HD embedded within HDS.

In another embodiment, the epitope comprises or consists of HDS, DSG, HDSG (SEQ ID NO: 1), HDSGY (SEQ ID NO: 4), HDSGYE (SEQ ID NO: 11), RHDSGY (SEQ ID NO: 13), RHDSG (SEQ ID NO: 5), RHDS (SEQ ID NO: 6) and DSGY (SEQ ID NO: 14).

In another embodiment, the antibody is a conformation specific and/or selective antibody that specifically or selectively binds to HDSG (SEQ ID NO: 1) or a related epitope peptide presented in a cyclic compound, optionally a cyclic compound described herein, preferably a cyclic peptide having a sequence as set forth in SEQ ID NO: 2 or 12.

In another embodiment, the antibody selectively binds A-beta oligomer over A-beta monomer and/or A-beta fibril.

In another embodiment, the selectivity is at least 2 fold, at least 3 fold, at least 5 fold, at least 10 fold, at least 20 fold, at least 30 fold, at least 40 fold, at least 50 fold, at least 100 fold, at least 500 fold, at least 1000 fold more selective for A-beta oligomer over A-beta monomer and/or A-beta fibril.

In another embodiment, the antibody does not specifically and/or selectively bind a linear peptide comprising sequence HDSG (SEQ ID NO: 1) or a related epitope, optionally wherein the sequence of the linear peptide is a linear version of a cyclic compound used to raise the antibody, optionally a linear peptide having a sequence as set forth in SEQ ID NO: 2 or 12.

In another embodiment, the antibody lacks or has negligible binding to A-beta monomer and/or A-beta fibril plaques in situ.

In another embodiment, the antibody is a monoclonal antibody or a polyclonal antibody.

In another embodiment, the antibody is a humanized antibody.

In another embodiment, the antibody is an antibody binding fragment selected from Fab, Fab', F(ab')2, scFv, dsFv, ds-scFv, dimers, nanobodies, minibodies, diabodies, and multimers thereof.

Another embodiment comprises a light chain variable region and a heavy chain variable region, optionally fused, the heavy chain variable region comprising complementarity determining regions CDR-H1, CDR-H2 and CDR-H3, the light chain variable region comprising complementarity determining region CDR-L1, CDR-L2 and CDR-L3 and with the amino acid sequences of said CDRs comprising the sequences:

```
                          (SEQ ID NO: 17)
CDR-H1  GYTFTSYW (SEQ ID NO: 18)
CDR-H2  IDPSDSQT (SEQ ID NO: 19)
CDR-H3  SRGGY (SEQ ID NO: 20)
CDR-L1  QDINNY (SEQ ID NO: 21)
CDR-L2  YTS (SEQ ID NO: 22)
CDR-L3  LQYDNLWT
```

In another embodiment, the antibody comprises a heavy chain variable region comprising: i) an amino acid sequence as set forth in SEQ ID NO: 24; ii) an amino acid sequence with at least 50%, at least 60%, at least 70%, at least 80% or at least 90% sequence identity to SEQ ID NO: 24, wherein the CDR sequences are as set forth in SEQ ID NO: 17, 18 and 19, or iii) a conservatively substituted amino acid sequence i).

In another embodiment, the antibody comprises a light chain variable region comprising i) an amino acid sequence as set forth in SEQ ID NO: 26, ii) an amino acid sequence with at least 50%, at least 60%, at least 70%, at least 80%, or at least 90% sequence identity to SEQ ID NO: 26, wherein the CDR sequences are as set forth in SEQ ID NO: 20, 21 and 22, or iii) a conservatively substituted amino acid sequence of i).

In another embodiment, the heavy chain variable region amino acid sequence is encoded by a nucleotide sequence as set forth in SEQ ID NO: 23 or a codon degenerate or optimized version thereof; and/or the antibody comprises a light chain variable region amino acid sequence encoded by a nucleotide sequence as set out in SEQ ID NO: 25 or a codon degenerate or optimized version thereof.

In another embodiment, the heavy chain variable region comprises or consists of an amino acid sequence as set forth in SEQ ID NO: 24 and/or the light chain variable region comprises or consists of an amino acid sequence as set forth in SEQ ID NO: 26.

In another embodiment, the antibody competes for binding to human A-beta with an antibody comprising the CDR sequences as recited in Table 10.

In an embodiment, the antibody is prepared using a cyclic compound or immunogen described herein.

An aspect includes an immunoconjugate comprising an antibody described herein and a detectable label or cytotoxic agent.

In an embodiment, the detectable label comprises a positron emitting radionuclide, optionally for use in subject imaging such as PET imaging.

An aspect includes an antibody described herein, or an immunoconjugate described herein, optionally with a diluent.

An aspect includes a nucleic acid molecule encoding a proteinaceous portion of the compound or immunogen described herein, the antibody described herein or proteinaceous immunoconjugates described herein.

An aspect includes a vector described herein.

An aspect includes a cell expressing an antibody described herein, optionally wherein the cell is a hybridoma comprising the vector.

An aspect includes a kit described herein, the immunogen described herein, the antibody described herein, the immunoconjugate described herein, the nucleic acid molecule described herein, the vector described herein or the cell described herein.

An aspect includes a method of making the antibody described herein, comprising administering the compound or immunogen described herein or a composition comprising said compound or immunogen to a subject and isolating antibody and/or cells expressing antibody specific or selective for the compound or immunogen administered and/or A-beta oligomers, optionally lacking or having negligible binding to a linear peptide comprising the A-beta peptide and/or lacking or having negligible plaque binding.

An aspect includes a method of determining if a biological sample comprises A-beta, the method comprising:
 a. contacting the biological sample with an antibody described herein or the immunoconjugate described herein; and
 b. detecting the presence of any antibody complex.

In an embodiment, the method described herein for determining if the biological sample contains A-beta oligomer the method comprising:
 a. contacting the sample with the antibody described herein or the immunoconjugate described herein that is specific and/or selective for A-beta oligomers under conditions permissive for forming an antibody: A-beta oligomer complex; and
 b. detecting the presence of any complex;
 wherein the presence of detectable complex is indicative that the sample may contain A-beta oligomer.

In another embodiment, the amount of complex is measured.

In another embodiment, the sample comprises brain tissue or an extract thereof, whole blood, plasma, serum and/or CSF.

In another embodiment, the sample is a human sample.

In another embodiment, the sample is compared to a control, optionally a previous sample.

In another embodiment, the level of A-beta is detected by SPR.

An aspect includes a method of measuring a level of A-beta in a subject, the method comprising administering to a subject at risk or suspected of having or having AD, an immunoconjugate comprising an antibody described herein wherein the antibody is conjugated to a detectable label; and detecting the label, optionally quantitatively detecting the label.

In an embodiment the label is a positron emitting radionuclide.

An aspect includes a method of inducing an immune response in a subject, comprising administering to the subject a compound or combination of compounds described herein, optionally a cyclic compound comprising HDSG (SEQ ID NO: 1) or a related epitope peptide sequence, an immunogen and/or composition comprising said compound or said immunogen; and optionally isolating cells and/or antibodies that specifically or selectively bind the A-beta peptide in the compound or immunogen administered.

An aspect includes a method of inhibiting A-beta oligomer propagation, the method comprising contacting a cell or tissue expressing A-beta with or administering to a subject in need thereof an effective amount of an A-beta oligomer specific or selective antibody or immunoconjugate described herein, to inhibit A-beta aggregation and/or oligomer propagation.

An aspect includes a method of treating AD and/or other A-beta amyloid related diseases, the method comprising administering to a subject in need thereof i) an effective amount of an antibody or immunoconjugate described herein, optionally an A-beta oligomer specific or selective antibody, or a pharmaceutical composition comprising said antibody; 2) administering an isolated cyclic compound comprising HDSG (SEQ ID NO: 1) or a related epitope sequence or immunogen or pharmaceutical composition comprising said cyclic compound, or 3) a nucleic acid or vector comprising a nucleic acid encoding the antibody of 1 or the immunogen of 2, to a subject in need thereof.

In an embodiment, a biological sample from the subject to be treated is assessed for the presence or levels of A-beta using an antibody described herein.

In an embodiment, more than one antibody or immunogen is administered.

In an embodiment, the antibody, immunoconjugate, immunogen, composition or nucleic acid or vector is administered directly to the brain or other portion of the CNS.

In an embodiment, the composition is a pharmaceutical composition comprising the compound or immunogen in admixture with a pharmaceutically acceptable, diluent or carrier.

An aspect includes an isolated peptide comprising an A beta peptide consisting of the sequence of any one of the sequences set forth in SEQ ID NOS: 1-16.

In an embodiment, the isolated peptide is a cyclic peptide comprising a linker wherein the linker is covalently coupled to the A-beta peptide N-terminus residue and/or the A-beta C-terminus residue.

In an embodiment, the isolated cyclic peptide comprises a detectable label.

An aspect includes a nucleic acid sequence encoding the isolated peptide described herein.

An aspect includes a hybridoma expressing the antibody described herein.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

An embodiment of the present disclosure will now be described in relation to the drawings in which:

FIG. 11A: Two views of the cyclic peptide structure CGHDSGG (SEQ ID NO: 2), rendered in licorice representation so the orientations of the side chains can be seen. The light gray colored conformation is the centroid of the largest cluster, as described above for FIG. 10, and best represents the typical conformation of the cyclic peptide. The black side chains are rendered for a linear conformation having dihedral angles close to the most likely dihedral angles of the linear peptide; the side chains for this linear peptide conformation are superimposed on the cyclic peptide, to show that different dihedral angles tend to be preferred for the linear and cyclic peptides.

Figure 1:
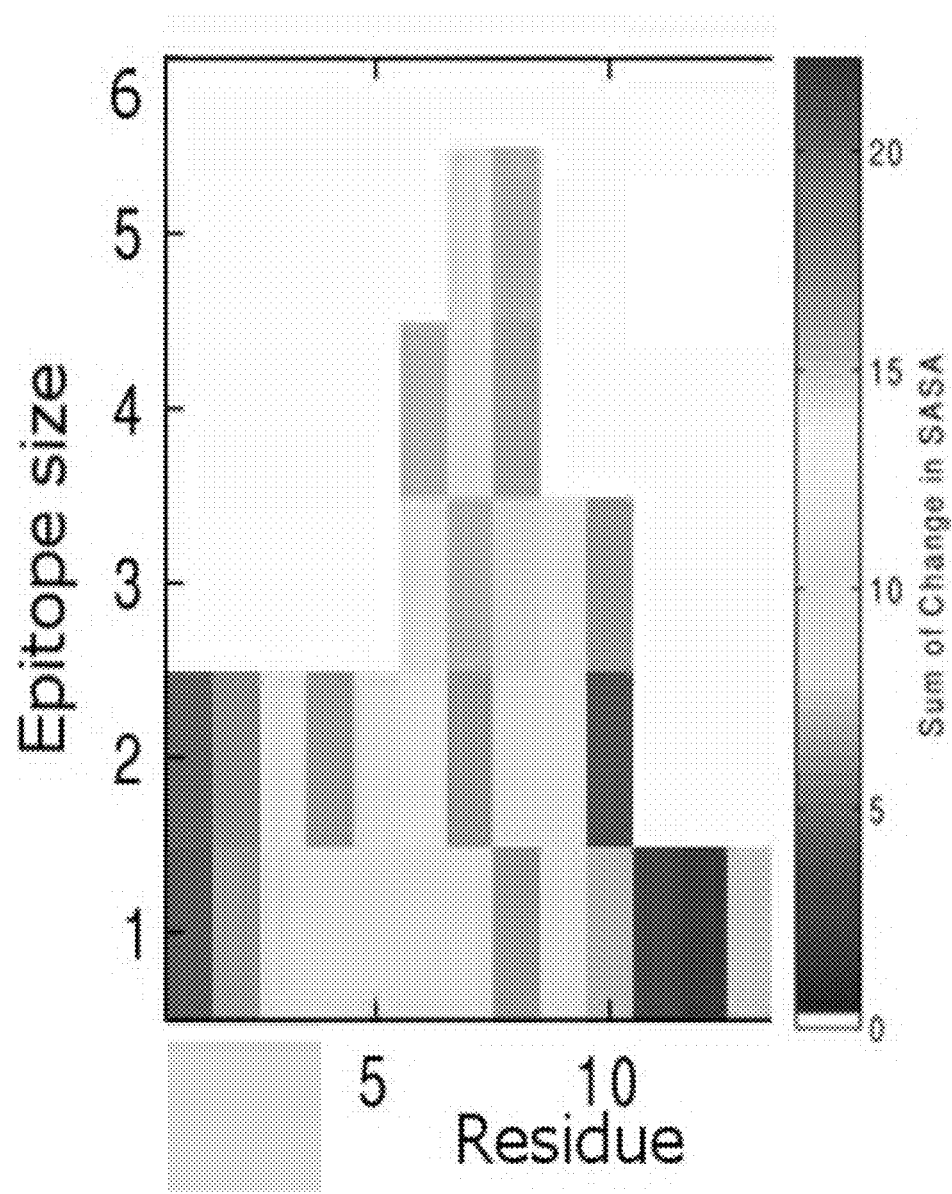
FIG. 1: Likelihood of exposure as a function of sequence, as determined by the collective coordinates method.

Table 1 shows the peak values of the dihedral angle distribution for those dihedral angles whose distributions show significant differences between the cyclic peptide and other species.

Table 2 shows peak values of the Ramachandran backbone phi/psi angle distributions.

Table 3 gives the Ramachandran backbone dihedral angles as well as the side chain dihedral angles for the cyclic peptide that is the centroid conformation of the largest conformational cluster, and for the centroid conformation of the largest cluster taken from the linear peptide ensemble.

Table 4 is a table of mean curvature values for each residue in the cyclic, linear, and 2M4J fibril ensembles.

Table 5 shows the binding properties of selected antibodies.

Table 6 shows the binding properties summary for selected antibodies.

Table 7 lists the oligomer binding-monomer binding for an antibody raised against cyclo(CGHDSGG) (SEQ ID NO:2).

Table 8 lists properties of antibodies tested on formalin fixed tissues.

Table 9 is an exemplary toxicity assay.

Table 10 lists CDR sequences.

Table 11 lists heavy chain and light chain variable sequences.

Table 12 is a table of A-beta epitope sequences and select sequences with linker.

Table 13 provides the full A-beta 1-42 human polypeptide sequence.

DETAILED DESCRIPTION OF THE DISCLOSURE

Provided herein are antibodies, immunotherapeutic compositions and methods which may target epitopes preferentially accessible in toxic oligomeric species of A-beta, including oligomeric species associated with Alzheimer's disease. A region in A-beta has been identified that may be specifically and/or selectively accessible to antibody binding in oligomeric species of A-beta.

As demonstrated herein, generation of oligomer-specific or oligomer selective antibodies was accomplished through the identification of targets on A-beta peptide that are not present, or present to a lesser degree, on either the monomer and/or fibril. Oligomer-specific epitopes need not differ in primary sequence from the corresponding segment in the monomer or fibril, however they would be conformationally distinct in the context of the oligomer. That is, they would present a distinct conformation in terms of backbone and/or side-chain orientation in the oligomer that would not be present (or would be unfavourable) in the monomer and/or fibril.

Antibodies raised to linear peptide regions may not be selective for oligomer, and thus may bind to monomer or A-beta plaques as well.

As described herein, to develop antibodies that may be selective for oligomeric forms of A-beta, the inventors sought to identify regions of A-beta sequence that are prone to disruption in the context of the fibril, and that may be exposed on the surface of the oligomer.

As described the Examples, the inventors have identified a region they have determined to be prone to disruption in the context of the fibril. The inventors designed cyclic compounds comprising the identified target region to satisfy criteria of an alternate conformation such as higher curvature, higher exposed surface area, alternative dihedral angle distributions, and/or did not readily align by root mean squared deviation (RMSD) to either the linear or fibril ensembles.

Antibodies could be raised using a cyclic peptide comprising the target region, that selectively bound the cyclic peptide compared to a linear peptide of the same sequence (e.g. corresponding linear sequence). Experimental results are described and identify epitope-specific and conformationally selective antibodies that bind synthetic oligomer selectively compared to synthetic monomers, bind CSF from AD patients preferentially over control CSF and/or bind soluble brain extract from AD patients preferentially over control soluble brain extract. Further staining of AD brain tissue identified antibodies that show no or negligible plaque binding and in vitro studies found that the antibodies inhibited Aβ oligomer propagation and aggregation.

I. Definitions

As used herein, the term 'A-beta' may alternately be referred to as 'amyloid beta', 'amyloid β', Abeta, A-beta or 'Aβ'. Amyloid beta is a peptide of 36-43 amino acids and includes all wildtype and mutant forms of all species, particularly human A-beta. A-beta40 refers to the 40 amino acid form; A-beta42 refers to the 42 amino acid form, etc. The amino acid sequence of human wildtype A-beta42 is shown in SEQ ID NO: 3

As used herein, the term "A-beta monomer" herein refers to any of the individual subunit forms of the A-beta (e.g. 1-40, 1-42, 1-43) peptide.

As used herein, the term "A-beta oligomer" herein refers to a plurality of any of the A-beta subunits wherein several (e.g. at least two) A-beta monomers are non-covalently aggregated in a conformationally-flexible, partially-ordered, three-dimensional globule of less than about 100, or more typically less than about 50 monomers. For example, an oligomer may contain 3 or 4 or 5 or more monomers. The term "A-beta oligomer" as used herein includes both synthetic A-beta oligomer and/or native A-beta oligomer. "Native A-beta oligomer" refers to A-beta oligomer formed in vivo, for example in the brain and CSF of a subject with AD.

As used herein, the term "A-beta fibril" refers to a molecular structure that comprises assemblies of non-covalently associated, individual A-beta peptides which show fibrillar structure under an electron microscope. The fibrillar structure is typically a "cross beta" structure; there is no theoretical upper limit on the size of multimers, and fibrils may comprise thousands or many thousands of monomers. Fibrils can aggregate by the thousands to form senile plaques, one of the primary pathological morphologies diagnostic of AD.

The term "HDSG" means the amino acid sequence histidine, aspartic acid, serine, and glycine as shown in SEQ ID NO: 1. Similarly DSG, DSGG (SEQ ID NO:3), HDSGYE (SEQ ID NO:11), HDSGY (SEQ ID NO:4), RHDSG (SEQ ID NO:5), RHDS (SEQ ID NO:6) refer to the amino acid sequence identified by the 1-letter amino acid code. Depending on the context, the reference of the amino acid sequence can refer to a sequence in A-beta or an isolated peptide, such as the amino acid sequence of a cyclic compound.

Figure 2:
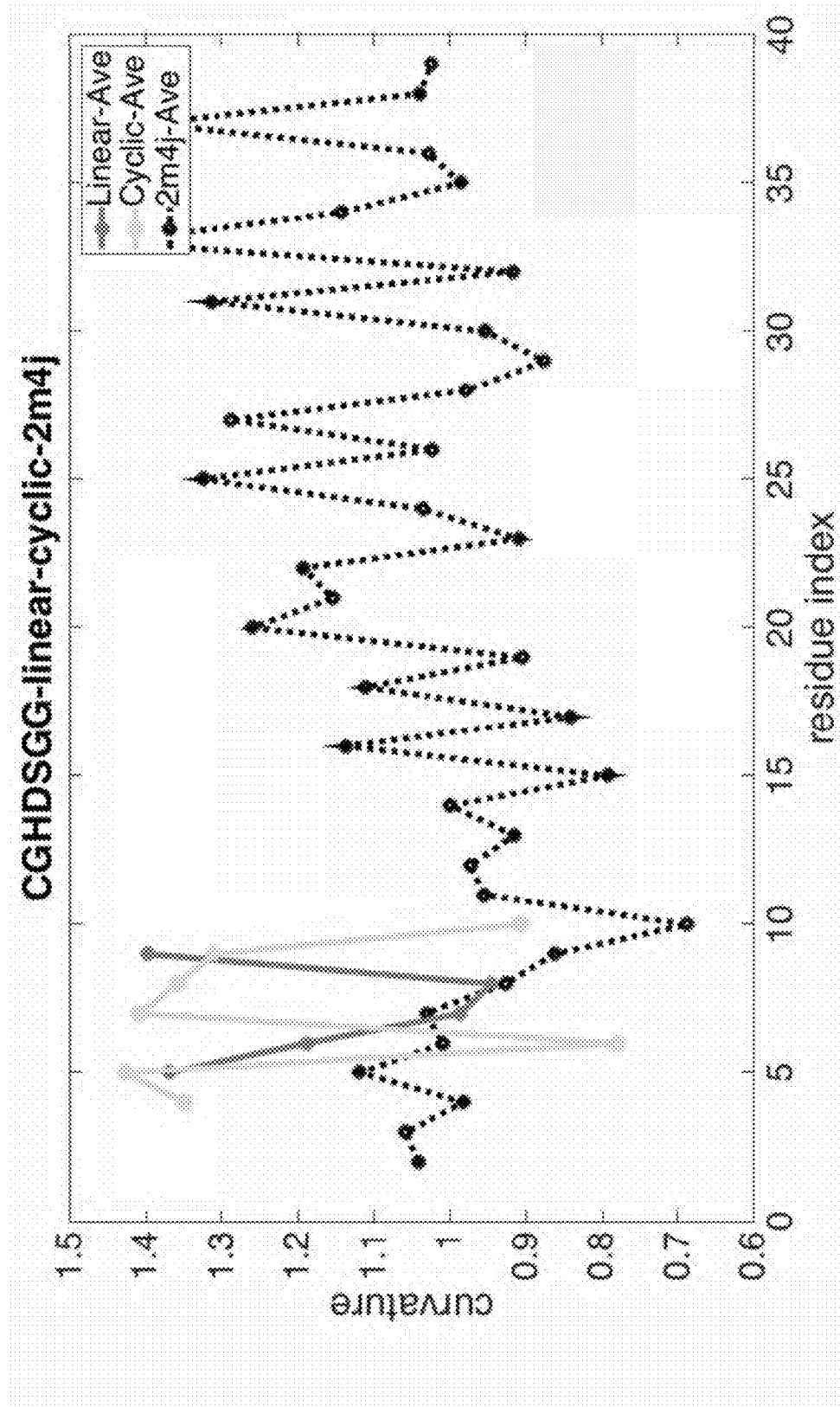
FIG. 2: Curvature as a function of residue index. Mean curvature in the equilibrium ensemble for the cyclic peptide CGHDSGG (SEQ ID No: 2) is shown (solid light grey), along with the curvature for the linear peptide (solid dark grey), and the curvature of the various monomers in the fibril (dotted line).
Figure 3:
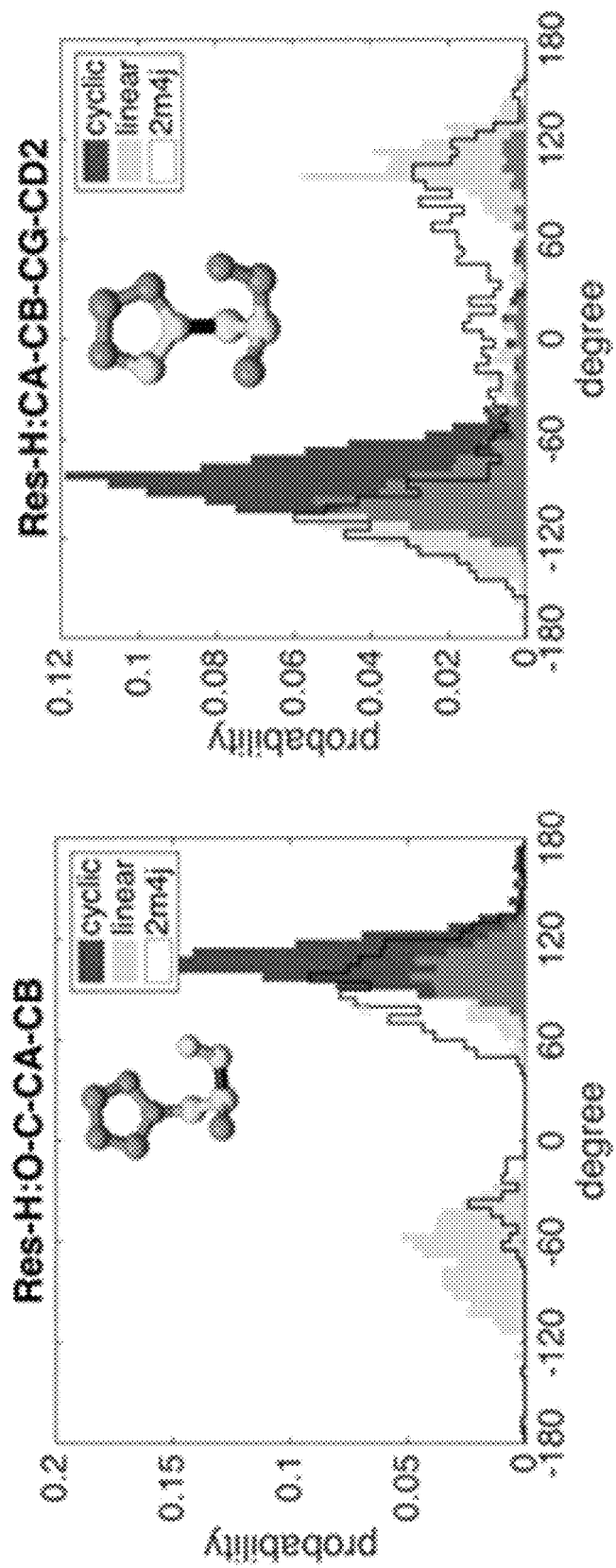
FIG. 3: Dihedral angle distributions for the side chain heavy atoms of H6. Schematics of residue H6 are shown in the insets; the corresponding bond over which the dihedral angle is taken is rendered darker than the other bonds, and the four atoms defining the dihedral angle are shown in lighter gray. The angles corresponding to the peak values of the dihedral distributions for all 3 species—linear peptide, cyclic peptide, and (2M4J) fibril ensemble are provided in Table 1. The differences between the peak values are also provided in Table 1. The dihedral angle distribution for the fibril ensemble is taken over all 9 chains of A-beta42 in the PDB structure in the fibril, so the dihedral distribution observed is generally broader than the distribution for any single chain taken from the structure 2M4J.
Figure 3:
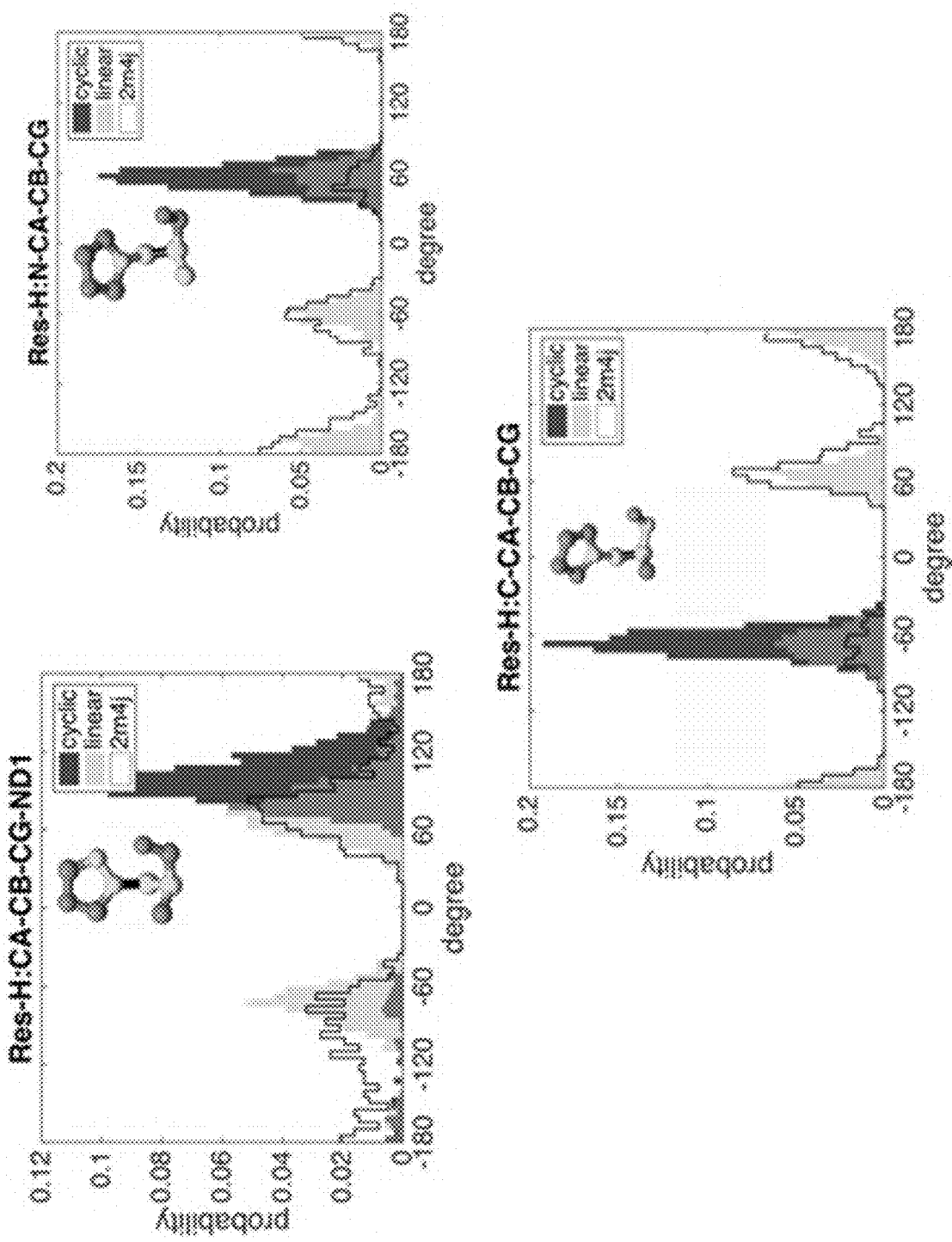
Figure 4:
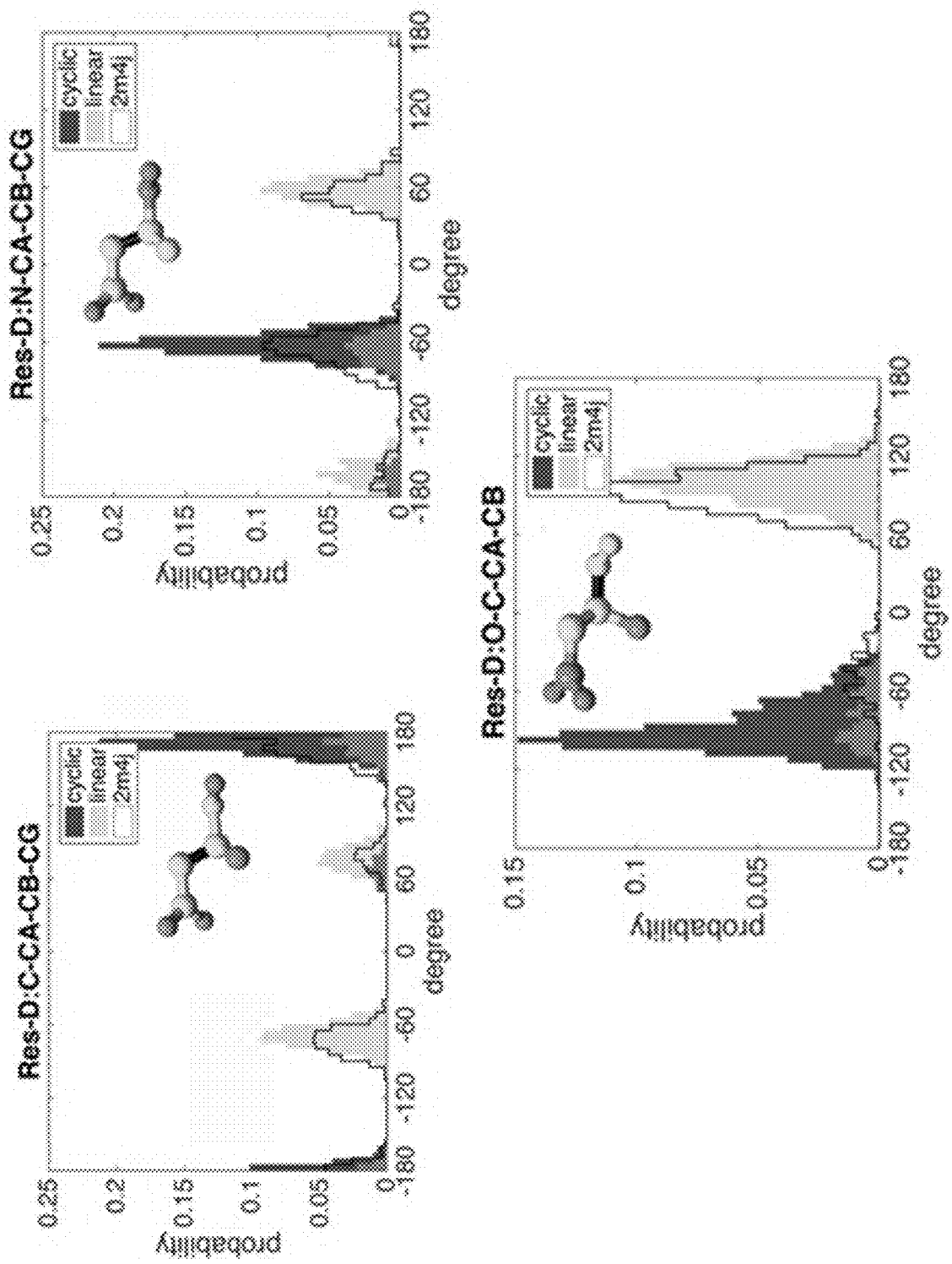
FIG. 4: Dihedral angle distribution for the angle O-C-Cα-Cβ involving the side chain heavy atoms of residue D7. Schematics of D7 are shown in the insets; the corresponding bond over which the dihedral angle is taken is rendered darker than the other bonds. The values are provided in Table 1.
Figure 5:
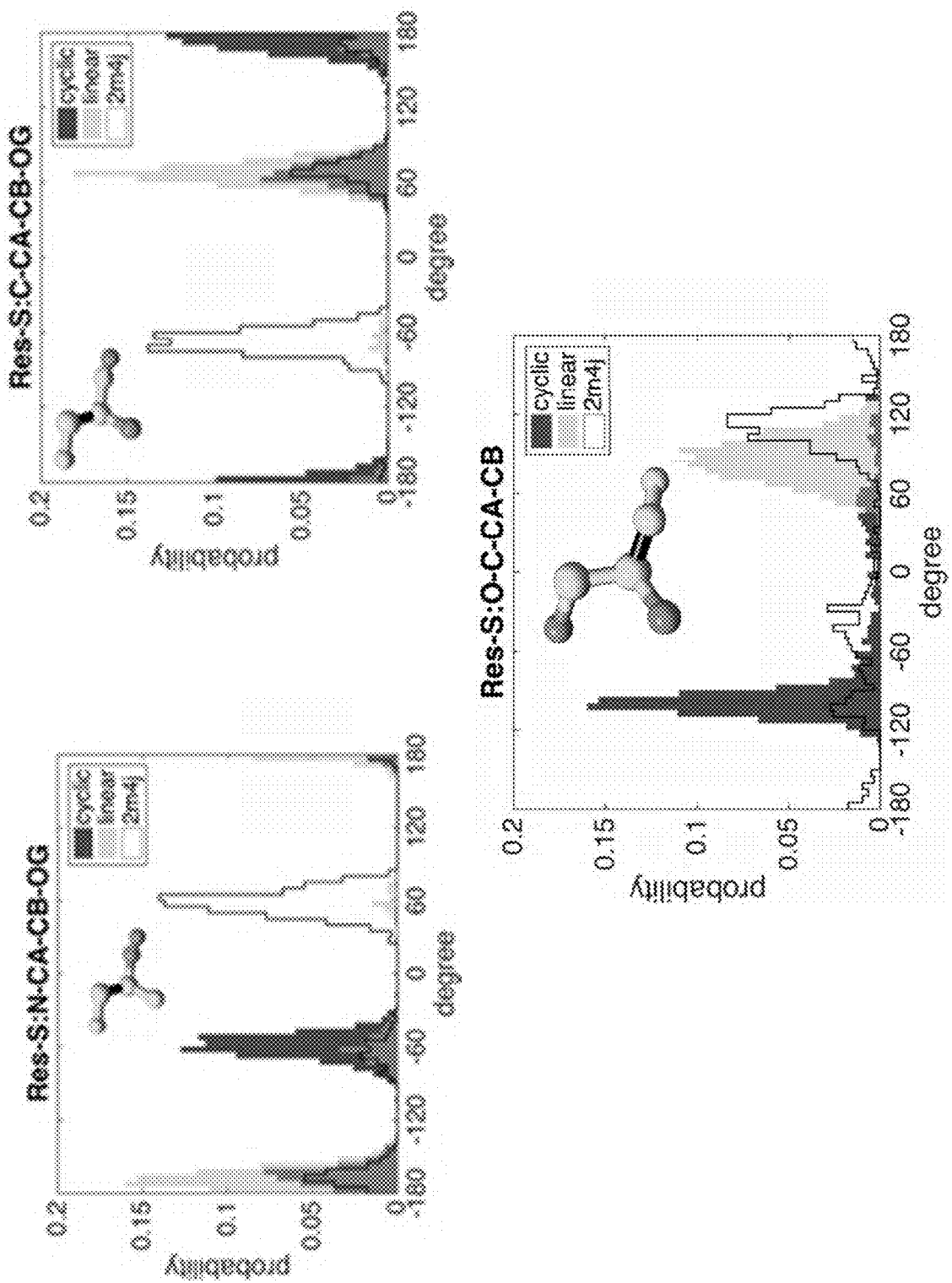
FIG. 5: Dihedral angle distributions for angles involving the side chain heavy atoms of S8. Schematics of S8 are shown in the insets; the corresponding bond over which the dihedral angle is taken is rendered darker than the other bonds. The values are provided in Table 1.
Figure 6:
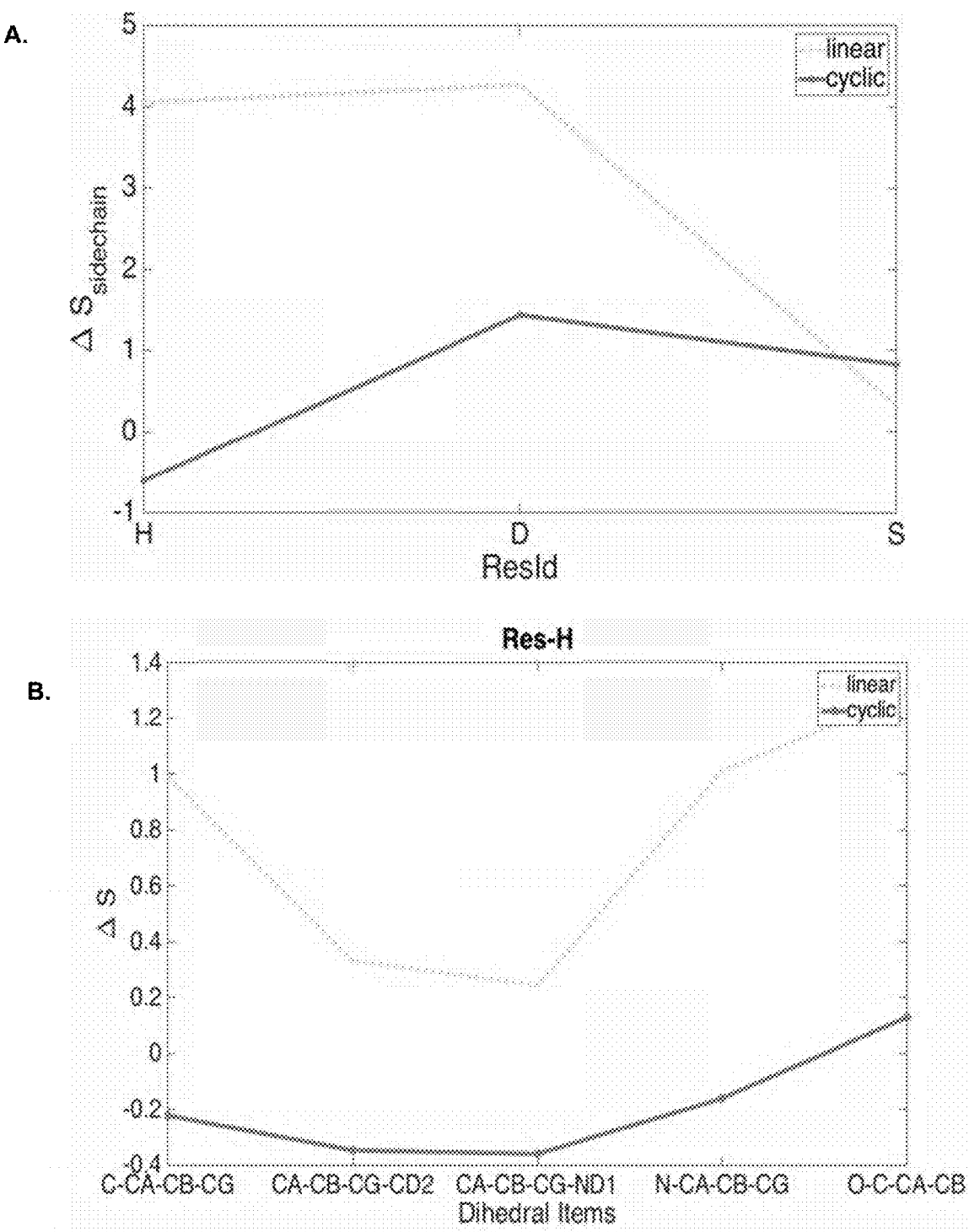
FIG. 6: Top panel (A): Side chain entropy change of the linear and cyclic peptides relative to the entropy in the fibril, plotted for each residue H, D, and S. (B) $2^{nd}$ from top panel: entropy of the individual dihedral angles in H6. Note for example that CA-CB-CG-ND1 has substantially less entropy than either the fibril or linear peptides, which can also be seen by the more sharply peaked dihedral angle distribution for this particular dihedral in FIG. 3. (C) $2^{nd}$ from bottom panel: entropy of individual dihedral angles in D7. (D) Bottom panel: entropy of individual dihedral angles in S8.
Figure 6:
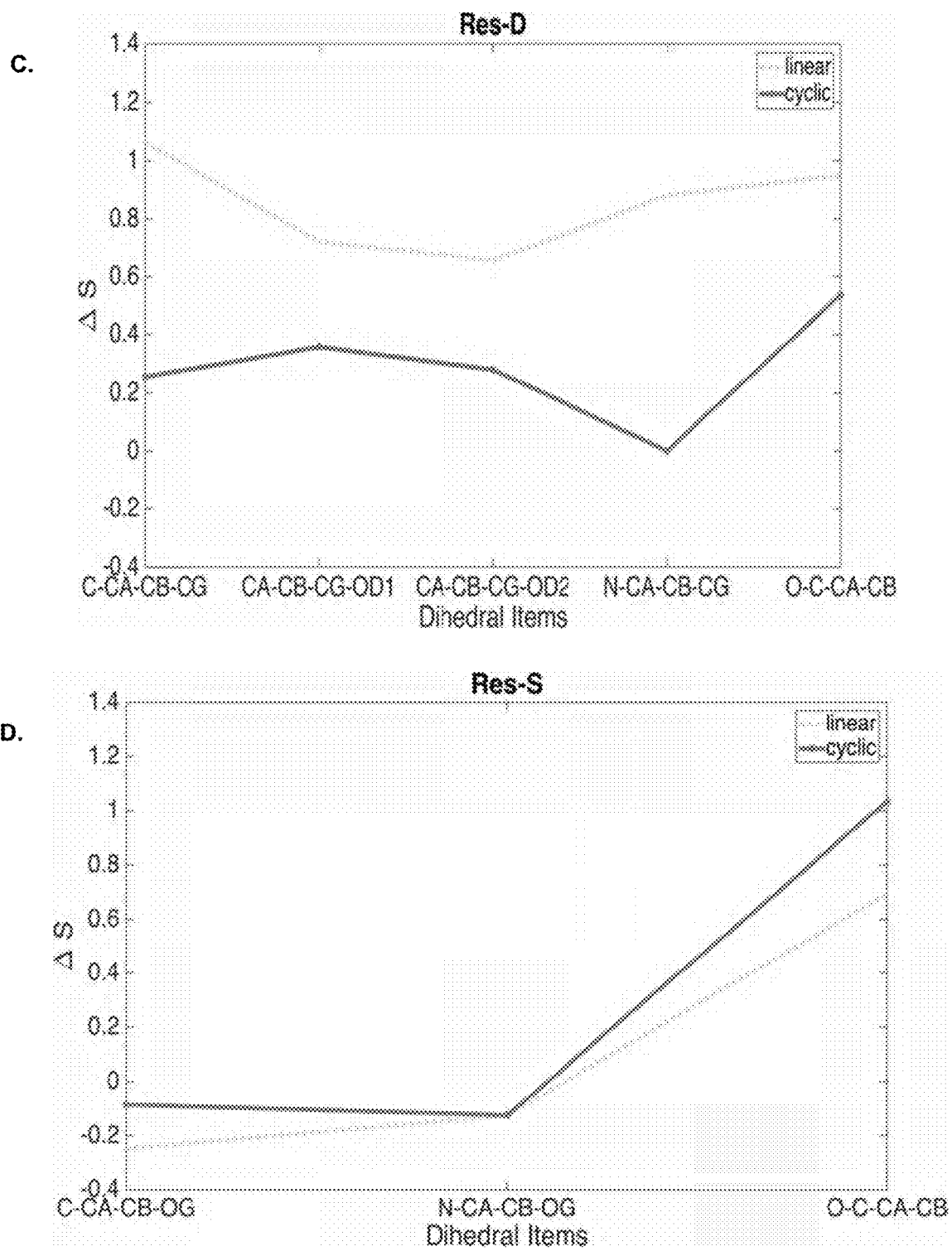
Figure 7:
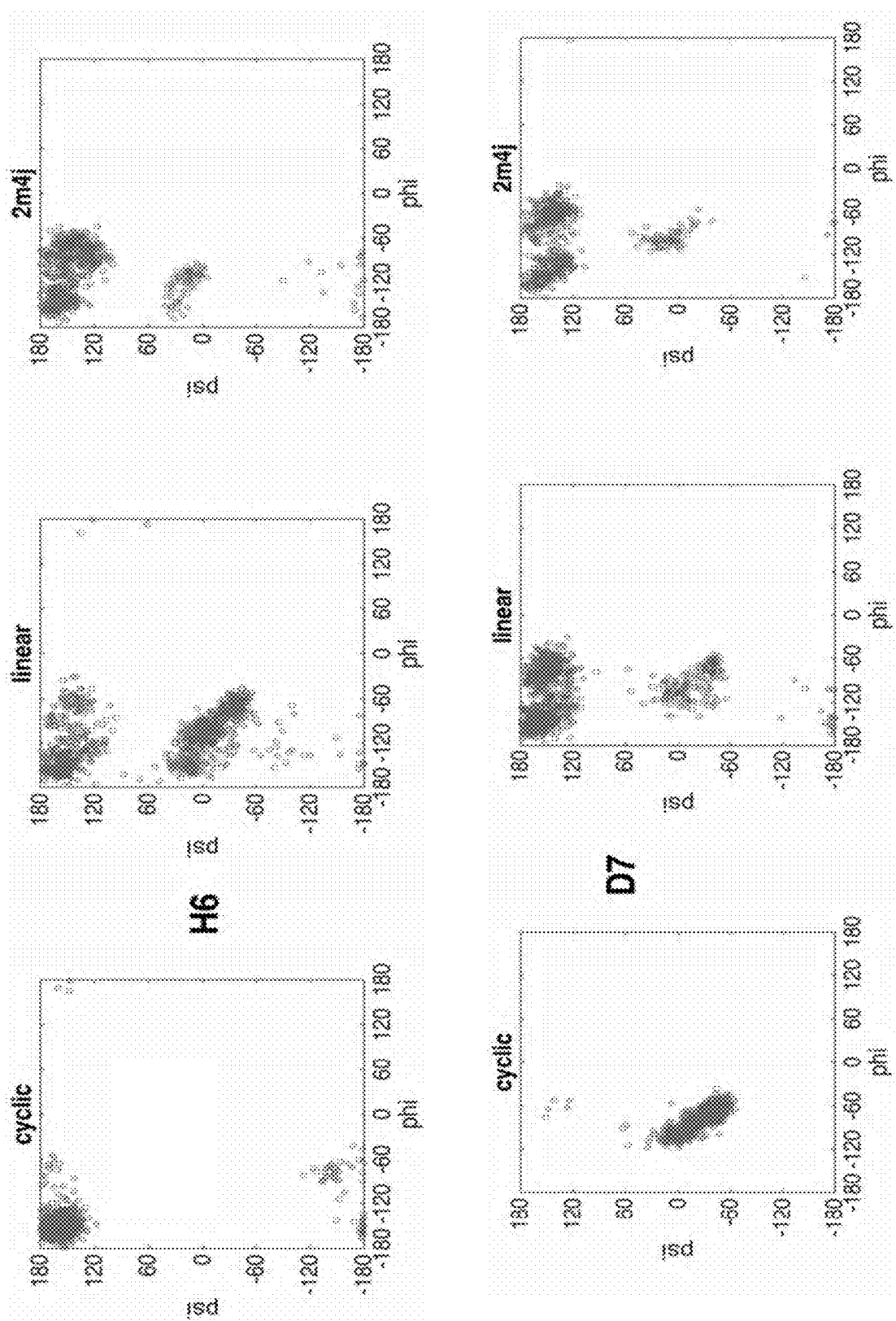
FIG. 7: Equilibrium backbone Ramachandran angles for residues H, D, S, and G, in both the linear and cyclic forms of the peptide CGHDSGG (SEQ ID NO: 2), along with the backbone Ramachandran angles for the residues H, D, S, and G in the context of the fibril 2M4J.
Figure 7:
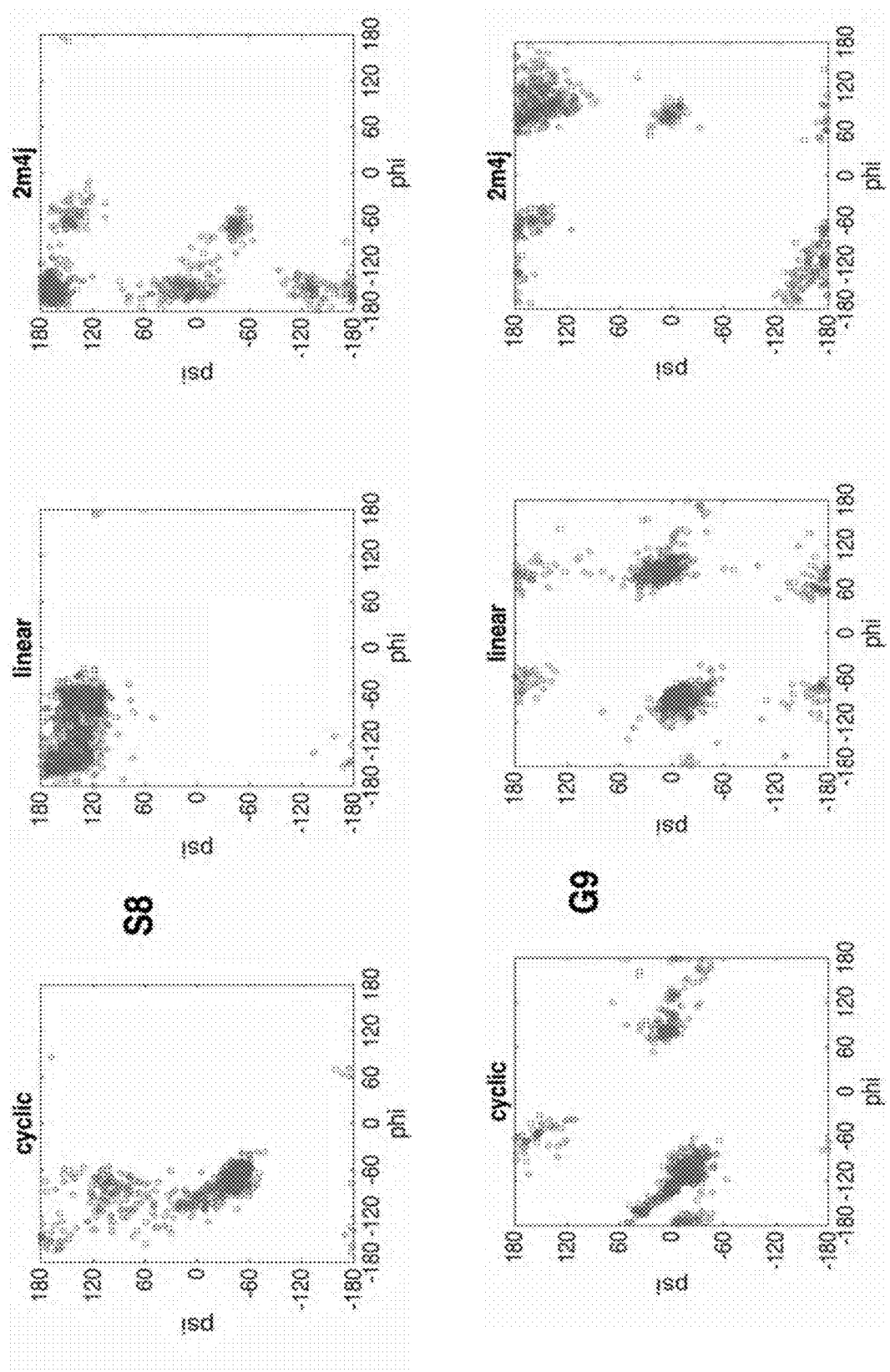
Figure 8:
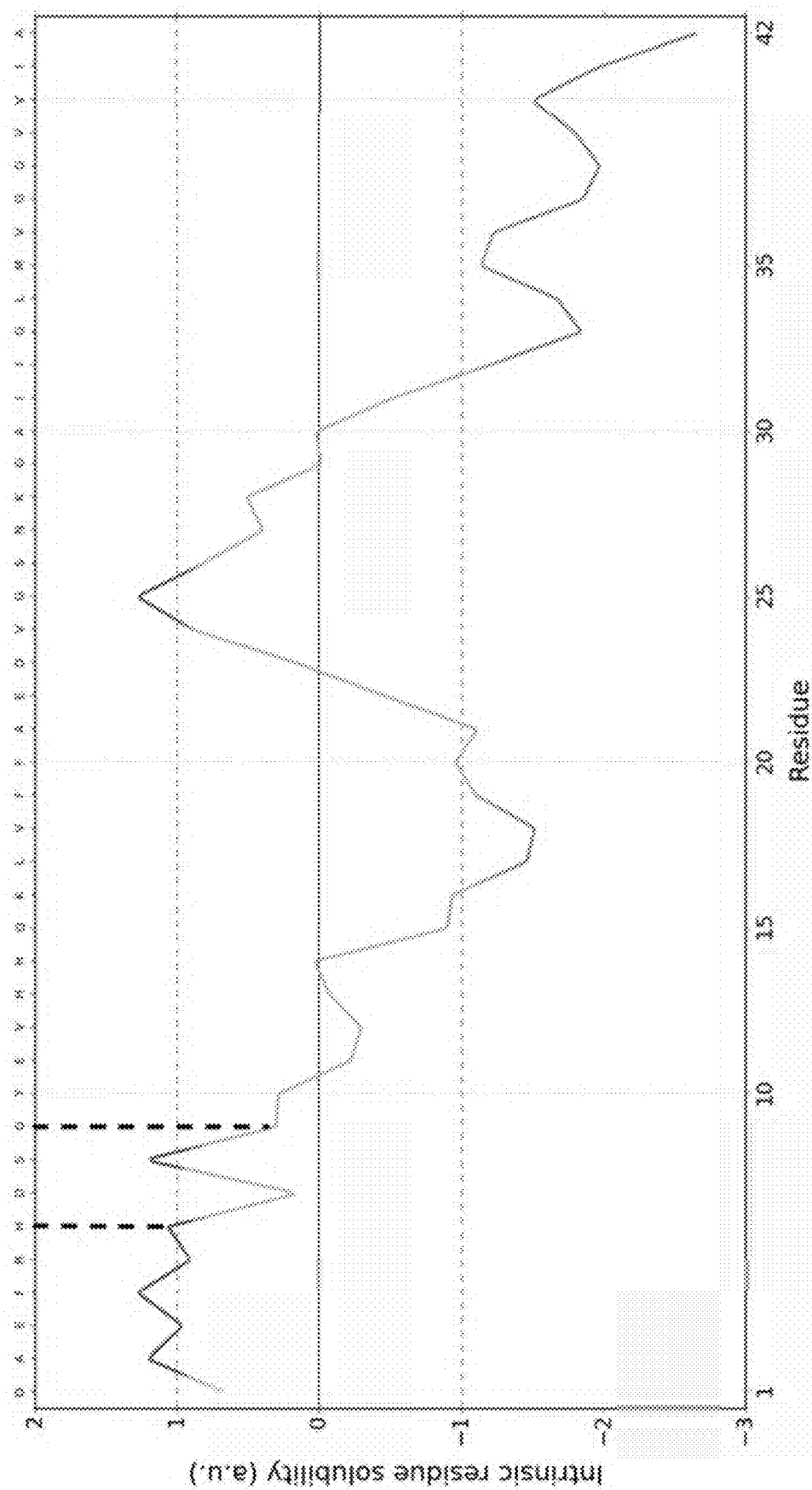
FIG. 8: Solubility vs residue index for A-beta42 peptide. HDSG (SEQ ID NO: 1) has values of +1.1, +0.14, +1.2, and +0.30 respectively.
Figure 9:
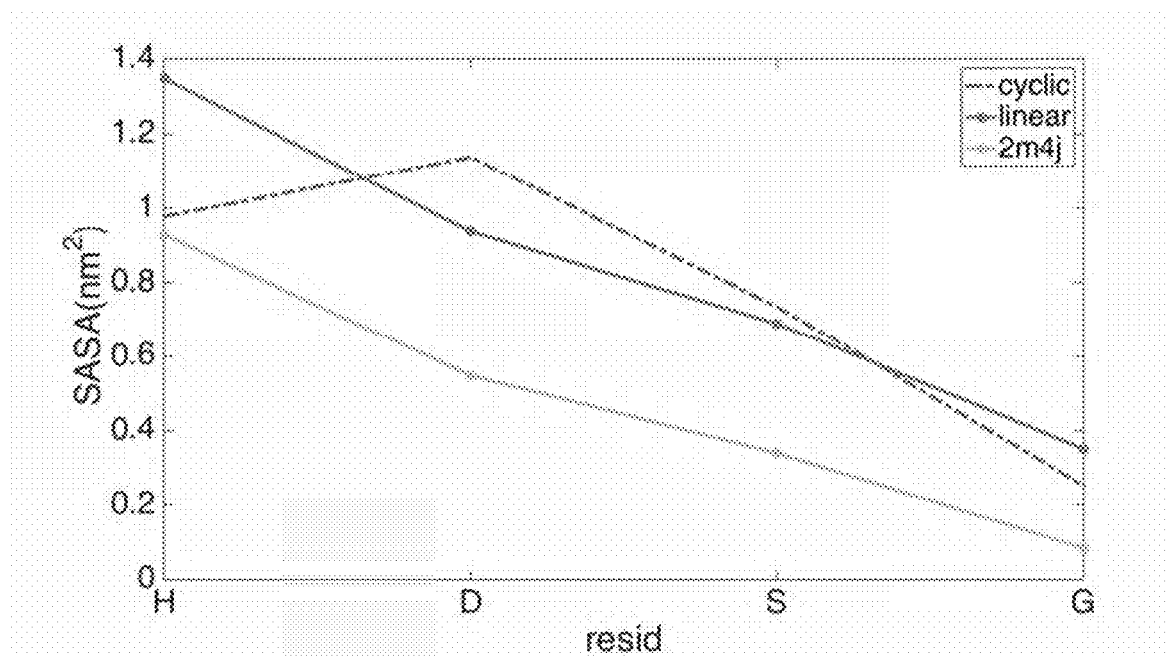
FIG. 9: Plots of the solvent accessible surface area (SASA), the weighted SASA, $((s_i - <s>)/\delta s) \cdot SASA_i$, and $((s_i - <s>)/\delta s) \cdot SASA_i - (((s_i - <s>)/\delta s) \cdot SASA_i)_{fibril}$.
Figure 9:
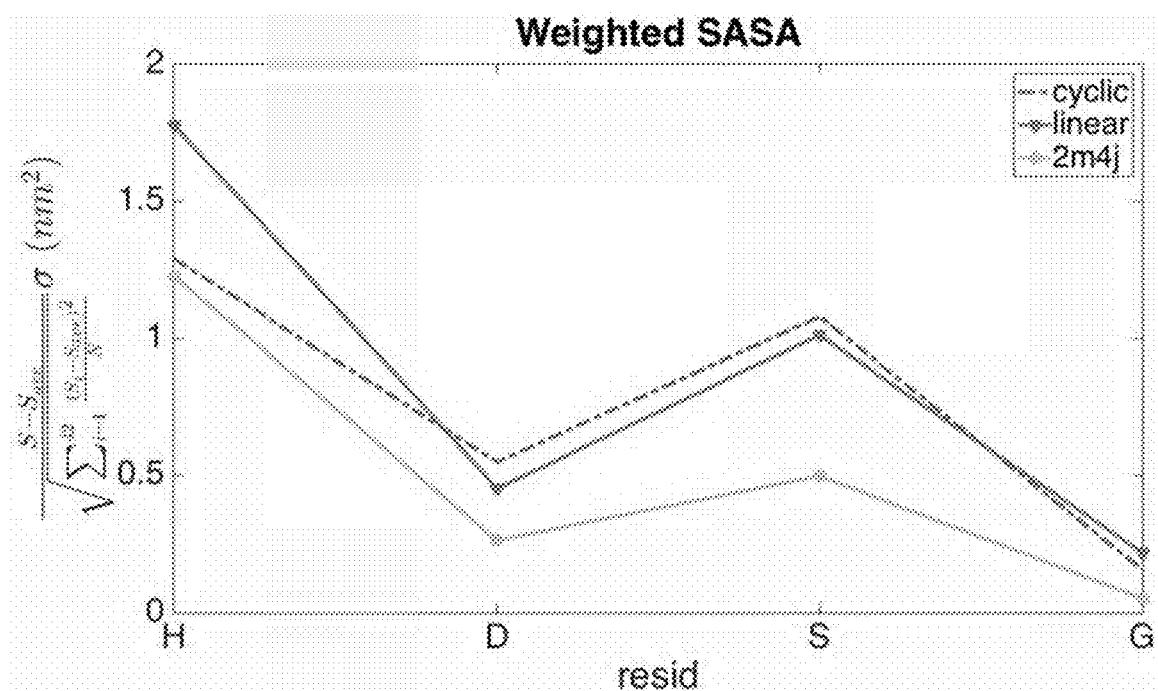
Figure 9:
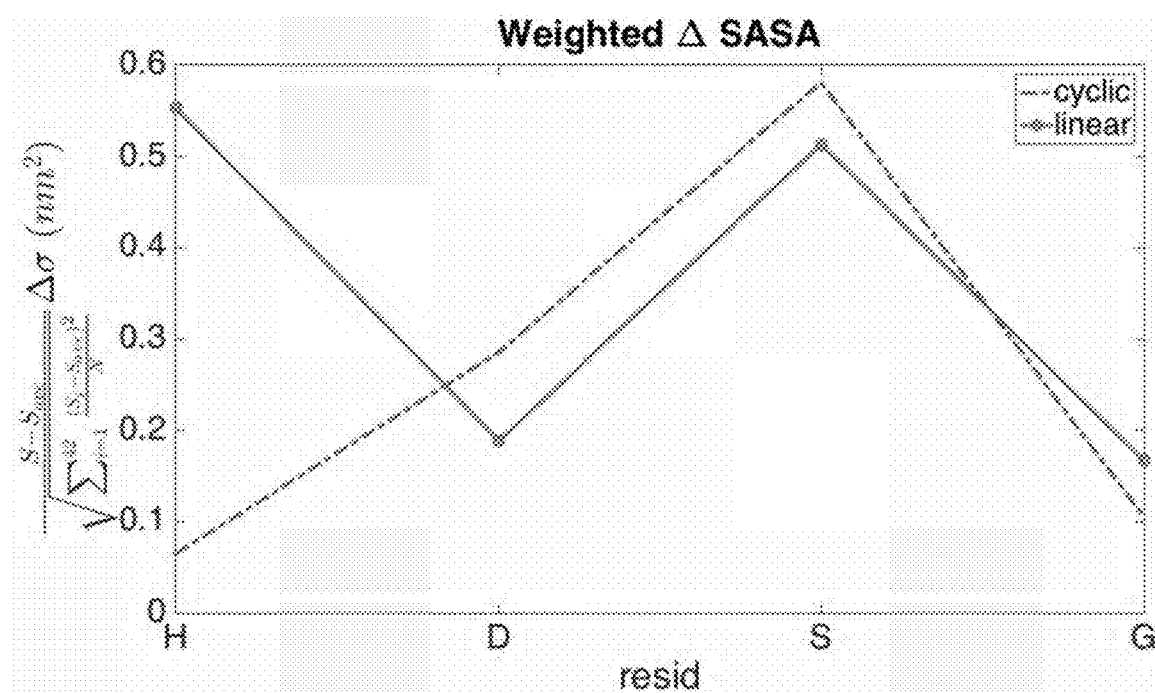
Figure 10:
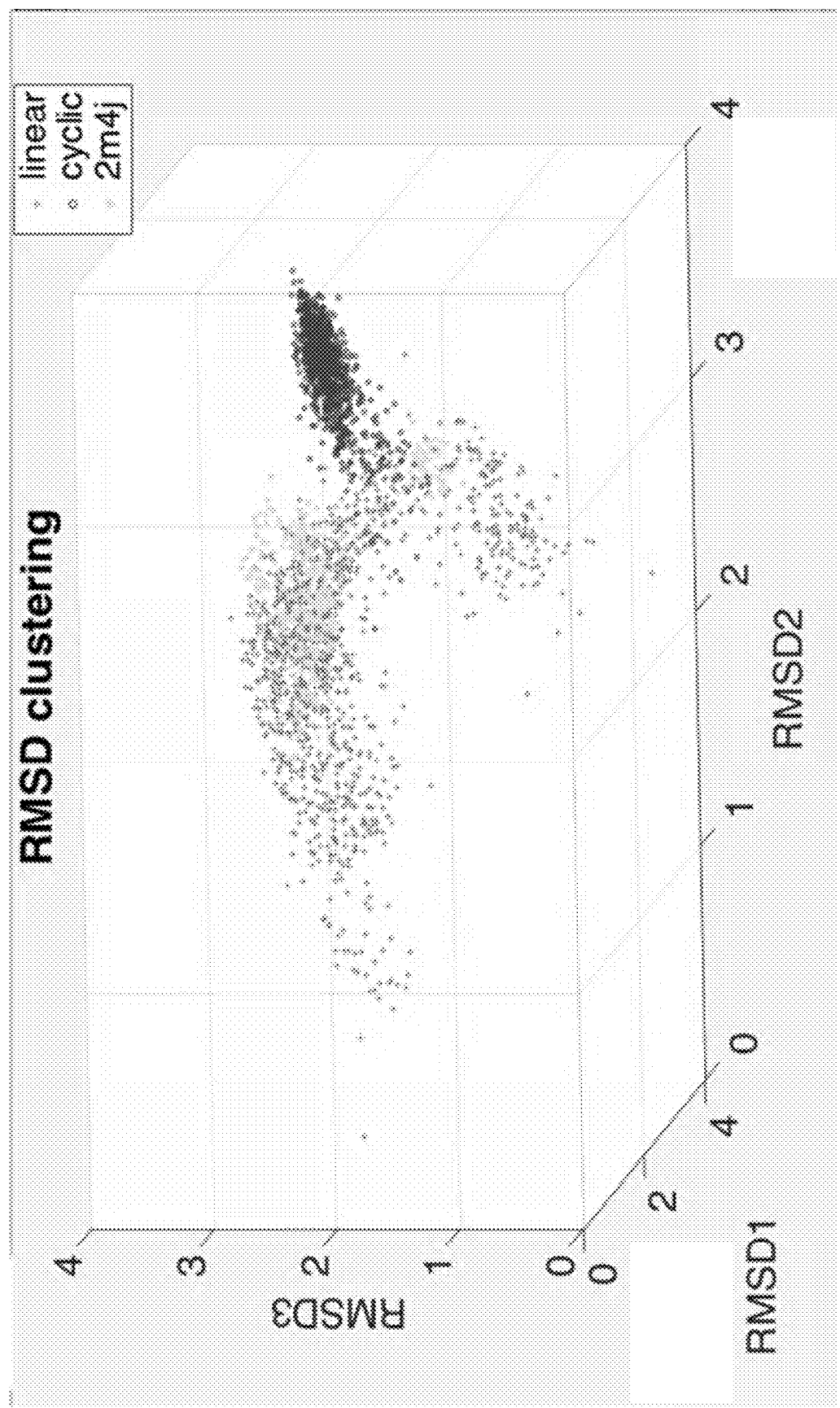
FIG. 10: Two separate views of the root mean squared deviation (RMSD) values to the centroids of the three largest clusters of the linear peptide ensemble. Each point corresponds to a given conformation taken from the linear peptide, cyclic peptide, or fibril equilibrium ensembles.
Figure 10:
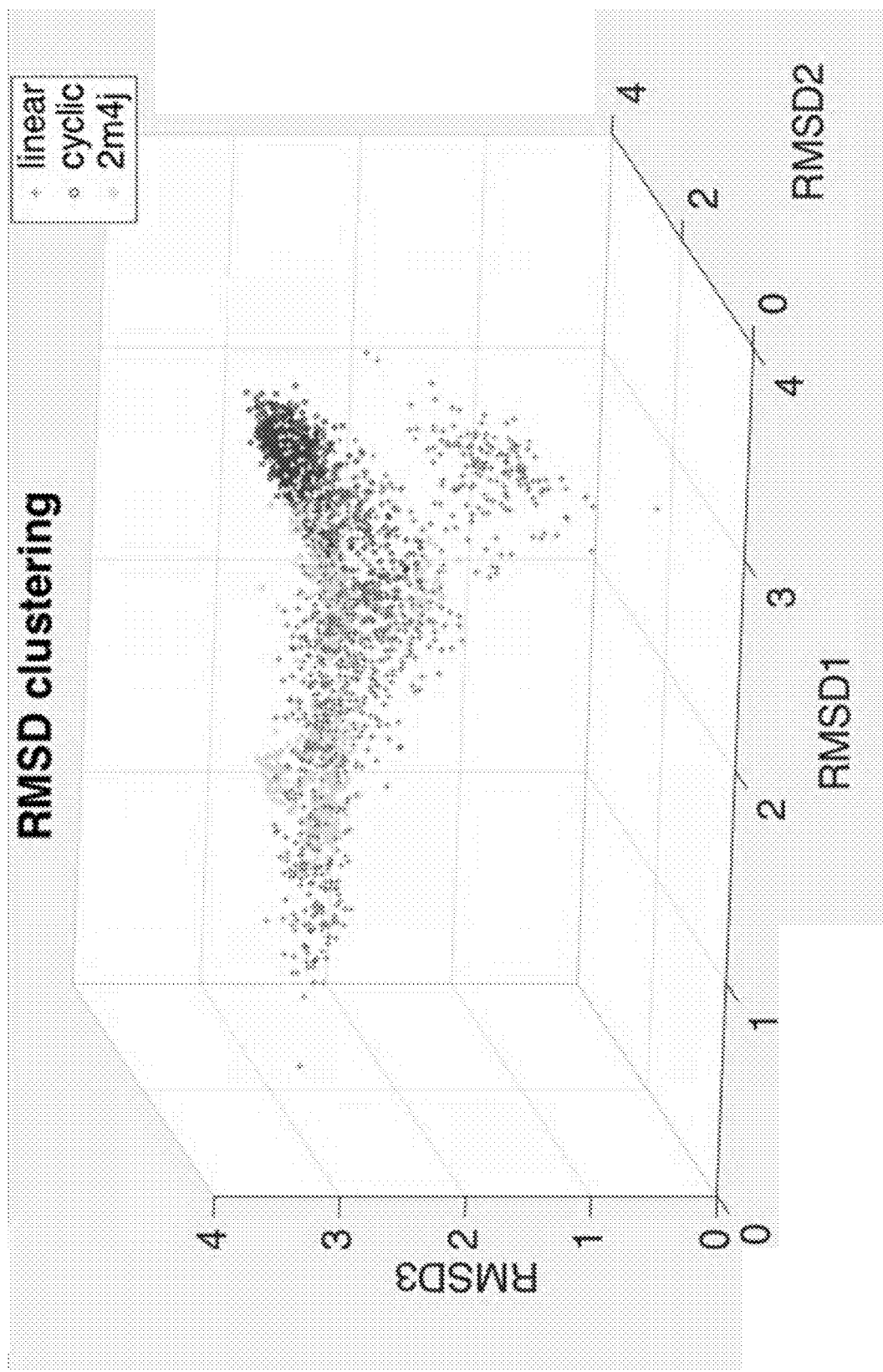
Figure 11:
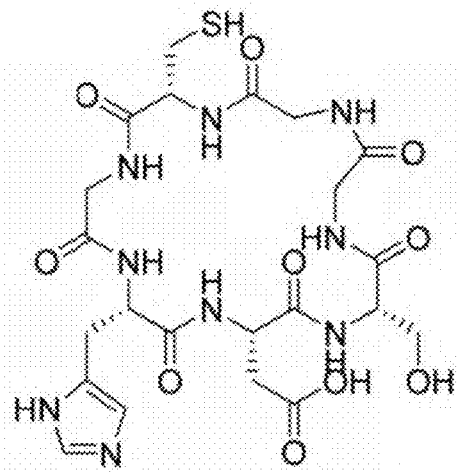
FIG. 11 B: Schematic representations of cyclic peptides comprising HDSG (SEQ ID NO: 1), including the cyclic peptide with circular peptide bond, the cyclic peptide with PEG2 linker between the G and C residues, and the cyclic peptide with PEG2 linker between the C and H residues.
Figure 11:
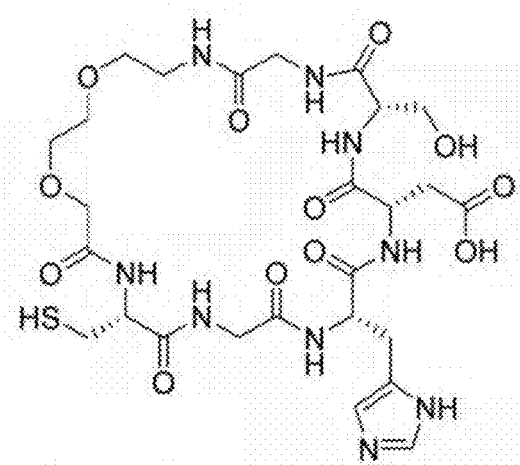
Figure 11:
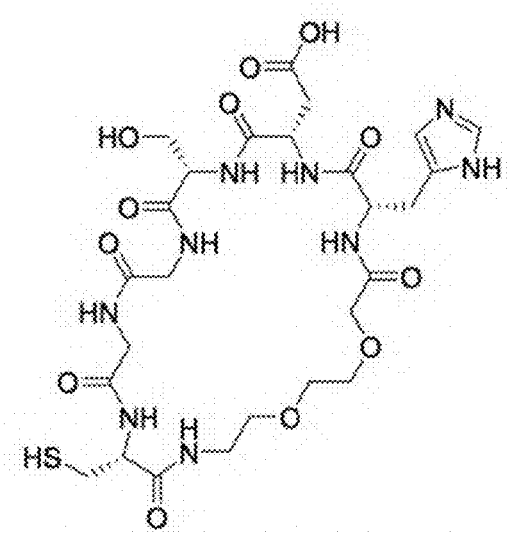

The term "alternate conformation than occupied by an amino acid residue (e.g. H, D, S and/or G) in the linear compound, monomer and/or fibril" as used herein means having one or more differing conformational properties selected from solvent accessibility, entropy, curvature (e.g. in the context of peptide HDSG (SEQ ID NO:1) as compared to for example in the cyclic peptide described in the Examples), RMSD structural alignment, and dihedral angle of one or more backbone or side chain dihedral angles compared to said property for H, D and/or S in an A-beta linear compound comprising the residue in context, A-beta monomer and/or A-beta fibril structures as shown for example in PDBs 2M4J, 2MXU, 2LMN, or 2LMP and shown in FIGS. 1-12 and/or in the Tables. For example, FIG. 2 and Table 4 show that the curvature of HDSG (SEQ ID NO:1), for the cyclic peptide ensemble is significantly larger than the curvature of HDSG (SEQ ID NO:1), in the ensemble of fibril conformations. This is particularly evident for D7, S8, and G9. Moreover for D7 and S8, the curvature in the cyclic peptide ensemble is substantially higher than that in the linear peptide ensemble. This implies conformational selectivity may be particularly conferred by residues D7 and S8. The last two panels of FIG. 3 show that the dihedral angle distribution for the angles (N-CA-CB-CG) and (C-CA-CB-CG) for H6 in the cyclic peptide ensemble do have overlap, but are not the most common angles in the linear peptide and fibril ensembles (the probabilities are 36% and 13% respectively for N-CA-CB-CG in linear and fibril and 36% and 13% respectively for C-CA-CB-CG in the linear and fibril). The last panel of FIG. 4 shows that the dihedral angle distribution for angle (O-C-CA-CB) involving the side chain of residue D7 reflects an alternate conformational distribution compared to either the monomer or fibril. FIG. 5 shows that the dihedral angle distributions for angles (N-CA-CB-OG), (C-CA-CB-OG), and (O-C-CA-CB) involving the side chain of residue S8 reflects an alternate conformational distribution compared to either the monomer or fibril. The alternate conformation can be similarly, less or more "constrained" than the comparator conformation. For example, FIG. 6 demonstrates that H6 is more constrained in the cyclic peptide then it is in either the fibril or the monomer. Residue D7 is more constrained in the cyclic peptide ensemble then it is in the monomer, but less than it is in the fibril. Residue S8 is less constrained in the cyclic peptide ensemble then it is in the fibril and also marginally less than it is in the monomer. FIG. 7 demonstrates that the distributions of the Ramachandran dihedral angles for the backbone of cyclic peptides are substantially different than those for either monomer or fibril for residues D7 and S8. FIG. 8 shows that the residues HDSG (SEQ ID NO:1) have a larger solubility than the average solubility present in A-beta peptide, indicating the likelihood of exposure of these residues in an oligomeric ensemble of conformations. FIG. 9 shows that residues HDSG (SEQ ID NO:1) have increased solvent accessible surface area, SASA, compared to the fibril, and that, when weighted by solubility, all residues in the cyclic peptide ensemble show an increase in weighted SASA over that in the fibril, with residue S8 showing substantial increase in weighted SASA over the fibril. FIG. 10 shows that the cyclic peptide equilibrium structures of HDSG (SEQ ID NO:1) cluster differently than the equilibrium structures of either the linear peptide or corresponding sequence in the fibril, while the linear and fibril ensembles are not clearly differentiated.

The term "amino acid" includes all of the naturally occurring amino acids as well as modified L-amino acids. The atoms of the amino acid can include different isotopes. For example, the amino acids can comprise deuterium substituted for hydrogen nitrogen-15 substituted for nitrogen-14, and carbon-13 substituted for carbon-12 and other similar changes.

The term "antibody" as used herein is intended to include, monoclonal antibodies, polyclonal antibodies, single chain, veneered, humanized and other chimeric antibodies and binding fragments thereof, including for example a single chain Fab fragment, Fab'2 fragment or single chain Fv fragment. The antibody may be from recombinant sources and/or produced in animals such as rabbits, llamas, sharks etc. Also included are human antibodies that can be produced in transgenic animals or using biochemical techniques or can be isolated from a library such as a phage library. Humanized or other chimeric antibodies may include sequences from one or more than one isotype or class or species.

The phrase "isolated antibody" refers to antibody produced in vivo or in vitro that has been removed from the source that produced the antibody, for example, an animal, hybridoma or other cell line (such as recombinant insect, yeast or bacteria cells that produce antibody). The isolated antibody is optionally "purified", which means at least: 80%, 85%, 90%, 95%, 98% or 99% purity.

The term "binding fragment" as used herein to a part or portion of an antibody or antibody chain comprising fewer amino acid residues than an intact or complete antibody or antibody chain and which binds the antigen or competes with intact antibody. Exemplary binding fragments include without limitations Fab, Fab', F(ab')2, scFv, dsFv, ds-scFv, dimers, nanobodies, minibodies, diabodies, and multimers thereof. Fragments can be obtained via chemical or enzymatic treatment of an intact or complete antibody or antibody chain. Fragments can also be obtained by recombinant means. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, dsFv, ds-scFv, dimers, minibodies, diabodies, bispecific antibody fragments and other fragments can also be constructed by recombinant expression techniques.

The terms "IMGT numbering" or "ImMunoGeneTics database numbering", which are recognized in the art, refer to a system of numbering amino acid residues which are more variable (i.e. hypervariable) than other amino acid residues in the heavy and light chain variable regions of an antibody, or antigen binding portion thereof.

When an antibody is said to specifically bind to an epitope such as HDSG (SEQ ID NO:1), what is meant is that the antibody specifically binds to a peptide containing the specified residues or a part thereof for example at least 2 residues of HDSG, with a minimum affinity, and does not bind an unrelated sequence or unrelated sequence spatial orientation greater than for example an isotype control antibody. Such an antibody does not necessarily contact each residue of HDSG (SEQ ID NO:1) and every single amino acid substitution or deletion within said epitope does not necessarily significantly affect and/or equally affect binding affinity.

When an antibody is said to selectively bind an epitope such as a conformational epitope, such as HDSG (SEQ ID NO:1), what is meant is that the antibody preferentially binds one or more particular conformations containing the specified residues or a part thereof with greater affinity than it binds said residues in another conformation. For example, when an antibody is said to selectively bind a cyclopeptide comprising HDSG or related epitope relative to a corresponding linear peptide, the antibody binds the cyclopeptide with at least a 2 fold greater affinity than it binds the linear peptide.

As used herein, the term "conformational epitope" refers to an epitope where the epitope amino acid sequence has a particular three-dimensional structure wherein at least an aspect of the three-dimensional structure not present or less likely to be present in a corresponding linear peptide is specifically and/or selectively recognized by the cognate antibody. The epitope e.g. HDSG (SEQ ID NO: 1) may be partially or completely exposed on the molecular surface of oligomeric A-beta and partially or completely obscured from antibody recognition in monomeric or fibrillar plaque A-beta. Antibodies which specifically and/or selectively bind a conformation-specific epitope recognize the spatial arrangement of one or more of the amino acids of that conformation-specific/selective epitope. For example an HDSG (SEQ ID NO: 1) conformational epitope, refers to an epitope of HDSG (SEQ ID NO: 1) that is recognized by antibodies specifically and/or selectively, for example at least 2 fold, 3 fold, 5 fold, 10 fold, 50 fold, 100 fold, 250 fold, 500 fold or 1000 fold or greater, more selectively as compared to linear HDSG (SEQ ID NO: 1).

The term "related epitope" as used herein means at least two residues of HDSG (SEQ ID NO:1) that are antigenic and/or sequences comprising 1 or 2 amino acid residues in a A-beta either N-terminal or C-terminal to at least two residues of HDSG (SEQ ID NO: 1). For example it is shown herein HDSG (SEQ ID NO:1), HDSGY (SEQ ID NO:4) and RHDSG (SEQ ID NO:5) were identified as regions prone to disorder in an A-beta fibril. HDSGY (SEQ ID NO:4) and RHDSG (SEQ ID NO:5) are accordingly related epitopes. Further it is demonstrated through modelling that residues D7 and S8 in particular exhibit differences in the cyclic compound compared to the corresponding linear sequence, accordingly DS, HDS, DSG, DSGY (SEQ ID NO: 13) and RHDS (SEQ ID NO:6) are related epitopes. Exemplary related epitopes can include A-beta sequences included in Table 12.

The term "constrained conformation" as used herein with respect to an amino acid or a side chain thereof, within a sequence of amino acids (e.g. H or D in HDSG (SEQ ID NO: 1)), or with respect to a sequence of amino acids in a larger polypeptide, means decreased rotational mobility of the amino acid dihedral angles, relative to a corresponding linear peptide sequence, or the sequence or larger polypeptide, resulting in a decrease in the number of permissible conformations. This can be quantified for example by finding the entropy reduction for the ensemble of side chain dihedral angle degrees of freedom, and is plotted in FIG. 6 for H, D and S. For example, if the side chains in the sequence have less conformational freedom than the linear peptide, the entropy will be reduced. Such conformational restriction would enhance the conformational selectivity of antibodies specifically raised to this antigen. The term "more constrained conformation" as used herein means that the dihedral angle distribution (ensemble of allowable dihedral angles) of one or more dihedral angles is at least 10% more constrained than in the comparator conformation, as determined for example by the entropy of the amino acids, for example H, and/or D (e.g. a more constrained conformation has lower entropy). Specifically, the average entropy change relative to the entropy in the linear peptide, S(cyclic)−S (linear), of HDS in the overall more constrained cyclic conformational ensemble is on average reduced by more than 10% or reduced by more than 20% or reduced by more than 30% or reduced by more than 40%, from the unconstrained conformational ensemble, e.g. of the quantity S(linear)−S(fibril)/[mean(S(linear)+S(fibril))] for the linear peptide is approximately 81.7% entropy reduction for H6, 49.8% entropy reduction for D7, and −8.83% entropy reduction for S8 (the negative number implying that S8 has larger entropy for the cyclic peptide than the linear peptide).

The term "no or negligible plaque binding" or "lacks or has negligible plaque binding" as used herein with respect to an antibody means that the antibody does not show typical plaque morphology staining on immunohistochemistry (e.g. in situ) and the level of staining is comparable to or no more than 2 fold the level seen with an IgG negative (e.g. irrelevant) isotype control The term "Isolated peptide" refers to peptide that has been produced, for example, by recombinant or synthetic techniques, and removed from the source that produced the peptide, such as recombinant cells or residual peptide synthesis reactants. The isolated peptide is optionally "purified", which means at least: 80%, 85%, 90%, 95%, 98% or 99% purity and optionally pharmaceutical grade purity.

The term "detectable label" as used herein refers to moieties such as peptide sequences (such a myc tag, HA-tag, V5-tag or NE-tag), fluorescent proteins that can be appended or introduced into a peptide or compound described herein and which is capable of producing, either directly or indirectly, a detectable signal. For example, the label may be radio-opaque, positron-emitting radionuclide (for example for use in PET imaging), or a radioisotope, such as $^3$H, $^{13}$N, $^{14}$C, $^{18}$F, $^{32}$P, $^{35}$S, $^{123}$I, $^{125}$I, $^{131}$I; a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion. The detectable label may be also detectable indirectly for example using secondary antibody.

The term "epitope" as commonly used means an antibody binding site, typically a polypeptide segment, in an antigen that is specifically recognized by the antibody. As used herein "epitope" can also refer to the amino acid sequences or part thereof identified on A-beta using the collective coordinates method described. For example an antibody generated against an isolated peptide corresponding to a cyclic compound comprising the identified target region HDSG SEQ ID NO:1), recognizes part or all of said epitope sequence. An epitope is "accessible" in the context of the present specification when it is accessible to binding by an antibody.

The term "greater affinity" as used herein refers to a relative degree of antibody binding where an antibody X binds to target Y more strongly ($K_{on}$) and/or with a smaller dissociation constant ($K_{off}$) than to target Z, and in this context antibody X has a greater affinity for target Y than for Z. Likewise, the term "lesser affinity" herein refers to a degree of antibody binding where an antibody X binds to target Y less strongly and/or with a larger dissociation constant than to target Z, and in this context antibody X has a lesser affinity for target Y than for Z. The affinity of binding between an antibody and its target antigen, can be expressed as $K_A$ equal to $1/K_D$ where $K_D$ is equal to $k_{on}/k_{off}$. The $k_{on}$ and $k_{off}$ values can be measured using surface plasmon resonance technology, for example using a Molecular Affinity Screening System (MASS-1) (Sierra Sensors GmbH, Hamburg, Germany). An antibody that is selective for a conformation presented in a cyclic compound optional a cyclic peptide for example has a greater affinity for the cyclic compound (e.g. cyclic peptide) compared to a corresponding sequence in linear form (e.g. the sequence non-cyclized).

Also as used herein, the term "immunogenic" refers to substances that elicit the production of antibodies, activate T-cells and other reactive immune cells directed against an antigenic portion of the immunogen.

The term "corresponding linear compound" with regard to a cyclic compound refers to a compound, optionally a linear peptide, comprising or consisting of the same sequence or chemical moieties as the cyclic compound but in linear (i.e. non-cyclized) form for example having properties as would be present in solution of a linear peptide. For example, the corresponding linear compound can be the synthesized peptide that is not cyclized.

As used herein "specifically binds" in reference to an antibody means that the antibody recognizes an epitope sequence and binds to its target antigen with a minimum affinity. For example a multivalent antibody binds its target with a $K_D$ of at least 1e-6, at least 1e-7, at least 1e-8, at least 1e-9, or at least 1e-10. Affinities greater than at least 1e-8 may be preferred. An antigen binding fragment such as Fab fragment comprising one variable domain, may bind its target with a 10 fold or 100 fold less affinity than a multivalent interaction with a non-fragmented antibody.

The term "selectively binds" as used herein with respect to an antibody that selectively binds a form of A-beta (e.g. fibril, monomer or oligomer) or a cyclic compound means that the antibody binds the form with at least 2 fold, at least 3 fold, or at least 5 fold, at least 10 fold, at least 100 fold, at least 250 fold, at least 500 fold or at least 1000 fold or more greater affinity. Accordingly an antibody that is more selective for a particular conformation (e.g. oligomer) preferentially binds the particular form of A-beta with at least 2 fold etc greater affinity compared to another form and/or a linear peptide.

The term "linker" as used herein means a chemical moiety that can be covalently linked to the peptide comprising HDSG (SEQ ID NO: 1) epitope peptide, optionally linked to HDSG (SEQ ID NO: 1) peptide N- and C-termini to produce a cyclic compound. The linker can comprise a spacer and/or one or more functionalizable moieties. The linker via the functionalizable moieties can be linked to a carrier protein or an immunogen enhancing agent such as Keyhole Limpet Hemocyanin (KLH).

The term "spacer" as used herein means any preferably non-immunogenic or poorly immunogenic chemical moiety that can be covalently-linked directly or indirectly to a peptide N- and C-termini to produce a cyclic compound of longer length than the peptide itself, for example the spacer can be linked to the N- and C-termini of a peptide consisting of HDSG (SEQ ID NO: 1) to produce a cyclic compound of longer backbone length than the HDSG (SEQ ID NO: 1) sequence itself. That is, when cyclized, the peptide with a spacer (for example of 3 amino acid residues) makes a larger closed circle than the peptide without a spacer. The spacer may include, but is not limited to, moieties such as G, A, or PEG repeats, e.g. GHDSG (SEQ ID NO:7) GHDSGG (SEQ ID NO:8), GGHDSGG (SEQ ID NO:9), GHDSGGG (SEQ ID NO:10), etc. The spacer may comprise or be coupled to one or more functionalizing moieties, such as one or more cysteine (C) residues, which can be interspersed within the spacer or covalently linked to one or both ends of the spacer. Where a functionalizable moiety such as a C residue is covalently linked to one or more termini of the spacer, the spacer is indirectly covalently linked to the peptide. The spacer can also comprise the functionalizable moiety in a spacer residue as in the case where a biotin molecule is introduced into an amino acid residue.

The term "functionalizable moiety" as used herein refers to a chemical entity with a "functional group" which as used herein refers to a group of atoms or a single atom that will react with another group of atoms or a single atom (so called "complementary functional group") to form a chemical interaction between the two groups or atoms. In the case of cysteine, the functional group can be —SH which can be reacted to form a disulfide bond. Accordingly the linker can for example be CCC. The reaction with another group of atoms can be covalent or a strong non-covalent bond, for example as in the case of biotin-streptavidin bonds, which can have Kd~1e-14. A strong non-covalent bond as used herein means an interaction with a Kd of at least 1e-9, at least 1e-10, at least 1e-11, at least 1e-12, at least 1e-13 or at least 1e-14.

Proteins and/or other agents may be functionalized (e.g. coupled) to the cyclic compound, either to aid in immunogenicity, or to act as a probe in in vitro studies. For this purpose, any functionalizable moiety capable of reacting (e.g. making a covalent or non-covalent but strong bond) may be used. In one specific embodiment, the functionalizable moiety is a cysteine residue which is reacted to form a disulfide bond with an unpaired cysteine on a protein of interest, which can be, for example, an immunogenicity enhancing agent such as Keyhole Limpet Hemocyanin (KLH), or a carrier protein such as Bovine serum albumin (BSA) used for in vitro immunoblots or immunohistochemical assays.

The term "reacts with" as used herein generally means that there is a flow of electrons or a transfer of electrostatic charge resulting in the formation of a chemical interaction.

The term "animal" or "subject" as used herein includes all members of the animal kingdom including mammals, optionally including or excluding humans.

A "conservative amino acid substitution" as used herein, is one in which one amino acid residue is replaced with another amino acid residue without abolishing the protein's desired properties. Suitable conservative amino acid substitutions can be made by substituting amino acids with similar hydrophobicity, polarity, and R-chain length for one another. Examples of conservative amino acid substitution include:

| Conservative Substitutions | |
| --- | --- |
| Type of Amino Acid | Substitutable Amino Acids |
| Hydrophilic | Ala, Pro, Gly, Glu, Asp, Gln, Asn, Ser, Thr |
| Sulphydryl | Cys |
| Aliphatic | Val, Ile, Leu, Met |
| Basic | Lys, Arg, His |
| Aromatic | Phe, Tyr, Trp |

The term "sequence identity" as used herein refers to the percentage of sequence identity between two polypeptide sequences or two nucleic acid sequences. To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions.times.100%). In one embodiment, the two sequences are the same length. The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules of the present application. BLAST protein searches can be performed with the XBLAST program parameters set, e.g., to score-50, wordlength=3 to obtain amino acid sequences homologous to a protein molecule described herein. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). Another preferred non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

For antibodies, percentage sequence identities can be determined when antibody sequences maximally aligned by IMGT or other (e.g. Kabat numbering convention). After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

The term "nucleic acid sequence" as used herein refers to a sequence of nucleoside or nucleotide monomers consisting of naturally occurring bases, sugars and intersugar (backbone) linkages. The term also includes modified or substituted sequences comprising non-naturally occurring monomers or portions thereof. The nucleic acid sequences of the present application may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine. The nucleic acid can be either double stranded or single stranded, and represents the sense or antisense strand. Further, the term "nucleic acid" includes the complementary nucleic acid sequences as well as codon optimized or synonymous codon equivalents. The term "isolated nucleic acid sequences" as used herein refers to a nucleic acid substantially free of cellular material or culture medium when produced by recombinant DNA techniques, or chemical precursors, or other chemicals when chemically synthesized. An isolated nucleic acid is also substantially free of sequences which naturally flank the nucleic acid (i.e. sequences located at the 5' and 3' ends of the nucleic acid) from which the nucleic acid is derived.

"Operatively linked" is intended to mean that the nucleic acid is linked to regulatory sequences in a manner which allows expression of the nucleic acid. Suitable regulatory sequences may be derived from a variety of sources, including bacterial, fungal, viral, mammalian, or insect genes. Selection of appropriate regulatory sequences is dependent on the host cell chosen and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

The term "vector" as used herein comprises any intermediary vehicle for a nucleic acid molecule which enables said nucleic acid molecule, for example, to be introduced into prokaryotic and/or eukaryotic cells and/or integrated into a genome, and include plasmids, phagemids, bacteriophages or viral vectors such as retroviral based vectors, Adeno Associated viral vectors and the like. The term "plasmid" as used herein generally refers to a construct of extrachromosomal genetic material, usually a circular DNA duplex, which can replicate independently of chromosomal DNA.

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.–16.6 (Log 10 [Na+])+0.41(% (G+C)–600/l), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm−5° C. based on the above equation, followed by a wash of 0.2×SSC/0.1% SDS at 60° C. Moderately stringent hybridization conditions include a washing step in 3×SSC at 42° C. It is understood, however, that equivalent stringencies may be achieved using alternative buffers, salts and temperatures. Additional guidance regarding hybridization conditions may be found in: Current Protocols in Molecular Biology, John Wiley & Sons, N.Y., 2002, and in: Sambrook et al., Molecular Cloning: a Laboratory Manual, Cold Spring Harbor Laboratory Press, 2001.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "Treatment" can also mean prolonging survival as compared to expected survival if not receiving treatment. "Treating" and "treatment" as used herein also include prophylactic treatment. For example, a subject with early stage AD can be treated to prevent progression can be treated with a compound, antibody, immunogen, nucleic acid or composition described herein to prevent progression.

The term "administered" as used herein means administration of a therapeutically effective dose of a compound or composition of the disclosure to a cell or subject.

As used herein, the phrase "effective amount" means an amount effective, at dosages and for periods of time necessary to achieve a desired result. Effective amounts when administered to a subject may vary according to factors such as the disease state, age, sex, weight of the subject. Dosage regime may be adjusted to provide the optimum therapeutic response.

The term "pharmaceutically acceptable" means that the carrier, diluent, or excipient is compatible with the other components of the formulation and not substantially deleterious to the recipient thereof.

Compositions or methods "comprising" or "including" one or more recited elements may include other elements not specifically recited. For example, a composition that "comprises" or "includes" an antibody may contain the antibody alone or in combination with other ingredients.

In understanding the scope of the present disclosure, the term "consisting" and its derivatives, as used herein, are intended to be close ended terms that specify the presence of stated features, elements, components, groups, integers, and/or steps, and also exclude the presence of other unstated features, elements, components, groups, integers and/or steps.

The recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about." Further, it is to be understood that "a," "an," and "the" include plural referents unless the content clearly dictates otherwise. The term "about" means plus or minus 0.1 to 50%, 5-50%, or 10-40%, preferably 10-20%, more preferably 10% or 15%, of the number to which reference is being made.

Further, the definitions and embodiments described in particular sections are intended to be applicable to other embodiments herein described for which they are suitable as would be understood by a person skilled in the art. For example, in the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The singular forms of the articles "a," "an," and "the" include plural references unless the context clearly dictates otherwise. For example, the term "a compound" or "at least one compound" can include a plurality of compounds, including mixtures thereof.

II. Epitopes and Binding Proteins

The inventors have identified an "epitope region" in A-beta HDSG (SEQ ID NO: 1) at amino acid residues 6 to 9 of A-beta. They have further identified that the epitope region may be or comprise a conformational epitope, and that HDSG (SEQ ID NO: 1) may be selectively accessible to antibody binding in oligomeric species of A-beta.

Without wishing to be bound by theory, fibrils may present interaction sites that have a propensity to catalyze oligomerization. This may only occur when selective fibril surface not present in normal individuals is exposed and able to have aberrant interactions with A-beta monomers. Environmental challenges such as low pH, osmolytes present during inflammation, or oxidative damage may induce disruption in fibrils that can lead to exposure of more weakly stable regions. There is interest, then, to predict these weakly-stable regions, and use such predictions to rationally design antibodies that could target them. Regions likely to be disrupted in the fibril may also be good candidates for exposed regions in oligomeric species.

Computer based systems and methods to predict contiguous protein regions that are prone to disorder are described in U.S. Patent Application Ser. No. 62/253,044, SYSTEMS AND METHODS FOR PREDICTING MISFOLDED PROTEIN EPITOPES BY COLLECTIVE COORDINATE BIASING filed Nov. 9, 2015 which is hereby incorporated by reference in its entirety. As described in the Examples, the methods were applied to A-beta and identified an epitope that as demonstrated herein is specifically or selectively more accessible in A-beta oligomers.

As described in the Examples, cyclic peptide cyclo (CGHDSGG) (SEQ ID NO:2) may capture one or more of the conformational differences of the HDSG (SEQ ID NO: 1) epitope in oligomers relative to the monomer and/or fibril species. For example, differences in solvent accessible surface area, curvature, RMSD structural alignment, and the dihedral angle distributions for several of the amino acids and dihedral angles in the cyclic 7-mer cyclo (CGHDSGG) (SEQ ID NO:2) were found to be substantially different than either the monomer and/or fibril, suggesting that the cyclic peptide provides for a conformational epitope that is distinct from the linear epitope. Antibodies raised using an immunogen comprising cyclo(CGHDSGG) (SEQ ID NO:2) selectively bound cyclo(CGHDSGG) (SEQ ID NO:2) over linear CGHDSGG (SEQ ID NO:2) and selectively bound synthetic and/or native oligomeric A-beta species compared to monomeric A-beta and A-beta fibril plaques. Further antibodies raised to cyclo(CGHDSGG) were able to inhibit in vitro propagation of A-beta aggregation.

II. HDSG (SEQ ID NO: 1) "Epitope" Compounds

Accordingly, the present disclosure identifies an epitope in A-beta consisting of amino acids HDSG (SEQ ID NO: 1)

or a part thereof, HDSG (SEQ ID NO: 1) corresponding to amino acids residues 6-9 on A-beta. As demonstrated in the Examples, epitopes HDSG (SEQ ID NO:1), HDSGY (SEQ ID NO:4) and RHDSG (SEQ ID NO:5) (included in the epitopes collectively referred to herein as "HDSG and related epitopes") were identified as regions prone to disorder in an A-beta fibril. The residues HDSG (SEQ ID NO: 1) emerged in two predictions using the collective coordinates method, while the flanking residues of this epitope, R5 and Y10, each occurred in one prediction.

An aspect includes a compound comprising an isolated A-beta peptide comprising or consisting of HDSG (SEQ ID NO:1), sequence of a related epitope and/or part of any of the foregoing.

In an embodiment, the A-beta peptide is selected from an amino acid sequence comprising or consisting of HDSG (SEQ ID NO:1), HDSGY (SEQ ID NO:4) or RHDSG (SEQ ID NO:5). In an embodiment the A-beta peptide has a sequence of an A-beta peptide as set forth in any one of the epitopes in Table 12. In an embodiment, the compound comprises the sequence as set forth in any of SEQ ID NO: 2, SEQ ID NOs:2, 28 and 29.

In an embodiment, the compound is a cyclic compound, such as a cyclopeptide. The terms cyclopeptide and cyclic peptide are used interchangeably herein.

In some embodiments, the A-beta peptide comprising HDSG (SEQ ID NO: 1) (or a part thereof) can include 1, 2 or 3 additional residues present in A-beta, N- and/or C-terminus of HDSG (SEQ ID NO: 1) (or the part thereof), for example the A-beta peptide can include 1 residue N-terminal and be RHDSG (SEQ ID NO:5). As shown for example in the A-beta sequence of SEQ ID NO: 3, the 3 amino acids N-terminal to HDSG (SEQ ID NO:1) in A-beta are EFR and the 3 amino acids C-terminal to HDSG (SEQ ID NO: 1) are YEV. In embodiments, where the compound comprising the A-beta peptide is cyclized, the A-beta peptide is or is a maximum of 8, A-beta residues, 7 A-beta residues or 6 A-beta residues. In an embodiment, the A-beta peptide is or is a maximum of 5 A-beta residues. For example, where the A-beta peptide is 6 amino acids it may comprise or consist of the amino acid sequence RHDSGY (SEQ ID NO:13), HDSGYE (SEQ ID NO: 11), DSGYEV (SEQ ID NO: 15) or FRHDSG (SEQ ID NO: 16).

In an embodiment, the compound further includes a linker. The linker comprises a spacer and/or one or more functionalizable moieties. The linker can for example comprise 1, 2, 3, 4, 5, 6, 7 or 8 amino acids and/or equivalently functioning molecules such as polyethylene glycol (PEG) moieties, and/or a combination thereof. In an embodiment, the spacer amino acids are selected from non-immunogenic or poorly immunogenic amino acid residues such as G and A, for example the spacer can be GGG, GAG, G(PEG)G, PEG-PEG-GG and the like. One or more functionalizable moieties e.g. amino acids with a functional group may be included for example for coupling the compound to an agent or detectable label or a carrier such as BSA or an immunogenicity enhancing agent such as KLH.

In an embodiment the linker comprises GC-PEG, PEG-GC, GCG or PEG-C-PEG.

In an embodiment, the linker comprises 2, 3, 4, 5, 6, 7 or 8 amino acids.

In embodiments wherein the A-beta peptide comprising HDSG (SEQ ID NO: 1) or a part thereof includes 1, 2 or 3 additional residues found in A-beta that are N- and/or C-terminal to HDSG (SEQ ID NO: 1) the linker is covalently linked to the N- and/or C-termini of the A-beta residues (e.g. where the peptide is RHDSG (SEQ ID NO:5), the linker is covalently linked to R and G residues). Similarly, where the A-beta peptide is HDSG (SEQ ID NO:1), the linker is covalently linked to residues H and G and where the A-beta peptide is HDSGY(SEQ ID NO:4), the linker is covalently linked to residues H and Y.

Proteinaceous portions of compounds (or the compound wherein the linker is also proteinaceous) may be prepared by chemical synthesis using techniques well known in the chemistry of proteins such as solid phase synthesis or synthesis in homogenous solution.

As mentioned, the compound can be a cyclic compound. Reference to the "cyclic peptide" herein can refer to a fully proteinaceous compound (e.g. wherein the linker is for example 1, 2, 3, 4, 5, 6, 7 or 8 amino acids). It is understood that properties described for the cyclic peptide determined in the examples can be incorporated in other compounds (e.g. other cyclic compounds) comprising non-amino acid linker molecules. The terms "cyclopeptide" and "cyclic peptide" are used interchangeably herein.

An aspect therefore provides a cyclic compound comprising peptide HDSG (SEQ ID NO: 1) (or a part thereof such as DSG) and a linker, wherein the linker is covalently coupled directly or indirectly to the peptide comprising HDSG (SEQ ID NO: 1) (e.g. the H and the G residues when the peptide consists of HDSG (SEQ ID NO: 1)). In the cyclic compound for example, at least H, D and/or S is in an alternate conformation than H, D and/or S in a corresponding linear peptide, optionally in a more constrained conformation.

In an embodiment, the cyclic compound comprises an A-beta peptide comprising HDSG (SEQ ID NO: 1) and up to 6 A-beta residues (e.g. 1 or 2 amino acids N and/or C terminus to HDSG (SEQ ID NO: 1)) and a linker, wherein the linker is covalently coupled directly or indirectly to the peptide N-terminus residue and the C-terminus residue of the A-beta peptide. In the cyclic compound for example at least D is in an alternate conformation than D in a corresponding linear peptide, or at least S is in an alternate conformation than S in a corresponding linear peptide and optionally wherein at least H, or at least D, is in a more constrained conformation than the conformation occupied in the corresponding linear peptide comprising.

The cyclic compound can be synthesized as a linear molecule with the linker covalently attached to the N-terminus or C-terminus of the peptide comprising the A-beta peptide, optionally HDSG (SEQ ID NO:1) or related epitope, prior to cyclization. Alternatively part of the linker is covalently attached to the N-terminus and part is covalently attached to the C-terminus prior to cyclization. In either case, the linear compound is cyclized for example in a head to tail cyclization (e.g. amide bond cyclization).

In an embodiment the cyclic compound comprises an A-beta peptide comprising or consisting of HDSG (SEQ ID NO:1) and a linker, wherein the linker is coupled to the N- and C-termini of the peptide (e.g. the H and the G residues when the peptide consists of HDSG (SEQ ID NO:1).). In an embodiment, at least H, D and/or S is in an alternate conformation in the cyclic compound than occupied by H, D and/or S in a linear compound, (e.g. linear peptide) comprising HDSG (SEQ ID NO: 1).

The linear peptide comprising the A-beta sequence, can be comprised in a linear compound. The linear compound or the linear peptide comprising HDSG (SEQ ID NO: 1) is in an embodiment, a corresponding linear peptide. In another embodiment, the linear peptide is any length of A-beta peptide comprising HDSG (SEQ ID NO: 1), including for example a linear peptide comprising A-beta residues 1-35, or smaller portions thereof such as A-beta residues 1-20, 2-20, 3-20, 1-15, 3-15, 3-12 and the like etc. The linear peptide can in some embodiments also be a full length A-beta peptide.

In an embodiment, at least H, D and/or S is in an alternate conformation in the cyclic compound than occupied by a residue, optionally by H and/or D, in the monomer and/or fibril.

In an embodiment, at least D, S and/or H is in an alternate conformation in the cyclic compound than occupied by a residue, optionally by D and/or S, in the monomer and/or fibril.

In an embodiment, the alternate conformation is a constrained conformation.

In an embodiment, at least H, optionally alone or in combination with at least D is in a more constrained conformation than the conformation occupied in a linear peptide comprising HDSG (SEQ ID NO: 1).

In an embodiment, the conformation of H and/or H in combination with one or more of D and/or S is comprised in the compound in an alternate conformation, optionally in a more constrained conformation.

As shown in FIG. 6, residues H and D are in a more constrained conformation in the cyclic compound compared to the conformational ensemble present in the linear peptide. The FIG. shows that there is approximately a 81.7% entropy reduction for H and approximately a 49.8% entropy reduction for D. In an embodiment, the cyclic compound has a conformation H and/or D that is at least 10%, at least 20%, at least 25%, at least 30%, at least 35% or at least 40% more constrained compared to a corresponding linear compound, as quantified by that residue's reduction in entropy.

For example, the alternate conformation can include one or more differing dihedral angles in residues H, and/or D, and/or S, and optionally in D and/or S differing from the dihedral angles in the linear peptide and/or peptide in the context of the fibril.

As shown in FIG. 4, the dihedral angle distribution of D7 is substantially different in the cyclic peptide compared to the linear peptide or residue in the context of the fibril. In an embodiment, the cyclic compound comprises a D comprising an O-C-Cα-Cβ (also referred to as O-C-CA-CB) dihedral angle that is at least 30 degrees, at least 40 degrees, at least 50 degrees, at least 60 degrees, at least 70 degrees, at least 80 degrees, at least 90 degrees, at least 100 degrees, at least 110 degrees, at least 120 degrees, at least 130 degrees, or at least 140 degrees different, than the corresponding dihedral angle in the context of the linear peptide and/or fibril. For example, Table 1 indicates that for simulated linear peptides, cyclic peptides, and fibrils, the difference in this dihedral angle is about 160 degrees between cyclic and linear, and about 195 degrees between cyclic and fibril. Accordingly in an embodiment, the cyclic compound comprises a D comprising an O-C-Cα-Cβ (also referred to as O-C-CA-CB) dihedral angle that is at least 140 degrees different, at least 150 degrees different, at least 160 degrees different, at least 170 degrees different, than the corresponding dihedral angle in the context of the fibril.

Table 1 also identifies differences in the dihedral angle distributions for other angles, including those for example in residues H, D and S.

Accordingly in an embodiment the cyclic compound comprises an A-beta peptide residue selected from H, D and S, wherein at least one dihedral angle is at least 30 degrees, at least 40 degrees, at least 50 degrees, at least 60 degrees, at least 70 degrees, at least 80 degrees, at least 90 degrees, at least 100 degrees, at least 110 degrees, at least 120 degrees, at least 130 degrees or at least 140 degrees different, than the corresponding dihedral angle in the context of the linear compound.

In an embodiment, the cyclic compound comprises a minimum average side-chain/backbone dihedral angle difference between the cyclic compound and linear peptide. For example, it is demonstrated for the centroid conformations listed in Table 3, that the average side-chain/backbone dihedral angle difference between the cyclic and linear peptide is as follows H: 28.5 degrees, D: 133 degrees, S: 129 degrees, G: 13 degrees. The corresponding numbers between the cyclic and fibril are H: 51 degrees, D: 103 degrees, S: 114 degrees, G: 73 degrees.

Accordingly, in an embodiment, the cyclic compound comprises an average side-chain difference compared to the linear peptide of at least: for H, at least 20 degrees; for D and/or S at least 30 degrees, at least 40 degrees, at least 50 degrees, at least 60 degrees, at least 70 degrees, at least 80 degrees, at least 90 degrees, at least 100 degrees, at least 110 degrees or at least 120 degrees; and/or for G, at least 30 degrees, at least 40 degrees, at least 50 degrees or at least 60 degrees.

The angle difference can for example be positive or negative, (+) or (−).

The alternate conformation can comprise an alternate backbone orientation. For example, the backbone orientation that the cyclic epitope exposes for an antibody differs compared to linear or fibril form.

FIG. 7 plots the phi and psi angles sampled in equilibrium simulations, for residues H6, D7, S8, and G9 in both linear and cyclic peptides consisting of sequence CGHGSGG, as well as HDSG (SEQ ID NO: 1) in the context of the equilibrated fibril structure using initial condition from PDB 2M4J. From FIG. 7 it is seen that the distribution of backbone dihedral angles (Ramachandran phi/psi angles) in the cyclic peptide is different from the distribution of Ramachandran angles sampled for either the linear peptide, or for the A-beta peptide HDSG (SEQ ID NO: 1) in the context the fibril structure 2M4J, particularly for residues D7 and S8. Table 2 lists differences for peak values of distributions of backbone phi/psi angles. Similarly Table 3 shows backbone phi/phi angles and the differences for the centroid structures (plotted in FIG. 10). For example, for the centroid conformations of the largest linear cluster and largest fibril cluster, for which dihedral angles are listed in Table 3, the average backbone Ramachandran angle difference ($\Delta\phi$, $\Delta\psi$) between the cyclic and linear peptide is given as follows for HDSG (SEQ ID NO: 1): (−3.0, −1.1) degrees, (72.6, 164.1) degrees: (67.8, 195.1) degrees, (−38.8, 13.4) degrees; the average backbone Ramachandran angle difference ($\Delta\phi$, $\Delta\psi$) between the cyclic and fibril peptide is given as follows: (−53.7, 29.7) degrees, (4.7, −154.5) degrees, (86.5, 129) degrees, (127, −163.8) degrees.

Accordingly, in an embodiment, the cyclic compound comprises an A-beta peptide with at least one residue wherein backbone phi/psi angles is at least 30 degrees, at least 40 degrees, at least 50 degrees, at least 60 degrees, at least 70 degrees, at least 80 degrees different, at least 90 degrees, at least 100 degrees, at least 110 degrees, at least 120 degrees, at least 130 degrees, at least 140 degrees, at least 150 degrees, at least 160 degrees, at least 170 degrees or at least 180 degrees compared to the corresponding linear peptide or in a fibril PDB structure.

The alternate conformation can also include an increase in curvature centered around an amino acid or of the cyclic compound comprising HDSG (SEQ ID NO: 1) or a related epitope relative to a corresponding linear peptide and/or A-beta fibril.

In an embodiment, the alternate conformation HDSG (SEQ ID NO: 1) has an increased curvature relative to linear HDSG (SEQ ID NO: 1). As shown in the Examples, the curvature of the backbone at the positions of D7 and S8 in the cyclic compound is increased relative to the curvature at those positions in the linear peptide, or peptide in the context of the fibril (FIG. 2) as described in Example 2.

The values of the curvature were determined for H, D, S, G in cyclo(CGHDSGG) (SEQ ID NO:2), linear CGHDSGG (SEQ ID NO:2), and HDSG (SEQ ID NO:1) in the context of the fibril and are described in Example 2.

Accordingly, the compound comprises an A-beta peptide wherein the curvature of the D and/or S in the alternate conformation is increased by at least 0.1, 0.2, 0.3 or more radians compared to the corresponding linear peptide, or D7 or S8 in the context of the fibril.

In an embodiment, the HD, DS, SG, HDS, DSG, and/or HDSG (SEQ ID NO: 1) are in an alternate conformation, for example as compared to what is occupied by these residues in a non-oligomeric conformation, such as the linear peptide and/or fibril.

Further the entropy of the side chains is reduced in the cyclic peptide relative to the linear peptide, rendering the side chains in a more structured conformation than the linear peptide.

As demonstrated herein, the curvature of the cyclic compound is for some amino acids different than that in the linear peptide or to the peptide in the context of the fibril (FIG. 2). For example the curvature of D7 in the context of the cyclic compound CGHDSGG (SEQ ID NO: 2) compared to the corresponding linear peptide is increased.

Accordingly in one embodiment, the curvature of D and/or S in the cyclic compound is increased by at least 10%, at least 20%, or at least 30% compared to a corresponding linear compound.

It is also demonstrated, that one or more of the dihedral angles in residues H, and/or D, and/or S, tend to be significantly different from the dihedral angles in the linear peptide or peptide in the context of the fibril. For these amino acids, when the solvent accessible surface area (SASA) is weighted by the solubility, more emphasis is placed on residue S8. The entropy of the side chains of H6 is reduced in the cyclic peptide relative to the linear peptide and even the fibril, implying the tendency to have a restricted pose for this residue.

Cyclic compounds which show similar changes are also encompassed.

The cyclic compound in some embodiments that comprises a peptide comprising HDSG (SEQ ID NO: 1) or related epitope can include 1, 2, 3 or more residues in A-beta directly upstream and/or downstream of HDSG (SEQ ID NO: 1) or the related epitope. In such cases the spacer is covalently linked to the N- and C-termini of the ends of the corresponding residues of the A-beta sequence.

In some embodiments, the linker or spacer is indirectly coupled to the N- and C-terminus residues of the A-beta peptide.

In an embodiment, the cyclic compound is a compound shown in FIG. 11B.

Methods for making cyclized peptides are known in the art and include SS-cyclization or amide cyclization (head-to-tail, or backbone cyclization). Methods are further described in Example 3. For example, a peptide with "C" residues at its N- and C-termini, e.g. CGHDSGGC (SEQ ID NO: 2), can be reacted by SS-cyclization to produce a cyclic peptide.

As described in Example 2, a cyclic compound of FIG. 11B was assessed for its relatedness to the conformational epitope identified. The cyclic compound comprising HDSG (SEQ ID NO: 1) peptide for example can be used to raise antibodies selective for one or more conformational features.

The epitope HDSG (SEQ ID NO: 1) and/or a part thereof, as described herein may be a potential target in misfolded propagating strains of A-beta involved in A-beta, and antibodies that recognize the conformational epitope may for example be useful in detecting such propagating strains.

Also provided in another aspect is an isolated peptide comprising an A-beta peptide sequence described herein, including linear peptides and cyclic peptides. Linear peptides can for example be used for selecting antibodies for lack of binding thereto. The isolated peptide can comprise a linker sequence described herein. The linker can be covalently coupled to the N or C terminus or may be partially coupled to the N terminus and partially coupled to the C terminus as in CGHDSGG (SEQ ID NO: 2) linear peptide. In the cyclic peptide, the linker is coupled to the C-terminus and N-terminus directly or indirectly.

Another aspect includes an immunogen comprising a compound, optionally a cyclic compound described herein. The immunogen may also comprise for example HDS, DSG or HDSG (SEQ ID NO: 1) or additional A-beta sequence. The amino acids may be directly upstream and/or downstream (i.e. N-terminal and/or C-terminal) of HDS, DSG or HDSG (SEQ ID NO: 1) or related epitope sequence. Antibodies raised against such immunogens can be selected for example for binding to a cyclopeptide comprising HDSG (SEQ ID NO:1) or a related epitope.

A immunogen is suitably prepared or formulated for administration to a subject, for example, the immunogen may be sterile, or purified.

In an embodiment, the immunogen is a cyclic peptide comprising HDSG or a related epitope.

In an embodiment, the immunogen comprises immunogenicity enhancing agent such as Keyhole Limpet Hemocyanin (KLH) or a MAP antigen. The immunogenicity enhancing agent can be coupled to the compound either directly, such as through an amide bound, or indirectly through a functionalizable moiety in the linker. When the linker is a single amino acid residue (for example with the A-beta peptide in the cyclic compound is 6 amino acid residues) the linker can be the functionalizable moiety (e.g. a cysteine residue).

The immunogen can be produced by conjugating the cyclic compound containing the constrained epitope peptide to an immunogenicity enhancing agent such as Keyhole Limpet Hemocyanin (KLH) or a carrier such bovine serum albumin (BSA) using for example the method described in Lateef et al 2007, herein incorporated by reference. In an embodiment, the method described in Example 3 or 4 is used.

A further aspect is an isolated nucleic acid molecule encoding the proteinaceous portion of a compound or immunogen described herein.

In embodiment, the nucleic acid molecule encodes any one of the amino acid sequences sent forth in SEQ ID NOS: 1-16.

In an embodiment, nucleic acid molecule encodes HDSG (SEQ ID NO: 1) or a related epitope and optionally a linker described herein.

A further aspect is a vector comprising said nucleic acid. Suitable vectors are described elsewhere herein.

III. Antibodies, Cells and Nucleic Acids

The compounds and particularly the cyclic compounds described above can be used to raise antibodies that specifically bind DS, HDS or HDSG (SEQ ID NO: 1) in A-beta (e.g. residues 6-7, 6-8 or 6-9) and/or which recognize specific conformations of DS, HDSV or HDSG (SEQ ID NO: 1) in species of A-beta, for example oligomeric species of A-beta. Similarly cyclic compounds comprising for example RHDSG (SEQ ID NO: 5), HDSGY (SEQ ID NO: 4), HDSG (SEQ ID NO: 1) and/or other related epitope sequences described herein can be used to raise antibodies that specifically bind HDSG (SEQ ID NO: 1) etc and/or specific conformational epitopes thereof. As demonstrated herein, antibodies were raised to cyclo(CGHDSGG) (SEQ ID NO: 2), which specifically and/or selectively bound cyclo(CGHDSGG) (SEQ ID NO: 2) over linear CGHDSGG (SEQ ID NO: 2).

Accordingly as aspect includes an antibody (including a binding fragment thereof) that specifically binds to an A-beta peptide having of a sequence HDSG (SEQ ID NO: 1) or a related epitope sequence, for example as set forth in any one of SEQ ID NOs: 1 to 16.

In an embodiment, the A-beta peptide is comprised in a cyclic peptide and the antibody is specific or selective for A-beta presented in the cyclic compound.

In an embodiment, the antibody specially and/or selectively binds the A-beta peptide of the cyclic compound, wherein the A-beta has a sequence as set forth in any one of SEQ ID NOs: 1 to 16.

In an embodiment, the cyclic compound is a cyclic peptide. In an embodiment, A-beta peptide in the cyclic peptide is any one of SEQ ID NO: 1-16. In a further embodiment, the cyclic peptide has a sequence as set forth in SEQ ID NO: 2, 12, 28 or 29.

As described in the examples, antibodies having one or properties can be selected using assays described in the Examples.

In an embodiment, the antibody does not bind a linear peptide comprising the sequence HDSG (SEQ ID NO: 1), optionally wherein the sequence of the linear peptide is a linear version of a cyclic sequence used to raise the antibody, optionally as set forth in SEQ ID NO: 2, 12, 28 or 29.

In an embodiment, the antibody is selective for the A-beta peptide as presented in the cyclic compound relative to a corresponding linear compound comprising the A-beta peptide.

In an embodiment, the antibody specifically binds an epitope on A-beta, the epitope comprising or consisting HDSG (SEQ ID NO: 1) or a related epitope thereof.

In an embodiment, the epitope recognized specifically or selectively by the antibody on A-beta is a conformational epitope.

In an embodiment, the antibody is isolated.

In an embodiment, the antibody is an exogenous antibody

As described in the Examples, H, D, and/or S in the cyclic compound may be predominantly accessible or exposed in conformations of A-beta that are distinct from a corresponding linear peptide, monomer and/or fibril forms.

Accordingly a further aspect is an antibody which specifically binds an epitope on A-beta, wherein the epitope comprises or consists of at least one amino acid residue predominantly involved in binding to the antibody, wherein the at least one amino acid is H, D or S embedded within the sequence HDSG (SEQ ID NO:1). In an embodiment, the epitope comprises or consists of at least two consecutive amino acid residues predominantly involved in binding to the antibody, wherein the at least two consecutive amino acids are HD or DS or SG embedded within HDSG (SEQ ID NO:1).

In another embodiment, the epitope consists of HDSG (SEQ ID NO:1) or a related epitope.

In an embodiment, the antibody is a conformation selective antibody. In an embodiment, the antibody selectively binds a cyclic compound comprising an epitope peptide sequence described herein compared to the corresponding linear sequence. For example an antibody that binds a particular epitope conformation can be referred to as a conformation specific antibody. Such antibodies can be selected using the methods described herein. The conformation selective antibody can differentially recognize a particular A-beta species or a group of related species (e.g. dimers, trimers, and other oligomeric species) and can have a higher affinity for one species or group of species compared to another (e.g. to either the monomer or fibril species).

In an embodiment, the antibody does not specifically bind monomeric A-beta. In an embodiment, the antibody does not specifically bind A-beta senile plaques, for example in situ in AD brain tissue.

In another embodiment, the antibody does not selectively bind monomeric A-beta compared to native- or synthetic-oligomeric A-beta.

For example, the antibody may specifically bind a cyclic compound comprises a residue selected from H, D and S, wherein at least one dihedral angle is at least 30 degrees, at least 40 degrees, at least 50 degrees, at least 60 degrees, at least 70 degrees, at least 80 degrees, at least 90 degrees, at least 100 degrees, at least 110 degrees, at least 120 degrees, at least 130 degrees or at least 140 degrees different in the cyclic compound, than the corresponding dihedral angle in the context of the linear compound.

In an embodiment, the antibody selectively binds A-beta peptide in a cyclic compound, the A-beta comprising HDSG (SEQ ID NO: 1) or a part thereof, relative to a linear peptide comprising HDSG (SEQ ID NO: 1), such as a corresponding sequence. For example, in an embodiment the antibody selectively binds HDSG (SEQ ID NO: 1) in a cyclic conformation and has at least 2 fold, at least 3 fold, at least 5 fold, at least 10 fold at least 20 fold, at least 30 fold, at least 40 fold, at least 50 fold, at least 100 fold, at least 500 fold, at least 1000 fold greater selectivity (e.g. greater binding affinity) for HDSG (SEQ ID NO: 1) in the cyclic conformation compared to HDSG (SEQ ID NO: 1) in a linear peptide, for example as measured by ELISA, or optionally a method described herein.

In an embodiment, the cyclic compound is cyclo(CGHDSGG) (SEQ ID NO: 2) or the cyclic compound with sequence as set forth in SEQ ID NO: 12, 28 or 29.

In an embodiment, the antibody selectively binds A-beta peptide in a cyclic compound and/or oligomeric A-beta. In an embodiment, the selectivity is at least 2 fold, at least 3 fold, at least 5 fold, at least 10 fold, at least 20 fold, at least 30 fold, at least 40 fold, at least 50 fold, at least 100 fold, at least 500 fold, at least 1000 fold more selective for the A-beta peptide in the cyclic compound and/or A-beta oligomer over a species of A-beta selected from A-beta monomer and/or A-beta fibril and/or a compound comprising a corresponding linear peptide.

In an embodiment, the antibody lacks A-beta fibril plaque (also referred to as senile plaque) staining. Absence of plaque staining can be assessed by comparing to a positive control such as A-beta-specific antibodies 6E10 and 4G8 (Biolegend, San Diego, CA), or 2C8 (Enzo Life Sciences Inc., Farmingdale, NY) and an isotype control. An antibody described herein lacks or has negligible A-beta fibril plaque staining if the antibody does not show typical plaque morphology staining and the level of staining is comparable to or no more than 2 fold the level seen with an IgG negative isotype control. The scale can for example set the level of staining with isotype control at 1 and with 6E10 at 10. An antibody lacks A-beta fibril plaque staining if the level of staining on such a scale is 2 or less. In embodiment, the antibody shows minimal A-beta fibril plaque staining, for example on the foregoing scale, levels scored at less about or less than 3.

In an embodiment, the antibody is a monoclonal antibody.

To produce monoclonal antibodies, antibody producing cells (B lymphocytes) can be harvested from a subject immunized with an immunogen described herein, and fused with myeloma cells by standard somatic cell fusion procedures thus immortalizing these cells and yielding hybridoma cells. Such techniques are well known in the art, (e.g. the hybridoma technique originally developed by Kohler and Milstein (Nature 256:495-497 (1975)) as well as other techniques such as the human B-cell hybridoma technique (Kozbor et al., Immunol. Today 4:72 (1983)), the EBV-hybridoma technique to produce human monoclonal antibodies (Cole et al., Methods Enzymol, 121: 140-67 (1986)), and screening of combinatorial antibody libraries (Huse et al., Science 246:1275 (1989)). Hybridoma cells can be screened immunochemically for production of antibodies specifically reactive with the epitope sequences described herein and the monoclonal antibodies can be isolated.

Specific antibodies, or antibody fragments, reactive against particular antigens or molecules, may also be generated by screening expression libraries encoding immunoglobulin genes, or portions thereof, expressed in bacteria with cell surface components. For example, complete Fab fragments, VH regions and FV regions can be expressed in bacteria using phage expression libraries (see for example Ward et al., Nature 41:544-546 (1989); Huse et al., Science 246:1275-1281 (1989); and McCafferty et al., Nature 348: 552-554 (1990).

In an embodiment, the antibody is a humanized antibody.

The humanization of antibodies from non-human species has been well described in the literature. See for example EP-B1 0 239400 and Carter & Merchant 1997 (Curr Opin Biotechnol 8, 449-454, 1997 incorporated by reference in their entirety herein). Humanized antibodies are also readily obtained commercially (e.g. Scotgen Limited, 2 Holly Road, Twickenham, Middlesex, Great Britain).

Humanized forms of rodent antibodies are readily generated by CDR grafting (Riechmann et al. Nature, 332:323-327, 1988). In this approach the six CDR loops comprising the antigen binding site of the rodent monoclonal antibody are linked to corresponding human framework regions. CDR grafting often yields antibodies with reduced affinity as the amino acids of the framework regions may influence antigen recognition (Foote & Winter. J Mol Biol, 224: 487-499, 1992). To maintain the affinity of the antibody, it is often necessary to replace certain framework residues by site directed mutagenesis or other recombinant techniques and may be aided by computer modeling of the antigen binding site (Co et al. J Immunol, 152: 2968-2976, 1994).

Humanized forms of antibodies are optionally obtained by resurfacing (Pedersen et al. J Mol Biol, 235: 959-973, 1994). In this approach only the surface residues of a rodent antibody are humanized.

Human antibodies specific to a particular antigen may be identified by a phage display strategy (Jespers et al. Bio/Technology, 12: 899-903, 1994). In one approach, the heavy chain of a rodent antibody directed against a specific antigen is cloned and paired with a repertoire of human light chains for display as Fab fragments on filamentous phage. The phage is selected by binding to antigen. The selected human light chain is subsequently paired with a repertoire of human heavy chains for display on phage, and the phage is again selected by binding to antigen. The result is a human antibody Fab fragment specific to a particular antigen. In another approach, libraries of phage are produced were members display different human antibody fragments (Fab or Fv) on their outer surfaces (Dower et al., WO 91/17271 and McCafferty et al., WO 92/01047). Phage displaying antibodies with a desired specificity are selected by affinity enrichment to a specific antigen. The human Fab or Fv fragment identified from either approach may be recloned for expression as a human antibody in mammalian cells.

Human antibodies are optionally obtained from transgenic animals (U.S. Pat. Nos. 6,150,584; 6,114,598; and 5,770,429). In this approach the heavy chain joining region (JH) gene in a chimeric or germ-line mutant mouse is deleted. Human germ-line immunoglobulin gene array is subsequently transferred to such mutant mice. The resulting transgenic mouse is then capable of generating a full repertoire of human antibodies upon antigen challenge.

Humanized antibodies are typically produced as antigen binding fragments such as Fab, Fab' F(ab')2, Fd, Fv and single domain antibody fragments, or as single chain antibodies in which the heavy and light chains are linked by a spacer. Also, the human or humanized antibodies may exist in monomeric or polymeric form. The humanized antibody optionally comprises one non-human chain and one humanized chain (i.e. one humanized heavy or light chain).

Antibodies, including humanized or human antibodies, are selected from any class of immunoglobulins including: IgM, IgG, IgD, IgA or IgE; and any isotype, including: IgG1, IgG2, IgG3 and IgG4. A chimeric, humanized or human antibody may include sequences from one or more than one isotype or class.

Additionally, antibodies specific for the epitopes described herein are readily isolated by screening antibody phage display libraries. For example, an antibody phage library is optionally screened by using cyclic compounds comprising peptides corresponding to epitopes disclosed herein to identify antibody fragments specific for conformation specific antibodies. Antibody fragments identified are optionally used to produce a variety of recombinant antibodies that are useful with different embodiments described herein. Antibody phage display libraries are commercially available, for example, through Xoma (Berkeley, CA) Methods for screening antibody phage libraries are well known in the art.

A further aspect is antibody and/or binding fragment thereof comprising a light chain variable region and a heavy chain variable region, the heavy chain variable region comprising complementarity determining regions CDR-H1, CDR-H2 and CDR-H3, the light chain variable region comprising complementarity determining region CDR-L1, CDR-L2 and CDR-L3 and with the amino acid sequences of said CDRs comprising the sequences set forth below:

| | | |
|---|---|---|
| CDR-H1 | GYTFTSYW | SEQ ID NO: 17 |
| CDR-H2 | IDPSDSQT | SEQ ID NO: 18 |
| CDR-H3 | SRGGY | SEQ ID NO: 19 |
| CDR-L1 | QDINNY | SEQ ID NO: 20 |
| CDR-L2 | YTS | SEQ ID NO: 21 |
| CDR-L3 | LQYDNLWT | SEQ ID NO: 22 |

In an embodiment, the antibody is a monoclonal antibody. In an embodiment, the antibody is a chimeric antibody such as a humanized antibody comprising the CDR sequences as recited in Table 10.

Also provided in another embodiment, is an antibody comprising the CDRs in Table 10 and a light chain variable region and a heavy chain variable region, optionally in the context of a single chain antibody.

In yet another aspect, the antibody comprises a heavy chain variable region comprises: i) an amino acid sequence as set forth in SEQ ID NO: 24; ii) an amino acid sequence with at least 50%, at least 60%, at least 70%, at least 80%, at least 90% sequence identity to SEQ ID NO: 24, wherein the CDR sequences are as set forth in SEQ ID NO: 17, 18 and 19, or iii) a conservatively substituted amino acid sequence i). In another aspect the antibody comprises a light chain variable region comprising i) an amino acid sequence as set forth in SEQ ID NO: 26, ii) an amino acid sequence with at least 50%, at least 60%, at least 70%, at least 80% or at least 90% sequence identity to SEQ ID NO: 26, wherein the CDR sequences are as set forth in SEQ ID NO: 20, 21 and 22, or iii) a conservatively substituted amino acid sequence of i). In another embodiment, the heavy chain variable region amino acid sequence is encoded by a nucleotide sequence as set out in SEQ ID NO: 23 or a codon degenerate optimized version thereof. In another embodiment, the antibody comprises a light chain variable region amino acid sequence encoded by a nucleotide sequence as set out in SEQ ID NO: 25 or a codon degenerate or optimized version thereof. In an embodiment, the heavy chain variable region comprises an amino acid sequence as set forth in SEQ ID NO: 24

Another aspect is an antibody that specifically binds a same epitope as the antibody with CDR sequences as recited in Table 10.

Another aspect includes an antibody that competes for binding to human A-beta with an antibody comprising the CDR sequences as recited in Table 10.

Competition between antibodies can be determined for example using an assay in which an antibody under test is assessed for its ability to inhibit specific binding of a reference antibody to the common antigen. A test antibody competes with a reference antibody if an excess of a test antibody (e.g., at least a 2 fold, 5, fold, 10 fold or 20 fold) inhibits binding of the reference antibody by at least 50%, at least 75%, at least 80%, at least 90% or at least 95% as measured in a competitive binding assay.

In an embodiment, the antibody is produced using a cyclic compound, optionally a cyclic peptide, described herein.

A further aspect is an antibody conjugated to a therapeutic, detectable label or cytotoxic agent. In an embodiment, the detectable label is a positron-emitting radionuclide. A positron-emitting radionuclide can be used for example in PET imaging.

A further aspect relates to an antibody complex comprising an antibody described herein and/or a binding fragment thereof and oligomeric A-beta.

A further aspect is an isolated nucleic acid encoding an antibody or part thereof described herein.

Nucleic acids encoding a heavy chain or a light chain are also provided, for example encoding a heavy chain comprising CDR-H1, CDR-H2 and/or CDR-H3 regions described herein or encoding a light chain comprising CDR-L1, CDR-L2 and/or CDR-L3 regions described herein.

The present disclosure also provides variants of the nucleic acid sequences that encode for the antibody and/or binding fragment thereof disclosed herein. For example, the variants include nucleotide sequences that hybridize to the nucleic acid sequences encoding the antibody and/or binding fragment thereof disclosed herein under at least moderately stringent hybridization conditions or codon degenerate or optimized sequences In another embodiment, the variant nucleic acid sequences have at least 50%, at least 60%, at least 70%, most preferably at least 80%, even more preferably at least 90% and even most preferably at least 95% sequence identity to nucleic acid sequences encoding SEQ ID NOs: 24 and 26.

In an embodiment, the nucleic acid is an isolated nucleic acid.

Another aspect is an expression cassette or vector comprising the nucleic acid herein disclosed. In an embodiment, the vector is an isolated vector.

The vector can be any vector, including vectors suitable for producing an antibody and/or binding fragment thereof or expressing a peptide sequence described herein.

The nucleic acid molecules may be incorporated in a known manner into an appropriate expression vector which ensures expression of the protein. Possible expression vectors include but are not limited to cosmids, plasmids, or modified viruses (e.g. replication defective retroviruses, adenoviruses and adeno-associated viruses). The vector should be compatible with the host cell used. The expression vectors are "suitable for transformation of a host cell", which means that the expression vectors contain a nucleic acid molecule encoding the peptides corresponding to epitopes or antibodies described herein.

In an embodiment, the vector is suitable for expressing for example single chain antibodies by gene therapy. The vector can be adapted for specific expression in neural tissue, for example using neural specific promoters and the like. In an embodiment, the vector comprises an IRES and allows for expression of a light chain variable region and a heavy chain variable region. Such vectors can be used to deliver antibody in vivo.

Suitable regulatory sequences may be derived from a variety of sources, including bacterial, fungal, viral, mammalian, or insect genes.

Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

In an embodiment, the regulatory sequences direct or increase expression in neural tissue and/or cells.

In an embodiment, the vector is a viral vector.

The recombinant expression vectors may also contain a marker gene which facilitates the selection of host cells transformed, infected or transfected with a vector for expressing an antibody or epitope peptide described herein.

The recombinant expression vectors may also contain expression cassettes which encode a fusion moiety (i.e. a "fusion protein") which provides increased expression or stability of the recombinant peptide; increased solubility of the recombinant peptide; and aid in the purification of the target recombinant peptide by acting as a ligand in affinity purification, including for example tags and labels described herein. Further, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMAL (New England Biolabs, Beverly, MA) and pRIT5 (Pharmacia, Piscataway, NJ) which fuse glutathione S-transferase (GST), maltose E binding protein, or protein A, respectively, to the recombinant protein.

Systems for the transfer of genes for example into neurons and neural tissue both in vitro and in vivo include vectors based on viruses, most notably Herpes Simplex Virus, Adenovirus, Adeno-associated virus (AAV) and retroviruses including lentiviruses. Alternative approaches for gene delivery include the use of naked, plasmid DNA as well as liposome-DNA complexes. Another approach is the use of AAV plasmids in which the DNA is polycation-condensed and lipid entrapped and introduced into the brain by intracerebral gene delivery (Leone et al. US Application No. 2002076394).

Accordingly, in another aspect, the compounds, immunogens, nucleic acids, vectors and antibodies described herein may be formulated in vesicles such as liposomes, nanoparticles, and viral protein particles, for example for delivery of antibodies, compounds, immunogens and nucleic acids described herein. In particular synthetic polymer vesicles, including polymersomes, can be used to administer antibodies.

Also provided in another aspect is a cell, optionally an isolated and/or recombinant cell, expressing an antibody described herein or comprising a vector herein disclosed.

The recombinant cell can be generated using any cell suitable for producing a polypeptide, for example suitable for producing an antibody and/or binding fragment thereof. For example to introduce a nucleic acid (e.g. a vector) into a cell, the cell may be transfected, transformed or infected, depending upon the vector employed.

Suitable host cells include a wide variety of prokaryotic and eukaryotic host cells. For example, the proteins described herein may be expressed in bacterial cells such as *E. coli*, insect cells (using baculovirus), yeast cells or mammalian cells.

In an embodiment, the cell is a eukaryotic cell selected from a yeast, plant, worm, insect, avian, fish, reptile and mammalian cell.

In another embodiment, the mammalian cell is a myeloma cell, a spleen cell, or a hybridoma cell.

In an embodiment, the cell is a neural cell.

Yeast and fungi host cells suitable for expressing an antibody or peptide include, but are not limited to *Saccharomyces cerivisiae, Schizosaccharomyces pombe*, the genera *Pichia* or *Kluyveromyces* and various species of the genus *Aspergillus*. Examples of vectors for expression in yeast *S. cerivisiae* include pYepSec1, pMFa, pJRY88, and pYES2 (Invitrogen Corporation, San Diego, CA). Protocols for the transformation of yeast and fungi are well known to those of ordinary skill in the art.

Mammalian cells that may be suitable include, among others: COS (e.g., ATCC No. CRL 1650 or 1651), BHK (e.g. ATCC No. CRL 6281), CHO (ATCC No. CCL 61), HeLa (e.g., ATCC No. CCL 2), 293 (ATCC No. 1573) and NS-1 cells. Suitable expression vectors for directing expression in mammalian cells generally include a promoter (e.g., derived from viral material such as polyoma, Adenovirus 2, cytomegalovirus and Simian Virus 40), as well as other transcriptional and translational control sequences. Examples of mammalian expression vectors include pCDM8 and pMT2PC.

A further aspect is a hybridoma producing an antibody specific for an epitope described herein.

IV. Compositions

A further aspect is a composition comprising a compound, immunogen, nucleic acid, vector or antibody described herein.

In an embodiment, the composition comprises a diluent.

Suitable diluents for nucleic acids include but are not limited to water, saline solutions and ethanol.

Suitable diluents for polypeptides, including antibodies or fragments thereof and/or cells include but are not limited to saline solutions, pH buffered solutions and glycerol solutions or other solutions suitable for freezing polypeptides and/or cells.

In an embodiment, the composition is a pharmaceutical composition comprising any of the peptides, immunogens, antibodies, nucleic acids or vectors disclosed herein, and optionally comprising a pharmaceutically acceptable carrier.

The compositions described herein can be prepared by per se known methods for the preparation of pharmaceutically acceptable compositions that can be administered to subjects, optionally as a vaccine, such that an effective quantity of the active substance is combined in a mixture with a pharmaceutically acceptable vehicle.

Pharmaceutical compositions include, without limitation, lyophilized powders or aqueous or non-aqueous sterile injectable solutions or suspensions, which may further contain antioxidants, buffers, bacteriostats and solutes that render the compositions substantially compatible with the tissues or the blood of an intended recipient. Other components that may be present in such compositions include water, surfactants (such as Tween), alcohols, polyols, glycerin and vegetable oils, for example. Extemporaneous injection solutions and suspensions may be prepared from sterile powders, granules, tablets, or concentrated solutions or suspensions. The composition may be supplied, for example but not by way of limitation, as a lyophilized powder which is reconstituted with sterile water or saline prior to administration to the patient.

Pharmaceutical compositions may comprise a pharmaceutically acceptable carrier. Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1(2,3-dioleyloxy)propyl)N, N,N-trimethylammonium chloride (DOTMA), diolesylphosphotidyl-ethanolamine (DOPE), and liposomes. Such compositions should contain a therapeutically effective amount of the compound, together with a suitable amount of carrier so as to provide the form for direct administration to the patient.

The composition may be in the form of a pharmaceutically acceptable salt which includes, without limitation, those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

In an embodiment comprising a compound or immunogen described herein, the composition comprises an adjuvant.

Adjuvants that can be used for example, include intrinsic adjuvants (such as lipopolysaccharides) that normally are the components of killed or attenuated bacteria used as vaccines. Extrinsic adjuvants are immunomodulators which are typically non-covalently linked to antigens and are formulated to enhance the host immune responses. Aluminum hydroxide, aluminum sulfate and aluminum phosphate (collectively commonly referred to as alum) are routinely used as adjuvants. A wide range of extrinsic adjuvants can provoke potent immune responses to immunogens. These include saponins such as Stimulons (QS21, Aquila, Worcester, Mass.) or particles generated therefrom such as ISCOMs and (immunostimulating complexes) and ISCOMATRIX, complexed to membrane protein antigens (immune stimulating complexes), pluronic polymers with mineral oil, killed mycobacteria and mineral oil, Freund's complete adjuvant, bacterial products such as muramyl dipeptide (MDP) and lipopolysaccharide (LPS), as well as lipid A, and liposomes.

In an embodiment, the adjuvant is aluminum hydroxide. In another embodiment, the adjuvant is aluminum phosphate. Oil in water emulsions include squalene; peanut oil; MF59 (WO 90/14387); SAF (Syntex Laboratories, Palo Alto, Calif.); and Ribi™ (Ribi Immunochem, Hamilton, Mont.). Oil in water emulsions may be used with immunostimulating agents such as muramyl peptides (for example, N-acetylmuramyl-L-threonyl-D-isoglutamine (thr-MDP), -acetyl-normuramyl-L-alanyl-D-isoglutamine (nor-MDP), N-acetylmuramyl-L-alanyl-D-isoglutamyl-L-alanine-2-(1'-2'dipalmitoyl-sn-glycero-3-hydroxyphosphoryloxy)-ethyl-amine (MTP-PE), N-acetylglucsaminyl-N-acetylmuramyl-L-Al-D-isoglu-L-Ala-dipalmitoxy propylamide (DTP-DPP) theramide (TM)), or other bacterial cell wall components.

The adjuvant may be administered with an immunogen as a single composition. Alternatively, an adjuvant may be administered before, concurrent and/or after administration of the immunogen.

Commonly, adjuvants are used as a 0.05 to 1.0 percent solution in phosphate-buffered saline. Adjuvants enhance the immunogenicity of an immunogen but are not necessarily immunogenic themselves. Adjuvants may act by retaining the immunogen locally near the site of administration to produce a depot effect facilitating a slow, sustained release of immunogen to cells of the immune system. Adjuvants can also attract cells of the immune system to an immunogen depot and stimulate such cells to elicit immune responses. As such, embodiments may encompass compositions further comprising adjuvants.

Adjuvants for parenteral immunization include aluminum compounds (such as aluminum hydroxide, aluminum phosphate, and aluminum hydroxy phosphate). The antigen can be precipitated with, or adsorbed onto, the aluminum compound according to standard protocols. Other adjuvants such as RIBI (ImmunoChem, Hamilton, MT) can also be used in parenteral administration.

Adjuvants for mucosal immunization include bacterial toxins (e.g., the cholera toxin (CT), the *E. coli* heat-labile toxin (LT), the *Clostridium difficile* toxin A and the pertussis toxin (PT), or combinations, subunits, toxoids, or mutants thereof). For example, a purified preparation of native cholera toxin subunit B (CTB) can be of use. Fragments, homologs, derivatives, and fusion to any of these toxins are also suitable, provided that they retain adjuvant activity. Preferably, a mutant having reduced toxicity is used. Suitable mutants have been described (e.g., in WO 95/17211 (Arg-7-Lys CT mutant), WO 96/6627 (Arg-192-Gly LT mutant), and WO 95/34323 (Arg-9-Lys and Glu-129-Gly PT mutant)). Additional LT mutants that can be used in the methods and compositions include, for example Ser-63-Lys, Ala-69-Gly, Glu-110-Asp, and Glu-112-Asp mutants. Other adjuvants (such as a bacterial monophosphoryl lipid A (MPLA) of various sources (e.g., *E. coli, Salmonella minnesota, Salmonella typhimurium,* or *Shigella flexneri,* saponins, or polylactide glycolide (PLGA) microspheres) can also be used in mucosal administration.

Other adjuvants include cytokines such as interleukins for example IL-1, IL-2 and IL-12, chemokines, for example CXCL10 and CCL5, macrophage stimulating factor, and/or tumor necrosis factor. Other adjuvants that may be used include CpG oligonucleotides (Davis. Curr Top Microbiol Immunol., 247:171-183, 2000).

Oil in water emulsions include squalene; peanut oil; MF59 (WO 90/14387); SAF (Syntex Laboratories, Palo Alto, Calif.); and Ribi™ (Ribi Immunochem, Hamilton, Mont.). Oil in water emulsions may be used with immunostimulating agents such as muramyl peptides (for example, N-acetylmuramyl-L-threonyl-D-isoglutamine (thr-MDP), -acetyl-normuramyl-L-alanyl-D-isoglutamine (nor-MDP), N-acetylmuramyl-L-alanyl-D-isoglutamyl-L-alanine-2-(1'-2'dipalmitoyl-sn-glycero-3-hydroxyphosphoryloxy)-ethylamine (MTP-PE), N-acetylglucsaminyl-N-acetylmuramyl-L-Al-D-isoglu-L-Ala-dipalmitoxy propylamide (DTP-DPP) theramide (TM)), or other bacterial cell wall components.

Adjuvants useful for both mucosal and parenteral immunization include polyphosphazene (for example, WO 95/2415), DC-chol (3 b-(N—(N',N'-dimethyl aminomethane)-carbamoyl) cholesterol (for example, U.S. Pat. No. 5,283,185 and WO 96/14831) and QS-21 (for example, WO 88/9336).

An adjuvant may be coupled to an immunogen for administration. For example, a lipid such as palmitic acid, may be coupled directly to one or more peptides such that the change in conformation of the peptides comprising the immunogen does not affect the nature of the immune response to the immunogen.

In an embodiment, the composition comprises an antibody described herein. In another embodiment, the composition comprises an antibody described herein and a diluent. In an embodiment, the composition is a sterile composition.

V. Kits

A further aspect relates to a kit comprising i) an antibody and/or binding fragment thereof, ii) a nucleic acid, iii) peptide or immunogen, iv) composition or v) recombinant cell described herein, comprised in a vial such as a sterile vial or other housing and optionally a reference agent and/or instructions for use thereof.

In an embodiment, the kit further comprises one or more of a collection vial, standard buffer and detection reagent.

VI. Methods

Included are methods for making and using the compounds, immunogens and antibodies described herein.

In particular, provided are methods of making an antibody specific and/or selective for a conformational epitope of HDSG (SEQ ID NO: 1) or related epitope comprising administering to a subject, optionally a non-human subject, a conformationally restricted compound comprising an epitope sequence described herein, optionally cyclic compound comprising HDSG (SEQ ID NO: 1) or related epitope, and isolating antibody producing cells or antibodies that specifically or selectively bind the cyclic compound and optionally i) specifically or selectively bind synthetic and/or native oligomers and/or that have no or negligible senile plaque binding in situ tissue samples or no or negligible binding to a corresponding linear peptide. The cyclic compound can for example comprise any of the "epitopes" described herein containing cyclic compounds described herein.

In an embodiment, the method is for making a monoclonal antibody using for example a method as described herein.

In an embodiment, the method is for making a humanized antibody using for example a method described herein.

Antibodies produced using a cyclic compound are selected as described herein and in the Examples. In an embodiment, the method comprises isolating antibodies that specifically or selectively bind cyclic peptide over linear peptide, are specific for the epitope sequence, specifically bind oligomer and/or lack or negligibly bind plaque in situ and/or corresponding linear peptide, optionally using a method described herein.

A further aspect provides a method of detecting whether a biological sample comprises A-beta, the method comprising contacting the biological sample with an antibody described herein and detecting the presence of any antibody complex. In an embodiment, the method is for detecting whether a biological sample comprises A-beta wherein at least H, D and/or S is in an alternate conformation than occupied by H, D and/or S in a non-oligomeric conformation.

In an embodiment the method is for detecting whether the biologic sample comprises oligomeric A-beta.

In an embodiment, the method comprises:

a. contacting the biologic sample with an antibody described herein that is specific and/or selective for A-beta oligomer herein under conditions permissive to produce an antibody:A-beta oligomer complex; and b. detecting the presence of any complex;

wherein the presence of detectable complex is indicative that the sample may contain A-beta oligomer.

In an embodiment, the level of complex formed is compared to a test antibody such as a suitable Ig control or irrelevant antibody.

In an embodiment, the detection is quantitated and the amount of complex produced is measured. The measurement can for example be relative to a standard.

In an embodiment, the measured amount is compared to a control.

In another embodiment, the method comprises:

(a) contacting a biological sample of said subject with an antibody described herein, under conditions permissive to produce an antibody-antigen complex;

(b) measuring the amount of the antibody-antigen complex in the test sample; and (c) comparing the amount of antibody-antigen complex in the test sample to a control;

wherein detecting antibody-antigen complex in the biological sample as compared to the control indicates that the sample comprises A-beta.

The control can be a sample control (e.g. from a subject without AD, or from a subject with a particular form of AD, mild, moderate or advanced), or be a previous sample from the same subject for monitoring changes in A-beta oligomer levels in the subject.

In an embodiment, an antibody described herein is used.

In an embodiment, the antibody specifically and/or selectively recognizes a conformation of A-beta comprising a HDSG (SEQ ID NO: 1) or related conformational epitope, and detecting the antibody antigen complex in the biological sample is indicative that sample comprises A-beta oligomer.

In an embodiment, the sample is a biological sample. In an embodiment, the sample comprises brain tissue or an extract thereof and/or CSF. In an embodiment, the sample comprises whole blood, plasma or serum. In an embodiment, the sample is obtained from a human subject. In an embodiment, the subject is suspected of, at a risk of or has AD.

A number of methods can be used to detect an A-beta: antibody complex and thereby determine if A-beta comprising a HDSG (SEQ ID NO: 1) or related conformational epitope and/or A-beta oligomers is present in the biological sample using the antibodies described herein, including immunoassays such as flow cytometry, immunoblots, ELISA, and immunoprecipitation followed by SDS-PAGE, and immunocytochemistry.

As described in the Examples surface plasmon resonance technology can be used to assess conformation specific binding. If the antibody is labelled or a detectably labelled secondary antibody specific for the complex antibody is used, the label can be detected. Commonly used reagents include fluorescent emitting and HRP labelled antibodies. In quantitative methods, the amount of signal produced can be measured by comparison to a standard or control. The measurement can also be relative.

A further aspect includes a method of measuring a level of- or imaging A-beta in a subject or tissue, optionally where the A-beta to be measured or imaged is oligomeric A-beta. In an embodiment, the method comprises administering to a subject at risk or suspected of having or having AD, an antibody conjugated to a detectable label; and detecting the label, optionally quantitatively detecting the label. The label in an embodiment is a positron emitting radionuclide which can for example be used in PET imaging.

A further aspect includes a method of inducing an immune response in a subject, comprising administering to the subject a compound described herein, optionally a cyclic compound comprising HDSG (SEQ ID NO:1) or a related epitope peptide sequence, an immunogen and/or composition comprising said compound or said immunogen; and optionally isolating cells and/or antibodies that specifically or selectively bind the A-beta peptide in the compound or immunogen administered. In an embodiment, the composition is a pharmaceutical composition comprising the compound or immunogen in admixture with a pharmaceutically acceptable, diluent or carrier.

In an embodiment, the subject is a non-human subject such as a rodent. Antibody producing cells generated are used in an embodiment to produce a hybridoma cell line.

In an embodiment, the immunogen administered comprises a compound illustrated in FIG. 11B.

Figure 19:
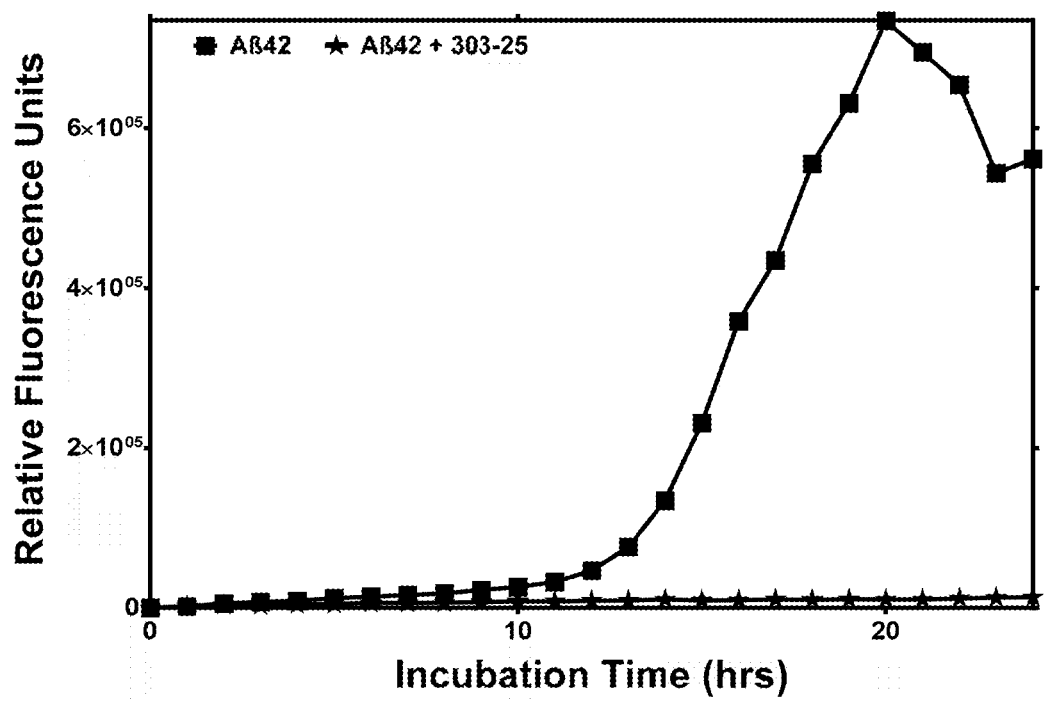
FIG. 19: A plot showing propagation of A-beta aggregation in vitro in the presence or absence of a representative antibody raised using a cyclic peptide comprising HDSG (SEQ ID NO:1).

It is demonstrated herein that antibodies raised against cyclo(CGHDSGG), can specifically and/or selectively bind A-beta oligomers and lack A-beta plaque staining. Oligomeric A-beta species are believed to be the toxic propagating species in AD. Further as shown in FIG. 19, antibody raised using cyclo(CGHDSGG) (SEQ ID NO: 2) and specific for oligomers, inhibited A-beta aggregation and A-beta oligomer propagation. Accordingly, also provided are methods of inhibiting A-beta oligomer propagation, the method comprising contacting a cell or tissue expressing A-beta with or administering to a subject in need thereof an effective amount of an A-beta oligomer specific or selective antibody described herein to inhibit A-beta aggregation and/or oligomer propagation. In vitro the assay can be monitored as described in Example 10.

The antibodies may also be useful for treating AD and/or other A-beta amyloid related diseases. For example, variants of Lewy body dementia and in inclusion body myositis (a muscle disease) exhibit similar plaques as AD in the brain and muscle respectively, and A-beta can also form in aggregates implicated in cerebral amyloid angiopathy. Moreover, "mixed" pathology in neurodegenerative diseases (including Parkinson's disease and frontotemporal dementia) is recognized in which features of AD pathology can be observed without a frank AD clinical syndrome. As mentioned, antibodies raised to cyclo(CGHDSGG) (SEQ ID NO: 2) bind oligomeric A-beta which is believed to be a toxigenic species of A-beta in AD and inhibit formation of toxigenic A-beta oligomers.

Accordingly a further aspect is a method of treating AD and/or other A-beta amyloid related diseases, the method comprising administering to a subject in need thereof i) an effective amount of an antibody described herein, optionally an A-beta oligomer specific or selective or a pharmaceutical composition comprising said antibody; or 2) administering an isolated cyclic compound comprising HDSG (SEQ ID NO:1) or a related epitope sequence or immunogen or pharmaceutical composition comprising said cyclic compound, to a subject in need thereof.

In an embodiment, a biological sample from the subject to be treated is assessed for the presence or levels of A-beta using an antibody described herein. In an embodiment, a subject with detectable A-beta levels (e.g. A-beta antibody complexes measured in vitro or measured by imaging) is treated with the antibody.

The antibody and immunogens can for example be comprised in a pharmaceutical composition as described herein, and formulated for example in vesicles for improving delivery.

One or more antibodies targeting HDSG (SEQ ID NO:1) and/or related antibodies can be administered in combination. In addition the antibodies disclosed herein can be administered with one or more other treatments such as a beta-secretase inhibitor or a cholinesterase inhibitor.

In an embodiment, the antibody is a conformation specific/selective antibody, optionally that specifically or selectively binds A-beta oligomer.

Also provided are uses of the compositions, antibodies, isolated peptides, immunogens and nucleic acids for treating AD.

The compositions, compounds, antibodies, isolated peptides, immunogens and nucleic acids, vectors etc. described herein can be administered for example, by parenteral, intravenous, subcutaneous, intramuscular, intracranial, intraventricular, intrathecal, intraorbital, ophthalmic, intraspinal, intracisternal, intraperitoneal, intranasal, aerosol or oral administration.

In certain embodiments, the pharmaceutical composition is administered systemically.

In other embodiments, the pharmaceutical composition is administered directly to the brain or other portion of the CNS. For example such methods include the use of an implantable catheter and a pump, which would serve to discharge a pre-determined dose through the catheter to the infusion site. A person skilled in the art would further recognize that the catheter may be implanted by surgical techniques that permit visualization of the catheter so as to position the catheter adjacent to the desired site of administration or infusion in the brain. Such techniques are described in Elsberry et al. U.S. Pat. No. 5,814,014 "Techniques of Treating Neurodegenerative Disorders by Brain Infusion", which is herein incorporated by reference. Also contemplated are methods such as those described in US patent application 20060129126 (Kaplitt and During "Infusion device and method for infusing material into the brain of a patient". Devices for delivering drugs to the brain and other parts of the CNS are commercially available (eg. SynchroMed® EL Infusion System; Medtronic, Minneapolis, Minnesota).

In another embodiment, the pharmaceutical composition is administered to the brain using methods such as modifying the compounds to be administered to allow receptor-mediated transport across the blood brain barrier.

Other embodiments contemplate the co-administration of the compositions, compounds, antibodies, isolated peptides, immunogens and nucleic acids described herein with biologically active molecules known to facilitate the transport across the blood brain barrier.

Also contemplated in certain embodiments, are methods for administering the compositions, compounds, antibodies, isolated peptides, immunogens and nucleic acids described herein across the blood brain barrier such as those directed at transiently increasing the permeability of the blood brain barrier as described in U.S. Pat. No. 7,012,061 "Method for increasing the permeability of the blood brain barrier", herein incorporated by reference.

A person skilled in the art will recognize the variety of suitable methods for administering the compositions, compounds, antibodies, isolated peptides, immunogens and nucleic acids described herein directly to the brain or across the blood brain barrier and be able to modify these methods in order to safely administer the products described herein.

The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

Collective Coordinates Predictions

A method for predicting misfolded epitopes is provided by a method referred to as "Collective Coordinates biasing" which is described in U.S. Patent Application Ser. No. 62/253,044, SYSTEMS AND METHODS FOR PREDICTING MISFOLDED PROTEIN EPITOPES BY COLLECTIVE COORDINATE BIASING filed Nov. 9, 2015, and is incorporated herein by reference. As described therein, the method uses molecular-dynamics-based simulations which impose a global coordinate bias on a protein (or peptide-aggregate) to force the protein (or peptide-aggregate) to misfold and then predict the most likely unfolded regions of the partially unstructured protein (or peptide aggregate). Biasing simulations were performed and the solvent accessible surface area (SASA) corresponding to each residue index (compared to that of the initial structure of the protein under consideration). SASA represents a surface area that is accessible to H2O. A positive change in SASA (compared to that of the initial structure of the protein under consideration) may be considered to be indicative of unfolding in the region of the associated residue index. The method was applied to three A-beta strains, each with its own morphology: a three-fold symmetric structure of Aβ-40 peptides (or monomers) (PDB entry 2M4J), a two-fold symmetric structure of Aβ-40 monomers (PDB entry 2LMN), and a single-chain, parallel in-register (e.g. a repeated beta sheet where the residues from one chain interact with the same residues from the neighboring chains) structure of Aβ-42 monomers (PDB entry 2MXU).

Simulations were performed for each initial structure using the collective coordinates method as described in U.S. Patent Application Ser. No. 62/253,044 and the CHARMM force-field parameters described in: K. Vanommeslaeghe, E. Hatcher, C. Acharya, S. Kundu, S. Zhong, J. Shim, E. Darian, O. Guvench, P. Lopes, I. Vorobyov, and A. D. Mackerell. Charmm general force field: A force field for drug-like molecules compatible with the charmm all-atom additive biological force fields. *Journal of Computational Chemistry*, 31(4):671-690, 2010; and P. Bjelkmar, P. Larsson, M. A. Cuendet, B. Hess, and E. Lindahl. Implementation of the CHARMM force field in GROMACS: analysis of protein stability effects from correlation maps, virtual interaction sites, and water models. *J. Chem. Theo. Comp.*, 6:459-466, 2010, both of which are hereby incorporated herein by reference, with TIP3P water.

Epitopes predicted using this method are described in Example 2.

Example 2

I. Collective Coordinates Predictions

The epitope HDSG (SEQ ID NO:1) emerges as a predicted epitope from strain 2M4J from the collective coordinates approach described in Example 1. In several other strains of fibril, this region remains disordered and so has no structure in the PDB entry. For example in 2LMN, HDS is unstructured and so coordinates for these residues are not present in the PDB structure, in 2LMP HDS is unstructured in the PDB, and in 2MXU HDSG (SEQ ID NO: 1) is unstructured in the PDB. The corresponding FIG. showing the predicted epitope is in FIG. 1. For fibril structure 2M4J, 2 sequences bracketing HDSG (SEQ ID NO: 1) from the left and right, RHDSG (SEQ ID NO: 5) and HDSGY (SEQ ID NO: 4), are predicted; residues R5 and Y10 each emerge from one prediction, while residues HDSG (SEQ ID NO: 1) emerge from 2 predictions, and so are treated as a putative consensus sequence between these two predictions.

II. Conformation Specific Epitopes

As mentioned herein and shown in FIG. 1, the HDSG (SEQ ID NO: 1) epitope emerges as a prediction upon adding denaturing stress to the fibril PDB structure 2M4J. HDSGY (SEQ ID NO: 4) and RHSDG (SEQ ID NO: 5) also are predicted.

Aβ is a peptide of length 36-43 amino acids that results from the cleavage of amyloid precursor protein (APP) by gamma secretase. In AD patients, it is present in as multiple conformation monomers, insoluble fibrils, and in soluble oligomers. Aβ fibril is the main component of the senile plaques found in the brains of AD patients.

In monomer form, Aβ exists as an unstructured polypeptide chain. In fibril form, Aβ can aggregate into distinct morphologies, often referred to as strains. Several of these structures have been determined by solid-state NMR—some fibril structures have been obtained from in vitro studies, and others obtained by seeding fibrils using amyloid plaques taken from AD patients.

The oligomer is suggested to be a toxic and propagative species of the peptide.

A prerequisite for the generation of oligomer-specific antibodies is the identification of targets on Aβ peptide that are not present on or are less favourable in either the monomer or fibril conformations. These oligomer-specific epitopes would not differ in primary sequence from the corresponding segment in monomer or fibril, however they would be conformationally distinct in the context of the oligomer. That is, they would present a distinct conformation in the oligomer that would not be present in the monomer or fibril.

The structure of the oligomer has not been determined to date, moreover, NMR evidence indicates that the oligomer exists not in a single well-defined structure, but in a conformationally-plastic, malleable structural ensemble with limited regularity. Moreover, the concentration of oligomer species is far below either that of the monomer or fibril (estimates vary but on the order of 1000-fold below or more), making this target elusive.

Antibodies directed either against contiguous strands of primary sequence (e.g., linear sequence), or against fibril structures, may suffer from several problems limiting their efficacy. Antibodies raised to linear peptide regions tend not to be selective for oligomer, and thus bind to monomer as well. Because the concentration of monomer is substantially higher than that of oligomer, such antibody therapeutics may suffer from "target distraction", primarily binding to monomer and promoting clearance of functional Aβ, rather than selectively targeting and clearing oligomeric species. Antibodies raised to amyloid inclusions bind primarily to fibril, and have resulted in amyloid related imaging abnormalities (ARIA), including signal changes thought to represent vasogenic edema and/or microhemorrhages.

To develop antibodies selective for oligomeric forms of Aβ, a region that may be disrupted in the fibril was identified. Without wishing to be bound to theory, it was hypothesized that disruptions in the context of the fibril may be exposed on the surface of the oligomer. On oligomers however, these sequence regions may be exposed in conformations distinct from either that of the monomer and/or that of the fibril. For example, being on the surface, they may be exposed in turn regions that have higher curvature, higher exposed surface area, and different dihedral angle distribution than the corresponding quantities exhibit in either the fibril or the monomer.

Cyclic compounds comprising HDSG (SEQ ID NO: 1) are described herein and shown in FIG. 11B. The cyclic compounds have been designed to satisfy one or more of the above criteria of higher curvature, higher exposed surface area, and alternative dihedral angle distributions.

A potential benefit of identifying regions prone to disruption in the fibril is that it may identify regions involved in secondary nucleation processes where fibrils may act as a catalytic substrate to nucleate oligomers from monomers [3]. Regions of fibril with exposed side chains may be more likely to engage in aberrant interactions with nearby monomer, facilitating the accretion of monomers; such accreted monomers would then experience an environment of effectively increased concentration at or near the surface of the fibril, and thus be more likely to form multimeric aggregates including oligomers. Aged or damaged fibril with exposed regions of Aβ may enhance the production of toxic oligomer, and antibodies directed against these disordered regions on the fibril could be effective in blocking such propagative mechanisms.

III. Curvature of the Cyclic Peptide

The curvature profile of the cyclic peptide CGHDSGG (SEQ ID NO:2) differentiates cyclic HDSG (SEQ ID NO:1) from either the linear peptide or the fibril. The curvature profiles are shown in FIG. 2. The histidine residue at position 6 has a lower curvature than either the linear peptide or the fibril. The linear peptide tends to bend the backbone compared to the conformations explored by either the cyclic peptide or fibril. On the other hand, the aspartic acid residue D7 and the serine residue S8 have a higher curvature in the cyclic peptide compared to the curvature of those residues in either the linear peptide or the fibril. The glycine residue (G) in the cyclic peptide has somewhat higher curvature than that in the fibril but a somewhat lower curvature than that in the linear peptide. These results imply that an antibody directed against the cyclic peptide could show selectivity for a species presenting a different conformational ensemble than that of either the monomer or fibril.

For the plots of curvature, and dihedral angle distributions discussed herein, the data are obtained from equilibrium simulations in explicit solvent (TIP3P) using the Charmm27. The simulation time and number of configurations for each ensemble are as follows. Cyclic peptide ensemble: simulation time 10 ns, containing 1001 frames; linear peptide ensemble: simulation time 10 ns, containing 1001 frames; 2M4J ensemble: 680 ps, containing 69 frames.

Because the curvature of the cyclic epitope has a different profile than either the linear peptide or fibril, it is expected that the corresponding stretch of amino acids on an oligomer containing these residues would have a backbone orientation that is distinct from that in the fibril or monomer. However the degree of curvature would not be unphysical—values of curvature characterizing the cyclic peptide are obtained in several locations of the fibril.

Numerical values of the curvature for residues H, D, S and G are given in Table 4. Note that the curvature for both the linear and cyclic peptides is generally larger for HDSG (SEQ ID NO: 1) than the curvature of those residues in the fibril, though not significantly larger than the curvature in the fibril overall. This is largely due to the fact that HDSG (SEQ ID NO: 1) is in a relatively extended beta strand conformation in the fibril structure 2M4J, and suggests that antibodies raised to either the cyclic or linear peptides may be conformationally selective against the fibril, i.e. with low affinity to the fibril.

IV. Dihedral Angle Distributions

Further computational support for the identification of an oligomer-selective epitope, is provided by both the side chain dihedral angle distributions, and the Ramachandran φ and ψ distributions for the backbone dihedral angles in the cyclic peptide a proxy for an exposed epitope in the oligomer—are for many angles substantially different from the corresponding distributions in either the fibril or monomer.

The side-chain dihedral distributions were examined for residues H, D, and S. The distributions of the $C$-$C_\alpha$-$C_\beta$-$C_\gamma$ and $N$-$C_\alpha$-$C_\beta$-$C_\gamma$ dihedral angles for H6 are different for the cyclic peptide than for either the monomer or fibril distributions (FIG. 3). The probability that the linear peptide occupies a dihedral within the range of almost all (90%) of the cyclic peptide dihedral angles is 36% for either of the two above dihedrals, while the probability that the peptide in the context of the fibril occupies a dihedral within the range of almost all (90%) of the cyclic peptide dihedral angles is only 13% for either of the two above dihedrals. The other dihedral angles have corresponding probabilities of approximately 30% or more for either the fibril or monomer ensembles. In the following descriptions and FIG.s CA, Ca, or $C_\alpha$ are alternatively used to describe the C-alpha atom, and similarly for CB, Cb, and $C_\beta$, and so on.

The dihedral distributions are shown for D7 in FIG. 4. The probability that the linear peptide occupies a dihedral within the range of almost all (90%) of the cyclic peptide dihedral angles is as follows for the dihedral angles of D7:

C-CA-CB-CG: 12%
N-CA-CB-CG: 19%
O-C-CA-CB: 15%

The probability that the peptide in the context of the fibril occupies a dihedral within the range of almost all (90%) of the cyclic peptide dihedral angles is as follows for the dihedral angles of D7:

C-CA-CB-CG: 30%
N-CA-CB-CG: 49%
O-C-CA-CB: 6%

The dihedral distributions are shown for S8 in FIG. 5. One can see that the dihedral angle distributions are substantially different for the dihedral angles in the cyclic conformational ensemble then they are in either the linear or fibril ensembles. The probability that the linear peptide occupies a dihedral within the range of almost all (90%) of the cyclic peptide dihedral angles is as follows for the dihedral angles of S8:

C-CA-CB-OG: 92% (this indicates substantial overlap, but the weights of the peaks having overlap in FIG. 5 are substantially different, as can be seen from FIG. 5, indicating that the preferred dihedral angles may still be different.
N-CA-CB-OG: 84% (a similar comment applies to this dihedral angle as does for C-CA-CB-OG above)
O-C-CA-CB: 19%

The probability that the peptide in the context of the fibril occupies a dihedral within the range of almost all (90%) of the cyclic peptide dihedral angles is as follows for the dihedral angles of S8:

C-CA-CB-OG: 30%
N-CA-CB-OG: 28%
O-C-CA-CB: 25%

According to the above analysis of side chain dihedral angle distributions, 7D AND 8S are the residues showing the largest discrepancy from the linear peptide and fibril ensembles. 7D and/or 8S may be key residues on the epitope conferring conformational selectivity.

Based on the data shown in FIGS. 3-5, Table 1 lists the peak values of the dihedral angle distributions, for those dihedral angles whose distributions that show significant differences between the cyclic peptide and other species. Column 1 in Table 1 is the specific dihedral considered, column 2 is the peak value of the dihedral distribution for that angle in the context of the linear peptide CGHDSGG (SEQ ID NO: 2), column 3 is the peak value of the dihedral distribution for that angle in the context of the cyclic peptide CGHDSGG (SEQ ID NO: 2), column 4 is the difference of the peak values of the dihedral distributions for the linear and cyclic peptides, and column 5 is the peak value of the dihedral distribution for the peptide HDSG (SEQ ID NO: 1) in the context of the fibril structure 2M4J.

TABLE 1

Peak Values of the Dihedral Angle Distributions

| Dihedral angle | linear | cyclic | Difference (linear-cyclic) | fibril |
|---|---|---|---|---|
| 6H: O-C-CA-CB | −57.5, 97.5 | 107.5 | −165, −10 | 97.5 |
| 6H: CA-CB-CG-CD2 | −107.5, 97.5 | −82.5 | −25, 180 | −107.5 |
| 6H: CA-CB-CG-ND1 | 77.5, −72.5 | 102.5 | −25, −175 | 77.5, −77.5 |
| 6H: N-CA-CB-CG | −67.5, 67.5, 180 | −62.5 | −5, 130, −117.5 | 67.5, 180 |
| 6H: C-CA-CB-CG | 62.5, −57.5, 180 | −57.5 | 120, 0, −122.5 | −57.5, 180 |
| 7D: C-CA-CB-CG | −77.5, 72.5, 172.5 | 172.5 | 97.5, −100, 0 | 72.5, −77.5, 180 |
| 7D: N-CA-CB-CG | 57.5, −62.5, −162.5 | −62.5 | 120, 0, −100 | −62.5, 52.5 |
| 7D: O-C-CA-CB | 102.5 | −97.5 | −160 | 97.5 |
| 8S: N-CA-CB-OG | −172.5 | −62.5 | −110 | 62.5 |
| 8S: C-CA-CB-OG | 67.5 | 180, 62.5 | −112.5, 5 | −72.5, 67.5 |
| 8S: O-C-CA-CB | 82.5 | −102.5 | −175 | 117.5 |

The cyclic peptide is generally more rigid than the linear peptide, particularly for H6. Moreover, residue H6 is more rigid in the cyclic peptide than in the fibril conformations. This suggests there may be a well-defined antigenic profile particularly around H6. The profile does have overlap however with the linear and fibril ensembles: the probability of these ensembles to be within the top 90% of the H6 distribution is as follows: (36%, 36%, 36%, 35%, 33%) and (13%, 13%, 30%, 34%, 65%) for C-CA-CB-CG, N-CA-CB-CG, CA-CB-CG-ND1, CB-CG-ND1-CE1, and O-C-CA-CB in the cyclic-linear ensembles and cyclic-fibril ensembles respectively Low side chain conformational entropy in the cyclic peptide supports a well-defined conformational pose that could aid in conferring selectivity.

VI. Ramachandran Angles

The backbone orientation that the epitope exposes to an antibody differs depending on whether the peptide is in the linear, cyclic, or fibril form. This discrepancy can be quantified by plotting the Ramachandran angles phi and psi (or ϕ and ψ), along the backbone, for residues H, D, S, G in both the linear and cyclic peptides. FIG. 7 plots the phi and psi angles sampled in equilibrium simulations, for residues H6, D7, S8, and G9 in both linear and cyclic peptides consisting of sequence CGHDSGG (SEQ ID NO: 2), as well as HDSG (SEQ ID NO: 1) in the context of the fibril structure 2M4J. From FIG. 7 it can be seen that the distribution of backbone dihedral angles in the cyclic peptide is most different from the distribution of dihedral angles sampled for either the linear peptide, or for the peptide HDSG (SEQ ID NO: 1) in the context the fibril structure 2M4J, for the BB dihedral angles of residues D7 and S8.

As a specific example, for residue D7, FIG. 7 shows a distribution of Ramachandran ϕ, ψ angles that for the cyclic peptide has peak values (most-likely values) at (ϕ, ψ)=((−65.9°, −44.5°). For the linear peptide, these most likely values are (ϕ, ψ)=(−153°, 165°), and (−66°, 143°) (there are two peaks) and for the fibril structure 2M4J, these most likely values are (ϕ, ψ)=(−60°, 143°) and (−150°, 143°). The substantial difference in the peak dihedral angle values implies that antibodies selected for the cyclic epitope conformation will likely have lower affinity for the linear and fibril epitopes.

The peak values (most likely values) of the Ramachandran backbone ϕ, ψ distributions for H6, D7, S8, and G9 are given in Table 2. The first column in Table 2 gives the residue considered, which manifests two angles, phi and psi, V. Entropy of the Side Chains The side chain entropy of a residue may be approximately calculated from $$S/k_B = -\sum_i \int d\phi_i\, p(\phi_i)\ln p(\phi_i).$$

Where the sum is over all dihedral angles in a particular residue's side chain, and $p(\phi_i)$ is the dihedral angle distribution, as analyzed above.

A plot of the increase in residue entropy in the cyclic peptide ensemble, over the entropy of the fibril, is shown in FIG. 6. The entropy of H6 is reduced compared to the linear and fibril, indicating a more constrained pose for H6. Similarly, the entropy of S8 is only marginally greater than the fibril for either the linear or cyclic peptide. The entropy of D7 is reduced relative to the monomer but increased relative to the fibril.

Dissection of Entropy of Residue Side-Chain Moieties

The entropy of each dihedral angle was investigated in the respective side chains of H, D, and S. The entropy of the dihedral angles for H6, D7, and S8 are plotted in FIG. 6. The entropy for several dihedrals of H, D and S is reduced relative to the fibril, indicating a restricted pose for those angles in a conformation that tends to be distinct from either the fibril or linear monomer.

indicated in parenthesis. The 2$^{nd}$ column indicates the peak values of the Ramachandran phi/psi angles for HDSG (SEQ ID NO: 1) in the context of the linear peptide CGHDSGG (SEQ ID NO: 2), while the 3$^{rd}$ column indicates the peak values of the Ramachandran phi/psi angles for HDSG (SEQ ID NO: 1) in the context of the cyclic peptide CGHDSGG (SEQ ID NO: 2), and the last column indicates the peak values of the Ramachandran phi/psi angles for HDSG (SEQ ID NO: 1) in the context of the fibril structure 2M4J. See FIG. 7. The backbone Ramachandran angles are very similar between all 3 species for H6. For D7, there are a minority of points in the linear and fibril ensembles that overlap with the points in the cyclic ensemble. If an ellipse that encloses 90% of the points of the cyclic ensemble is considered, only about 16% of the linear ensemble is inside this ellipse, and only about 10% of the fibril ensemble is inside this hull. For analogous measures for H6, the corresponding numbers are 27% for the linear ensemble and 32% for the fibril ensemble. For S8, the smallest convex hull enclosing 90% of the points of the cyclic ensemble contains 37% and 15% of the linear and fibril ensembles respectively. For G9, the 90% convex hull is best split into two convex hulls containing 90% of the points. The fraction of points contained in these hulls is 79% from the linear ensemble, and 11% from the fibril ensemble.

TABLE 2

Peak values of distributions of backbone phi/psi angles

| Peak values of distributions of backbone phi/psi angles | linear | cyclic | fibril |
|---|---|---|---|
| H6, (phi, psi) | (−98.5, 0) (−77.2, −43.3) (−162.8, 157.4) | (−164.6, 157.9) | (−147.5, 150) (−85, 150) |
| D7: (phi, psi) | (−153, 165) (−66, 143.4) | (−65.9, −44.5) | (−60.5, 143.5) (−149.5, 143.5) |
| S8: (phi, psi) | (−66.2, 144) (−158.3, 151.1) | (−70.5, −50) | (−156, 174) (−156, 12) (−66.5, −48) |
| G9: (phi, psi) | (85.9, 7) (86.1, −7) | (−114.3, −14.6) | (77.5, 0) (77.5, 158) (−62.3, 158) |

VII. Solubility and Antigenicity of the Predicted Epitope Sequence

The solubility of the residues of A-beta 42 according to the CamSol prediction scheme [4] is shown in the FIG. 8. Residues H6-G9 are denoted by vertical lines.

The more soluble a residue is, the more likely it is to be encountered on the surface of the oligomer. A relative solubility factor Gi for residue i is introduced, as:

$$\sigma_i = \frac{s_i - s_{ave}}{\delta s}$$

where $s_i$ is the solubility of residue i, $s_{ave}$ is the average solubility of the 42-residue A-beta peptide, and $\delta s$, as given above, is the standard deviation of the solubility of the 42 residue A-beta peptide.

A positive solubility indicates residues are more likely to be more exposed to solvent and accessible to antibodies; the mean solubility over all residues 1 through 42 in A-beta42 on this scale is −0.39. In the absence of further structural information, the increased solubility of this region implies that it is likely to be exposed to solvent rather than buried. Thus in an ensemble of candidate oligomers, this region may tend to be more exposed than average. The CamSol method [4] employs a linear combination of specific physicochemical properties of amino acids, including hydrophobicity, electrostatic charge of a residue at neutral pH, α-helix propensity, and β-strand propensity, which is smoothed over a window of seven residues to account for the effect of the neighboring residues. Solubility scores are computed as dimensionless numbers (A.U. or AU), and the solubility profiles are rescaled so that a random polypeptide yields a profile with mean 0 and standard deviation 1. Accordingly, amino acids with a solubility score smaller than −1 are regarded as poorly soluble and have a negative impact on the solubility of a protein, while scores larger than 1 denote highly soluble regions, yielding a positive contribution to the overall solubility.

FIG. 9 plots the solvent accessible surface area (SASA), the SASA weighted by the solubility factor for each residue, $\sigma_i \cdot SASA_i$, and $\sigma_i \cdot SASA_i$ minus the value in the fibril, i.e. the increase in this quantity in the monomer and cyclic peptide over the fibril, $\sigma_i \Delta SASA_i$. Here $s_i$ is the solubility of residue i taken from FIG. 8, <s> is the average solubility over all 42 residues of A-beta, <s>=−0.39, and $$\delta s = \sqrt{\frac{1}{N} \sum_{i=1}^{42} (s_i - \langle s \rangle)^2}$$

is the standard deviation of the solubility across all 42 residues of Aβ. The plot of SASA vs residue index indicates that residues towards the N-terminus tend to display more antibody-accessible surface in all conformations. When weighted by the solubility to indicate a measure of the likelihood that a given residue would expose surface to solvent in a context that has not been explicitly determined, residues H6 and S8 are comparable in the cyclic peptide ensemble. When SASA is weighted by the solubility as above, and then subtracted by the corresponding fibril values to indicate values relative to the fibril, residue S8 emerges as most exposed and soluble in the cyclic peptide. This analysis places emphasis on residues S8 and H6 in this peptide as potentially particularly important for binding.

The SASA of the cyclic and linear peptides are comparable, and both larger than the SASA in the fibril.

Weighting by the solubility results in the residue S8 having the most likelihood of differential exposure and availability for antibody binding, as compared to the conformation of HDSG (SEQ ID NO: 1) in the fibril structure.

VIII. The Ensemble of Cyclic Peptide Conformations Clusters Differently than the Ensemble of Either Linear or Fibril Conformations Definitive evidence that the sequence HDSG (SEQ ID NO: 1) displays a different conformation in the context of the cyclic peptide than in the linear peptide can be seen by using standard structural alignment metrics between conformations, and then implementing clustering analysis. Equilibrium ensembles of conformations are obtained for the linear and cyclic peptides CGHDSGG (SEQ ID NO: 2), as well as the full-length fibril in the 3-fold symmetric structure corresponding to PDB ID 2M4J. Snapshots of conformations from these ensembles for residues HDSG (SEQ ID NO: 1) are collected and then structurally aligned to the centroids of 3 largest clusters of the linear peptide ensemble, and the root mean squared deviation (RMSD) recorded. The clustering is performed here by the maxcluster algorithm. The 3 corresponding RMSD values for the linear, cyclic, and fibril ensembles are plotted as a 3-dimensional scatter plot in FIG. 10.

The cyclic peptide ensemble, shown as dark circles, is conformationally distinct from either the linear peptide shown as grey crosses or fibril ensembles shown as grey inverted triangles. The top plot of FIG. 10 shows that the cyclic peptide, but not the linear peptide, is differentiated from the conformations presented by the fibril. This implies that an antibody raised to the cyclic peptide may be conformationally selective and may not preferentially bind the fibril or the monomer, but that an antibody raised to the monomer may still bind to the fibril. Thus, without wishing to bound by theory, it may be that if the cyclic peptide is used as a mimic of the oligomer, an antibody raised to that mimic is unlikely to bind monomer or fibril.

It is evident from FIG. 10 that the 3 ensembles cluster differently from each other. In particular the cyclic peptide structural ensemble is distinct from either the linear or fibril ensembles, implying that antibodies specific to the cyclic peptide epitope will likely have low affinity to the conformations presented in the linear or fibril ensembles.

Two views of a representative snapshot, constituting the centroid of the largest cluster from the cyclic peptide ensemble of structures, are shown in FIG. 11A. As well, the side-chain orientations that are present for a representative conformation in the linear peptide ensemble, having dihedral angles near the peak of the dihedral angle distribution for the linear peptide ensemble, are shown in black in FIG. 11A, superimposed on the cyclic peptide, to make explicit their different orientations. Based on the dihedral angle differences discussed above it is likely that residue D7, and to a somewhat lesser extent residue S8, will be differentially exposed.

Figure 12:
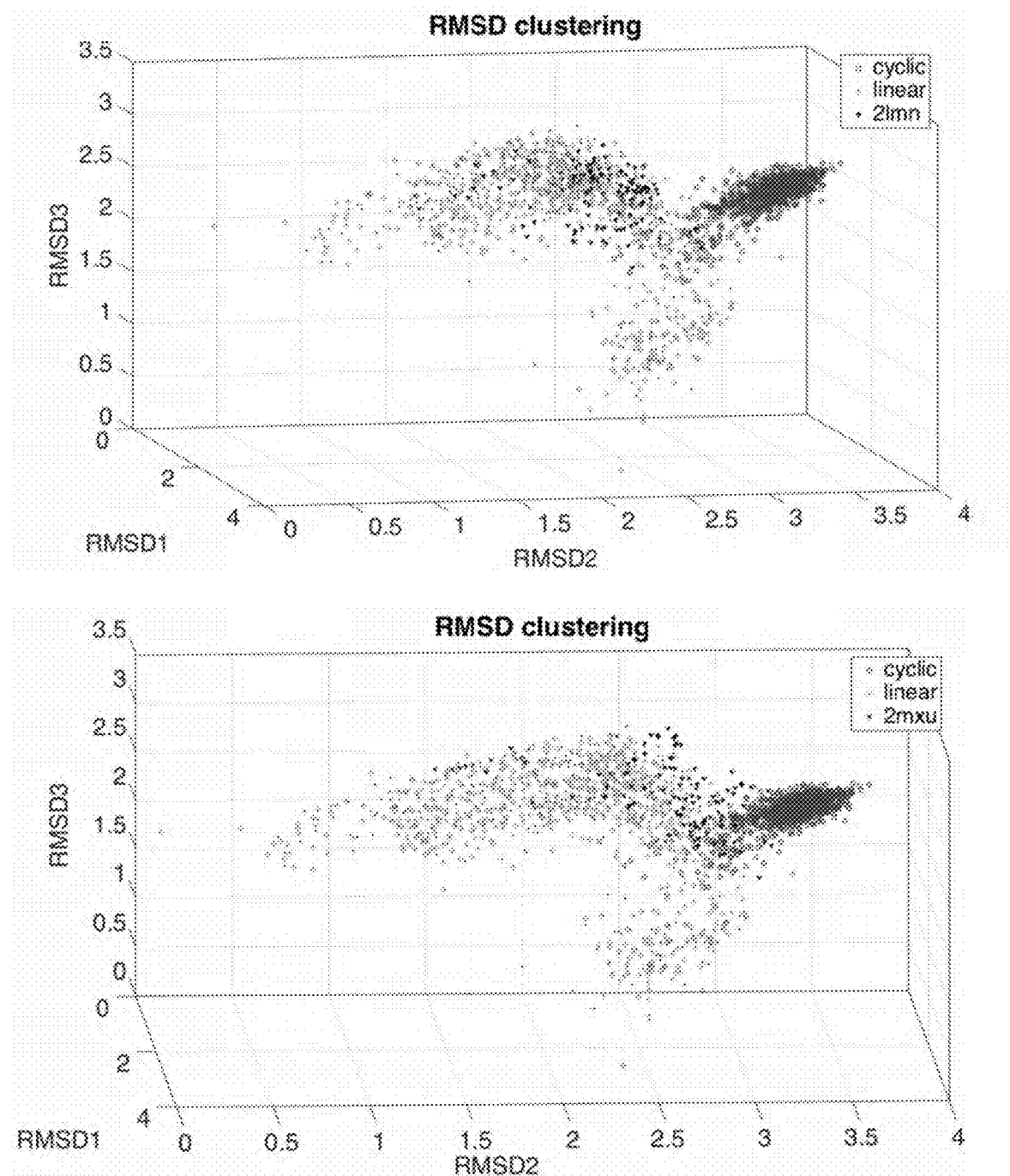
FIG. 12: Clustering plots by root mean squared deviation (RMSD); axes correspond again to the centroids of the three largest clusters of the linear peptide ensemble, as in FIG. 10.
Figure 12:
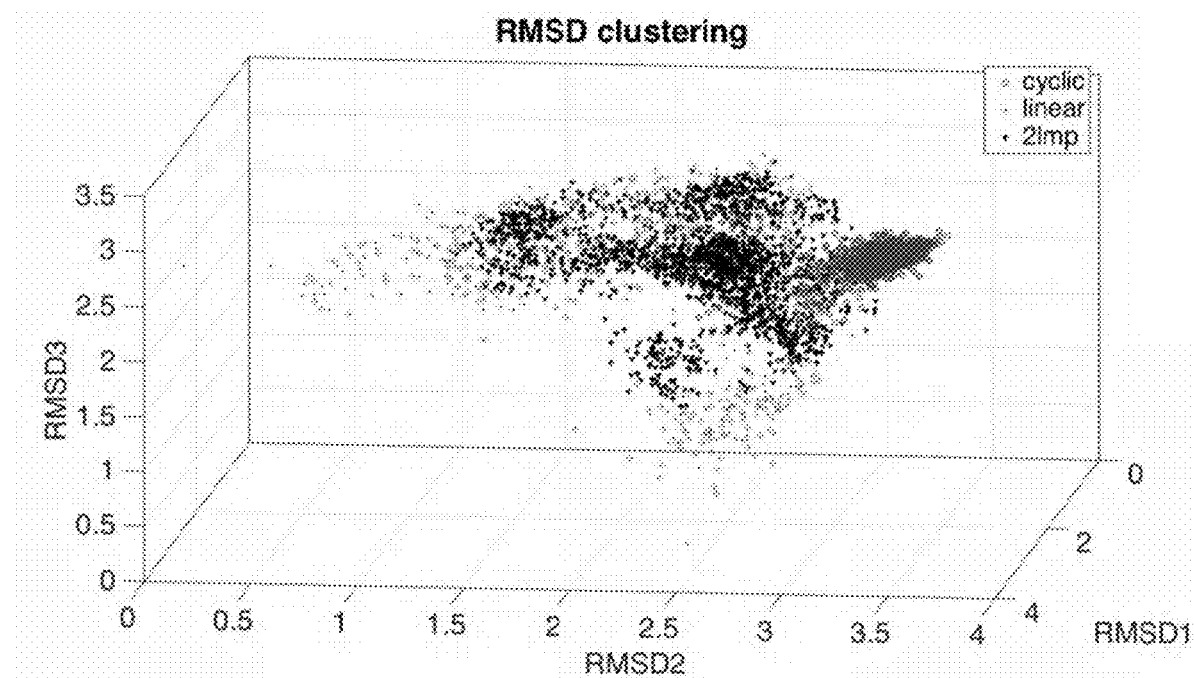

FIG. 12 is a series of clustering plots by root mean squared deviation (RMSD) and the axes correspond to the centroids of the three largest clusters of the linear peptide ensemble, as in FIG. 10.

Each point corresponds to a given conformation taken from either the cyclic peptide, or various "strains" of fibril equilibrium ensembles, from PDB IDs 2LMN, 2MXU, and 2LMP. The cyclic peptide ensemble, shown as dark circles, is conformationally distinct from all the fibril ensembles. These fibrils all have varying degrees of disordered N-termini, so that the fibril ensembles recapitulate to some extent the linear ensemble. This implies that an antibody raised to the cyclic peptide may be conformationally selective to not bind the fibril conformations for multiple strains of A-beta Table 3 lists values of the Ramachandran backbone and side chain dihedral angles undertaken for the cluster centroid cyclic peptide conformation taken from FIG. 10, and for the corresponding centroid conformations from the linear peptide and fibril ensembles. The centroid conformation for the largest cluster in the equilibrium fibril ensemble is also taken here. The differences of the corresponding dihedral angles between the cyclic and linear conformations, and between the cyclic and fibril conformations are also given. The large majority of dihedral angles in this table are significantly different, as described herein.

TABLE 3

Table of Rannachandran backbone and side chain dihedral angles shown for the cyclic peptide conformation that is the centroid of the largest conformational cluster plotted in FIG. 10, and for the centroids of the largest conformational clusters of the linear and fibril ensembles that are also plotted in FIG. 10.

|  | Cyclic | linear | 2m4j | cyclic-linear | cyclic-2m4j |
| --- | --- | --- | --- | --- | --- |
| Rama-6H | (−137.5, 154.4) | (−134.5, 155.5) | (−83.8, 124.7) | (−3.0, −1.1) | (−53.7, 29.7) |
| Rama-7D | (−75.2, −26.4) | (−147.8, 137.7) | (−79.9, 128.1) | (72.6, 164.1) | (4.7, −154.5) |
| Rama-8S | (−73.5, −50.8) | (−141.3, 144.3) | (−160.0, −179.8) | (67.8, 195.1) | (86.5, 129) |
| Rama-9G | (−123.6, 10.3) | (−84.8, −3.1) | (109.4, 174.1) | (−38.8, 13.4) | (127, −163.8) |
| 6H:O-C-CA-CB | 103.2 | 100.4 | 65.9 | 2.8 | 37.3 |
| 6H:C-CA-CB-CG | −68.9 | 48.9 | 57.2 | −117.8 | −126.1 |
| 6H: N-CA-CB-CG | 54.9 | 178.3 | −177.8 | −123.4 | −127.3 |
| 6H: CA-CB-CG-ND1 | 93.4 | 58.2 | 65.8 | 35.2 | 27.6 |
| 6H:CA-CB-CG-CD2 | −100.3 | −127.6 | −108.3 | 27.3 | 8 |
| 6H:CD2-CG-ND1-CE1 | 170.3 | −0.1 | −6.23 | 170.4 | 176.53 |
| 6H: CB-CG-ND1-CE1 | 1.62 | 175 | 178.8 | −173.38 | −177.18 |
| 6H: NE2-CE1-ND1-CG | −0.45 | 0.2 | 8.22 | −0.65 | −8.67 |
| 6H: NE2-CD2-CG-ND1 | −2.12 | 0 | 2.58 | −2.12 | −4.7 |
| 6H: NE2-CD2-CG-CB | −169.6 | −174.5 | 177.2 | 4.9 | 13.2 |
| 6H: ND1-CE1-NE2-CD2 | −0.85 | −0.25 | −7.06 | −0.6 | 6.21 |
| 6H: CG-CD2-NE2-CE1 | 1.8 | 0.16 | 2.36 | 1.64 | −0.56 |
| 7D:O-C-CA-CB | −94.9 | 87.9 | 68.9 | 177.2 | −163.8 |
| 7D: C-CA-CB-CG | 176.3 | −51.2 | −180 | −132.5 | −3.6 |

TABLE 3-continued

Table of Rannachandran backbone and side chain dihedral angles shown for the cyclic peptide conformation that is the centroid of the largest conformational cluster plotted in FIG. 10, and for the centroids of the largest conformational clusters of the linear and fibril ensembles that are also plotted in FIG. 10.

|  | Cyclic | linear | 2m4j | cyclic-linear | cyclic-2m4j |
|---|---|---|---|---|---|
| 7D: N-CA-CB-CG | −63.3 | 63.3 | −60.9 | −126.6 | −2.4 |
| 7D: CA-CB-CG-OD2 | −33.8 | 113.3 | 149.6 | −147.1 | 176.6 |
| 7D: CA-CB-CG-OD1 | 131.6 | −70.8 | −37.3 | −157.6 | 168.9 |
| 8S: N-CA-CB-OG | −46.7 | −163.2 | −164 | 116.5 | 117.3 |
| 8S: C-CA-CB-OG | −170.5 | 76.4 | 69.2 | 95.1 | 120.3 |
| 8S: O-C-CA-CB | −109.7 | 84.1 | 125.8 | 166.2 | 124.5 |

TABLE 4

Table of mean curvature values for each residue in the cyclic, linear, and 2M4J fibril ensembles. Curvature vs residue index is plotted in FIG. 2.

| Curvatures | Linear | cyclic | 2M4J |
|---|---|---|---|
| 6H | 1.19 | 0.781 | 1.01 |
| 7D | 0.99 | 1.41 | 1.03 |
| 8S | 0.95 | 1.36 | 0.93 |
| 9G | 1.40 | 1.31 | 0.86 |

Example 3

Cyclic Compound Construction Comprising a Conformationally Constrained Epitope

Peptides comprising HDSG (SEQ ID NO: 1) such as Cyclo(CGHDSGG) (SEQ ID NO: 2) can be cyclized head to tail.

A linear peptide comprising HDSG (SEQ ID NO: 1) and a linker, preferably comprising 2, 3, or 4 amino acids and/or PEG units, can be synthesized using known methods such as Fmoc based solid phase peptide synthesis alone or in combination with other methods. PEG molecules can be coupled to amine groups at the N terminus for example using coupling chemistries described in Hamley 2014 [6] and Roberts et al 2012 [7], each incorporated herein by reference. The linear peptide compound may be cyclized by covalently bonding 1) the amino terminus and the carboxy terminus of the peptide+linker to form a peptide bond (e.g. cyclizing the backbone), 2) the amino or carboxy terminus with a side chain in the peptide+linker or 3) two side chains in the peptide+linker.

The bonds in the cyclic compound may be all regular peptide bonds (homodetic cyclic peptide) or include other types of bonds such as ester, ether, amide or disulfide linkages (heterodetic cyclic peptide).

Peptides may be cyclized by oxidation of thiol- or mercaptan-containing residues at the N-terminus or C-terminus, or internal to the peptide, including for example cysteine and homocysteine. For example two cysteine residues flanking the peptide may be oxidized to form a disulphide bond. Oxidative reagents that may employed include, for example, oxygen (air), dimethyl sulphoxide, oxidized glutathione, cystine, copper (II) chloride, potassium ferricyanide, thallium(III) trifluro acetate, or other oxidative reagents such as may be known to those of skill in the art and used with such methods as are known to those of skill in the art.

Methods and compositions related to cyclic peptide synthesis are described in US Patent Publication 2009/0215172. US Patent publication 2010/0240865, US Patent Publication 2010/0137559, and U.S. Pat. No. 7,569,541 describe various methods for cyclization. Other examples are described in PCT Publication WO01/92466, and Andreu et al., 1994. Methods in Molecular Biology 35:91-169.

More specifically, a cyclic peptide comprising the HDSG (SEQ ID NO: 1) epitope can be constructed by adding a linker comprising a spacer with cysteine residues flanking and/or inserted in the spacer. The peptide can be structured into a cyclic conformation by creating a disulfide linkage between the non-native cysteines residues added to the N- and C-termini of the peptide. It can also be synthesized into a cyclic compound by forming a peptide bond between the N- and C-termini amino acids (e.g. head to tail cyclization).

Peptide synthesis is performed by CPC Scientific Inc. (Sunnyvale CA, USA) following standard manufacturing procedures.

For example Cyclo(CGHDSGC)(SEQ ID NO: 12) cyclic peptide comprising the conformational epitope HDSG (SEQ ID NO: 1) is constructed in a constrained cyclic conformation using a disulfide linkage between cysteine residues added to the N- and C-termini of a peptide comprising HDSG (SEQ ID NO: 1). Two non-native cysteine residues were added to GHDSG (SEQ ID NO: 7) one at the C-terminus and one at the N-terminus. The two cysteines are oxidized under controlled conditions to form a disulfide bridge or reacted head to tail to produce a peptide bond.

As described above, the structure of the cyclic peptide was designed to mimic the conformation and orientation of the amino acid side changes of HDSG (SEQ ID NO: 1) in A-beta oligomer.

(SEQ ID NO: 2)
Cyclo(CGHDSGG)

Cyclo(CGHDSGG) (SEQ ID NO: 2) was synthesized using the following method (CPC Scientific Inc, Sunnyvale CA). The protected linear peptide was synthesized by standard conventional Fmoc-based solid-phase peptide synthesis on 2-chlorotrityl chloride resin, followed by cleavage from the resin with 30% HFIP/DCM. Protected linear peptide was cyclized to the corresponding protected cyclic peptide by using EDC·HCl/HOBt/DIEA in DMF at low concentration. The protected cyclic peptide was deprotected by TFA to give crude cyclic peptide and the crude peptide was purified by RP HPLC to give pure cyclic peptide after lyophilize.

Cyclo(CGHDSGG) (SEQ ID NO: 2) can be prepared by amide condensation of the linear peptide CGHDSGG (SEQ ID NO: 2).

Cyclo(C-PEG2-HDSGG) can be prepared by amide condensation of the linear compound C-PEG2-HDSGG (SEQ ID NO: 28).

Linear(CGHDSGG) was prepared (CPC Scientific Inc, Sunnyvale CA) The protected linear peptide was synthesized by standard conventional Fmoc-based solid-phase peptide synthesis on Fmoc-Gly-Wang resin, then the protected peptide was cleaved by TFA to give crude peptide and the crude peptide was purified by RP HPLC to give pure peptide after lyophilize, and which was used to conjugate BSA.

Immunogen Construction

The cyclic compound Cyclo(CGHDSGG) (SEQ ID NO: 2) was synthesized as described above and then conjugated to BSA and/or KLH (CPC Scientific Inc, Sunnyvale CA). BSA or KLH was re-activated by SMCC in PBS buffer, then a solution of the pure peptide in PBS buffer was added to the conjugation mixture, the conjugation mixture was stirred at room temperature (RT) for 2 h. Then the conjugation mixture was lyophilized after dialysis to give the conjugation product.

Example 4

Antibody Generation and Selection

A conformational constrained compound optionally a cyclic compound such as a cyclic peptide comprising HDSG (SEQ ID NO: 1) such as cyclo(CGHDSGG) (SEQ ID NO: 2) peptide is linked to Keyhole Limpet Hemocyanin (KLH). The cyclopeptide is sent for mouse monoclonal antibody production (ImmunoPrecise Antibodies LTD (Victoria BC, Canada), following protocols approved by the Canadian Council on Animal Care. Mouse sera are screened using either the conformational peptide used for producing the antibodies or a related peptide e.g. cyclo(CGHDSGG) (SEQ ID NO: 2) peptide, linked to BSA.

Hybridomas were made using an immunogen comprising cyclo(CGHDSGG) (SEQ ID NO: 2) as further described in Example 6. Hybridoma supernatants were screened by ELISA and SPR for preferential binding to cyclo (CGHDSGG) (SEQ ID NO: 2) peptide vs linear (unstructured) peptide as described herein. Positive IgG-secreting clones are subjected to large-scale production and further purification using Protein G.

Example 5

Assessing Binding or Lack Thereof to Plaques/Fibrils

Immunohistochemistry can be performed on fresh frozen human brain sections, or frozen human brain sections, post fixed in 10% formalin. Endogenous peroxidase activity can be quenched using 0.5% hydrogen peroxide in methanol for 20 min. Antigen retrieval can be achieved using sodium citrate pH 6.0 and steam heating for 25 min followed by cooling at room temperature (RT) for 30 min. After stabilization in TBS for 5-7 min, sections are treated by 70% formic acid for 15 min at RT, and then washed 3×15 min in TBS. In a humidified chamber, non-specific staining is blocked by incubation with serum-free protein blocking reagent (Dako Canada Inc., Mississauga, ON, Canada) for 1 h.

For immunostaining, antibodies described herein, positive control 6E10 (1 µg/ml) and isotype controls IgG1, 2a and 2b (1 µg/ml, Abcam) are used as primary antibodies. Sections are incubated overnight at 4° C., and washed 3×5 min in TBS-T. Anti-mouse IgG Horseradish Peroxidase conjugated (1:1000, ECL) is applied to sections and incubated 45 min, then washed 3×5 min in TBS-T. DAB chromogen reagent (Vector Laboratories, Burlington ON, Canada) is applied and sections rinsed with distilled water when the desired level of target to background staining is achieved. Sections are counterstained with Mayer's haematoxylin, dehydrated and cover slips were applied. Slides are examined under a light microscope (Zeiss Axiovert 200M, Carl Zeiss Canada, Toronto ON, Canada) and representative images captured at 50, 200 and 400× magnification using a Leica DC300 digital camera and software (Leica Microsystems Canada Inc., Richmond Hill, ON).

Example 6

Methods and Materials

Immunogen

Cyclic and linear peptides were generated at CPC Scientific, Sunnyvale, CA, USA. Peptides were conjugated to KLH (for immunizing) and BSA (for screening) using a trifluoroacetate counter ion protocol. Peptides were desalted and checked by MS and HPLC and deemed 95% pure. Peptides were shipped to IPA for use in production of monoclonal antibodies in mouse.

Antibodies

A number of hybridomas and monoclonal antibodies were generated to cyclo(CGHDSGG) (SEQ ID NO: 2) linked to Keyhole Limpet Hemocyanin (KLH).

Fifty day old female BALB/c mice (Charles River Laboratories, Quebec) were immunized. A series of subcutaneous aqueous injections containing antigen but no adjuvant were given over a period of 19 days. Mice were immunized with 100 µg of peptide per mouse per injection of a 0.5 mg/mL solution in sterile saline of cyclic peptide-KLH. Mice were housed in a ventilated rack system from Lab Products. All 4 mice were euthanized on Day 19 and lymphocytes were harvested for hybridoma cell line generation.

Fusion/Hybridoma Development

Lymphocytes were isolated and fused with murine SP2/0 myeloma cells in the presence of poly-ethylene glycol (PEG 1500). Fused cells were cultured using HAT selection. This method uses a semi-solid methylcellulose-based HAT selective medium to combine the hybridoma selection and cloning into one step. Single cell-derived hybridomas grow to form monoclonal colonies on the semi-solid media. 10 days after the fusion event, resulting hybridoma clones were transferred to 96-well tissue culture plates and grown in HT containing medium until mid-log growth was reached (5 days).

Hybridoma Analysis (Screening)

Tissue culture supernatants from the hybridomas were tested by indirect ELISA on screening antigen (cyclic peptide-BSA) (Primary Screening) and probed for both IgG and IgM antibodies using a Goat anti-IgG/IgM(H&L)-HRP secondary and developed with TMB substrate. Clones>0.2 OD in this assay were taken to the next round of testing. Positive cultures were retested on screening antigen to confirm secretion and on an irrelevant antigen (Human Transferrin) to eliminate non-specific mAbs and rule out false positives. All clones of interest were isotyped by antibody trapping ELISA to determine if they are IgG or IgM isotype. All clones of interest were also tested by indirect ELISA on other cyclic peptide-BSA conjugates as well as linear peptide-BSA conjugates to evaluate cross-reactivity.

Mouse hybridoma antibodies were screened by Indirect ELISA using cyclo(CGHDSGG) (SEQ ID NO: 2) conjugated to BSA.

ELISA Antibody Screening

Briefly, the ELISA plates were coated with 0.1 ug/well cyclo(CGHDSGG)-conjugated-BSA (SEQ ID NO: 2) at 100 uL/well in carbonate coating buffer (pH 9.6) O/N at 4 C and blocked with 3% skim milk powder in PBS for 1 hour at room temperature. Primary Antibody: Hybridoma supernatant at 100 uL/well incubated for 1 hour at 37 C with shaking. Secondary Antibody 1:10,000 Goat anti-mouse IgG/IgM(H+L)-HRP at 100 uL/well in PBS-Tween for 1 hour at 37 C with shaking. All washing steps were performed for 30 mins with PBS-Tween. The substrate 3,3',5, 5'-tetramethylbenzidine (TMB) was added at 50 uL/well, developed in the dark and stopped with equal volume 1M HCl.

Positive clones were selected for further testing. Positive clones of mouse hybridomas were tested for reactivity to cyclo(CGHDSGG) (SEQ ID NO: 2) conjugated BSA and human transferrin (HT) by indirect ELISA. Plates were coated with 1) 0.1 ug/well cyclo(CGHDSGG)-conjugated-BSA (SEQ ID NO: 2) at 100 uL/well in carbonate coating buffer (pH 9.6) O/N at 4 C; or 2) 0.25 ug/well HT Antigen at 50 uL/well in dH2O O/N at 37 C. Primary Antibody: Hybridoma supernatant at 100 uL/well incubated for 1 hour at 37 C with shaking. Secondary Antibody 1:10,000 Goat anti-mouse IgG/IgM(H+L)-HRP at 100 uL/well in PBS-Tween for 1 hour at 37 C with shaking. All washing steps were performed for 30 mins with PBS-Tween. The substrate 3,3',5,5'-tetramethylbenzidine (TMB) was added at 50 uL/well, developed in the dark and stopped with equal volume 1M HCl.

ELISA Cyclo vs Linear CGHDSGG (SEQ ID NO: 2) Compound Selectivity

ELISA plates were coated with 1) 0.1 ug/well cyclo (CGHDSGG)-conjugated-BSA (SEQ ID NO:2) at 100 uL/well in carbonate coating buffer (pH 9.6) O/N at 4 C; 2)) 0.1 ug/well linear CGHDSGG-conjugated-BSA (SEQ ID NO:2) at 100 uL/well in carbonate coating buffer (pH 9.6) O/N at 4 C; or 3) 0.1 ug/well Negative-Peptide at 100 uL/well in carbonate coating buffer (pH 9.6) O/N at 4 C. Primary Antibody: Hybridoma supernatant at 100 uL/well incubated for 1 hour at 37 C with shaking. Secondary Antibody 1:10,000 Goat anti-mouse IgG/IgM(H+L)-HRP at 100 uL/well in PBS-Tween for 1 hour at 37 C with shaking. All washing steps were performed for 30 mins with PBS-Tween. The substrate TMB was added at 50 uL/well, developed in the dark and stopped with equal volume 1M HCl.

Isotyping

The hybridoma antibodies were isotyped using antibody trap experiments. Trap plates were coated with 1:10,000 Goat anti-mouse IgG/IgM(H&L) antibody at 100 uL/well carbonate coating buffer pH9.6 overnight at 4 C. No blocking step was used. Primary antibody (hybridoma supernatants) was added (100 ug/mL). Secondary Antibody 1:5,000 Goat anti-mouse IgGγ-HRP or 1:10,000 Goat anti-mouse IgMμ-HRP at 100 uL/well in PBS-Tween for 1 hour at 37 C with shaking. All washing steps were performed for 30 mins with PBS-Tween. The substrate TMB was added at 50 uL/well, developed in the dark and stopped with equal volume 1M HCl.

SPR Binding Assays—Primary and Secondary Screens
SPR Analysis of Antibody Binding to Abeta Monomers and Oligomers A-beta Monomer and Oligomer Preparation Recombinant A-beta40 and 42 peptides (California Peptide, Salt Lake City UT, USA) were dissolved in ice-cold hexafluoroisopropanol (HFIP). The HFIP was removed by evaporation overnight and dried in a SpeedVac centrifuge. To prepare monomers, the peptide film was reconstituted in DMSO to 5 mM, diluted further to 100 µM in dH2O and used immediately. Oligomers were prepared by diluting the 5 mM DMSO peptide solution in phenol red-free F12 medium (Life Technologies Inc., Burlington ON, Canada) to a final concentration of 100 µM and incubated for 24 hours to 7 days at 4° C.

SPR Analysis All SPR measurements were performed using a Molecular Affinity Screening System (MASS-1) (Sierra Sensors GmbH, Hamburg, Germany), an analytical biosensor that employs high intensity laser light and high speed optical scanning to monitor binding interactions in real time. The primary screening of tissue culture supernatants was performed using an SPR direct binding assay, whereby BSA-conjugated peptides, A-Beta42 Monomer and A-beta42 Oligomer are covalently immobilized on individual flow cells of a High Amine Capacity (HAC) sensorchip (Sierra Sensors GmbH, Hamburg, Germany) and antibodies flowed over the surface. Protein G purified mAbs were analyzed in a secondary screen using an SPR indirect (capture) binding assay, whereby the antibodies were captured on a protein A-derivatized sensorchip (XanTec Bioanalytics GmbH, Duesseldorf, Germany) and A-Beta40 Monomer, A-beta42 Oligomer, soluble brain extracts and cerebrospinal fluid flowed over the surface. The specificity of the antibodies was verified in an SPR direct binding assay by covalently immobilizing A-Beta42 Monomer and A-beta42 Oligomer on individual flow cells of a HAC sensorchip and flowing purified mAbs.

SPR Analysis of Soluble Brain Extracts and CSF Samples

Soluble brain extract and CSF Preparation Human brain tissues and CSFs were obtained from patients assessed at the UBC Alzheimer's and Related Disorders Clinic. Clinical diagnosis of probable AD is based on NINCDS-ADRDA criteria [5]. CSFs are collected in polypropylene tubes, processed, aliquoted into 100 µL polypropylene vials, and stored at −80° C. within 1 hour after lumbar puncture.

Homogenization: Human brain tissue samples were weighed and subsequently submersed in a volume of fresh, ice cold TBS (supplemented with EDTA-free protease inhibitor cocktail from Roche Diagnostics, Laval QC, Canada) such that the final concentration of brain tissue is 20% (w/v). Tissue is homogenized in this buffer using a mechanical probe homogenizer (3×30 sec pulses with 30 sec pauses in between, all performed on ice). TBS homogenized samples are then subjected to ultracentrifugation (70,000×g for 90 min). Supernatants are collected, aliquoted and stored at −80° C. The protein concentration of TBS homogenates is determined using a BCA protein assay (Pierce Biotechnology Inc, Rockford IL, USA).

SPR Analysis Brain extracts from 4 AD patients and 4 age-matched controls, and CSF samples from 9 AD patients and 9 age-matched controls were pooled and analyzed. Purified mAbs were captured on separate flow cells of a protein A-derivatized sensor chip and diluted samples injected over the surfaces for 180 seconds, followed by 120 seconds of dissociation in buffer and surface regeneration. Binding responses were double-referenced by subtraction of mouse control IgG reference surface binding and assay buffer, and the different groups of samples compared Assessing Binding or Lack Thereof to A-Beta Monomers In the primary screen of tissue culture supernatants, A-beta42 monomers and A-beta42 oligomers were used in a direct binding assay. In the secondary screen, A-beta40 monomers and A-beta42 oligomers, soluble brain extracts and CSF samples were used in an indirect (capture) binding assay.

Primary Screen

Tissue culture supernatants were screened for the presence of antibody binding against their cognate cyclic peptide. Each sample was diluted and injected in duplicate over the immobilized peptide and BSA reference surfaces for 120 seconds, followed by injection of running buffer only for a 300-second dissociation phase. After every analytical cycle, the sensor chip surfaces were regenerated. Sensorgrams were double-referenced by subtracting out binding from the BSA reference surfaces and blank running buffer injections, and binding response report points collected in the dissociation phase.

Oligomer Binding Assay

Next synthetic A-beta 42 oligomers were generated and immobilized as above, antibody binding responses analyzed. Antibody binding responses to A-beta 42 oligomers were compared to binding responses to cyclic.

Verifying Binding to A-Beta Oligomers.

To further verify and validate A-beta42 Oligomer binding, antibodies were covalently immobilized, followed by the injection over the surface of commercially-prepared stable A-beta42 Oligomers (SynAging SAS, Vandœuvre-lès-Nancy France).

Results

ELISA testing found that the majority of hybridoma clones bound the cyclopeptide.

Next clones were tested by ELISA for their binding selectivity for cyclo- and linear-CGHDSGG (SEQ ID NO: 2) compounds. A number of clones preferentially bound cyclo(CGHDSGG)-conjugated-BSA (SEQ ID NO: 2) compared to linear CGHDSGG-conjugated-BSA (SEQ ID NO: 2).

Isotyping revealed that the majority of clones were IgG including IgG1, IgG2a and IgG3 clones. Several IgM and IgA clones were also identified, but not pursued further.

A direct binding analysis using surface plasmon resonance was performed to screen for antibodies in tissue culture supernatants that bind to the cyclic peptide of SEQ ID NO: 2.

Figure 14:
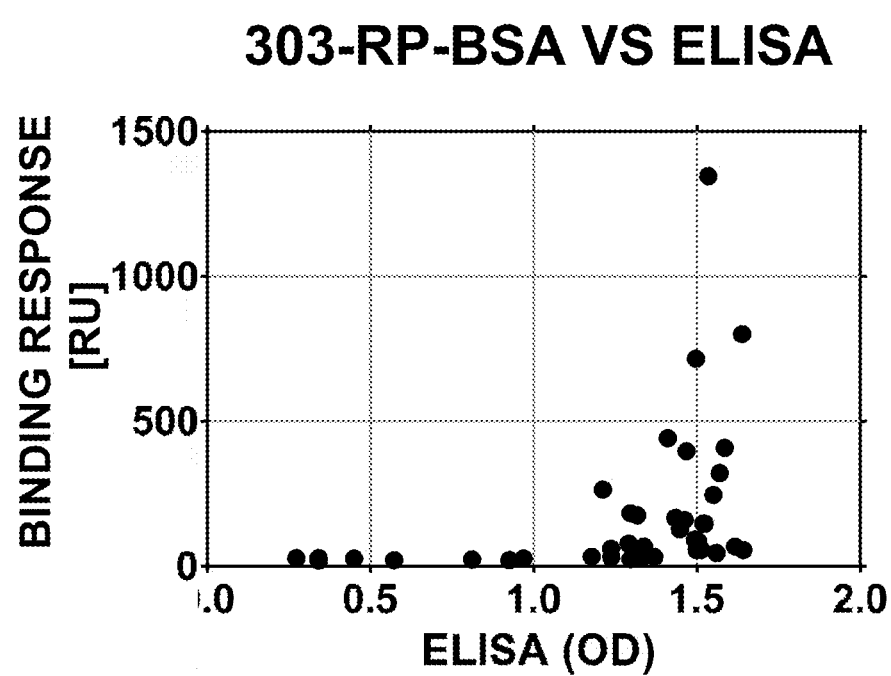
FIG. 14: Primary screening of clones from tissue culture supernatants using ELISA and SPR direct binding assay. Plot comparing mAb binding in SPR direct binding assay versus ELISA.

FIG. 14 plots the results of the direct binding assay and the ELISA results and shows that there is a correlation between the direct binding and ELISA results.

Clones were retested for their ability to bind cyclic peptide, linear peptide, A-beta 1-42 monomer and A-beta 1-42 oligomers prepared as described above. Binding assays were performed using SPR as described above (Direct binding assays). A number of clones were selected based on the binding assays performed as shown in Table 5.

The selected clones were IgG mAb. Negative numbers in the primary screen are indicative of no binding (e.g. less than isotype control).

TABLE 5

| | 303 | | | |
|---|---|---|---|---|
| | Cyclic-Peptide (RU) | Linear-Peptide (RU) | A β 42 Monomer (RU) | A β 42 Oligomer (RU) |
| 1B4 | 136.2 | −0.1 | 56.5 | 109 |
| 2B10 | 171.9 | −6.5 | −4.1 | 69.8 |
| 3C2 | 74.9 | −2.9 | 1.9 | 116.2 |
| 3C5 | 790.4 | 795.2 | 7.8 | 59 |
| 5E10 | 1334.9 | 35.7 | 8.2 | 60.2 |

TABLE 5-continued

| | 303 | | | |
|---|---|---|---|---|
| | Cyclic-Peptide (RU) | Linear-Peptide (RU) | A β 42 Monomer (RU) | A β 42 Oligomer (RU) |
| 6F1 | 23.4 | −8.7 | −11.6 | 77.9 |
| 8B2 | 310.1 | 7.6 | −2.9 | 49.4 |
| 8E7 | 386.1 | −4.2 | −25.1 | 54.2 |
| 9E5 | 253.5 | −3.9 | −20.1 | 50.8 |
| 10B9 | 17 | −1.5 | −23.2 | 61.9 |
| 10B10 | 235.2 | −4.6 | −40.8 | 45.8 |
| 10G2 | 397.6 | −0.7 | 61 | 109.8 |
| 11F10 | 148.8 | −1.5 | 8.9 | 66.9 |

ELISA Prescreen

The ELISA prescreen of hybridoma supernatants identified clones which showed increased binding to the cyclic peptides compared to the linear peptide. A proportion of the clones were reactive to KLH-epitope linker peptide. These were excluded from further investigation. The majority of the clones were determined to be of the IgG isotype using the isotyping procedure described herein.

Direct Binding Measured by Surface Plasmon Resonance—Primary Screen

Using surface plasmon resonance the tissue culture supernatants containing antibody clones were tested for direct binding to cyclic peptide, linear peptide, A-beta oligomer and A-beta monomer.

Figure 13:
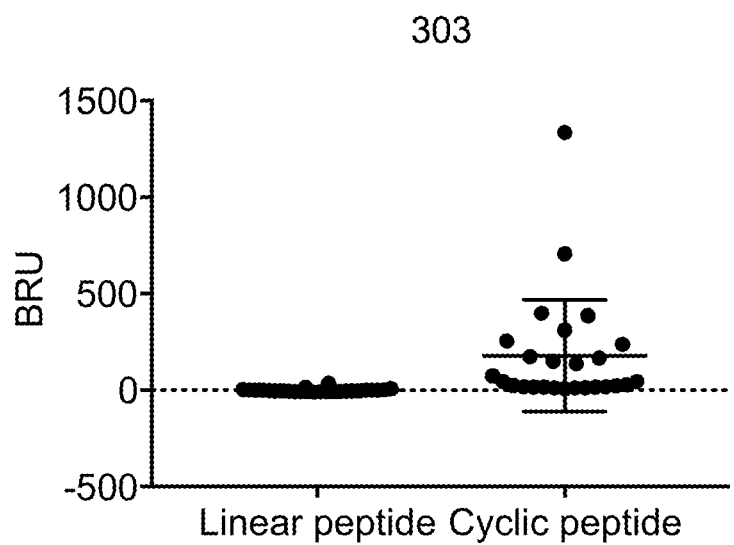
FIG. 13: Surface plasmon resonance (SPR) direct binding assay of antibodies to cyclic peptide and linear peptide in Panel A, and A-beta oligomer and A-beta monomer in Panel B.
Figure 13:
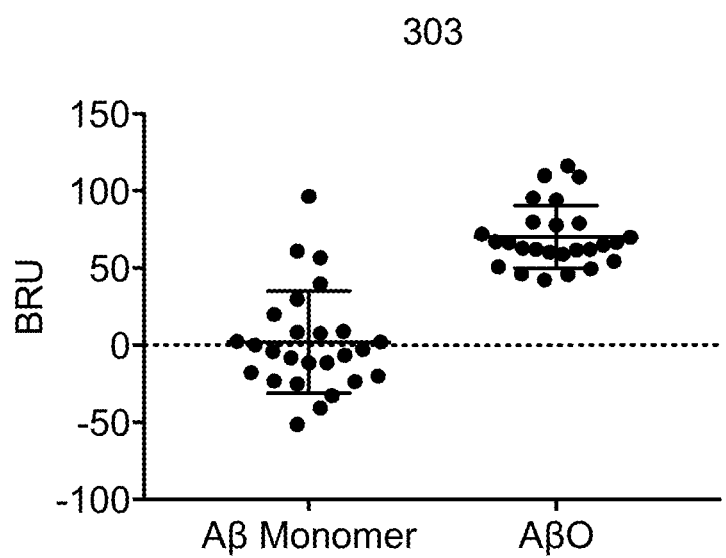

The results for the primary screen are shown in FIG. 13. Panel A shows binding to cyclic peptide and to linear peptide. Panel B shows binding to A-beta oligomer and A-beta monomer. A number of the clones have elevated reactivity to the cyclic peptide and all clones have minimal or no reactivity to linear peptide. There is a general selectivity for A-beta oligomer binding. Monomer reactivity is around or below 0 for most epitopes and most clones.

Figure 15:
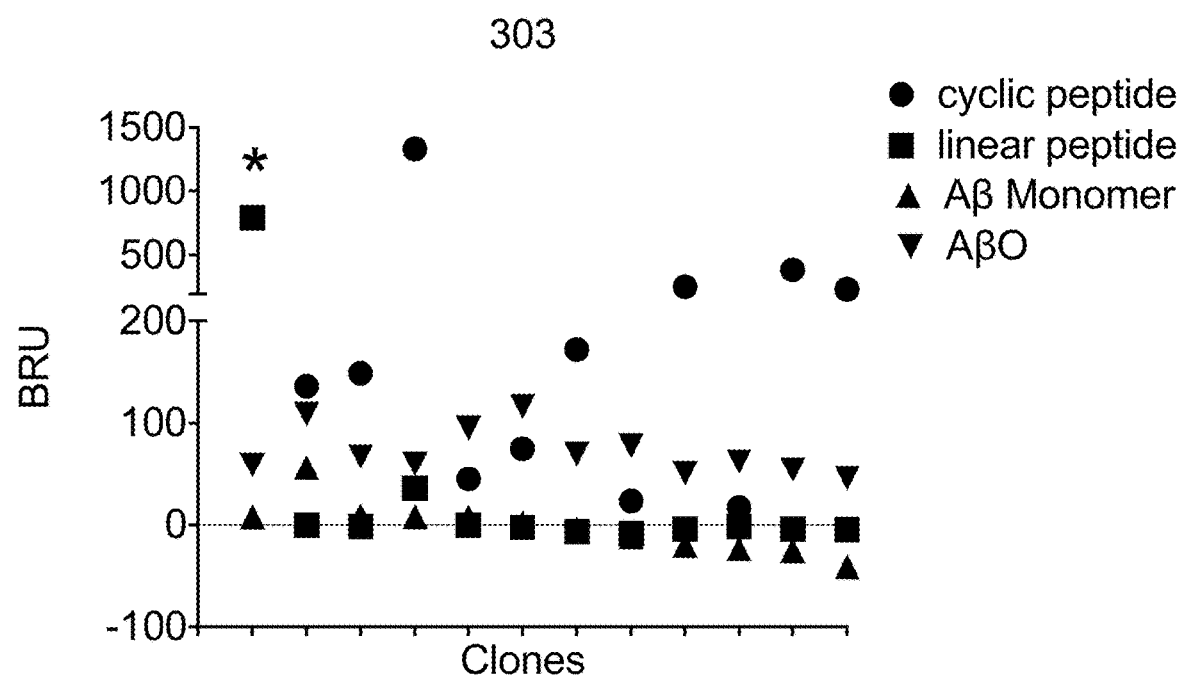
FIG. 15: SPR direct binding assay of select clones to cyclic peptide (structured peptide: circles), linear peptide (unstructured peptide, squares), A-beta monomer (upward pointing triangles), and A-beta oligomer (downward pointing triangles). Asterisk indicates a clone reactive to unstructured linear peptide for control purposes.

For select clones comparative binding profile is shown in FIG. 15. Each clone is assessed for direct binding using surface plasmon resonance against specific epitope in the context of cyclic peptide (structured), linear peptide (unstructured), A-beta monomer, and A-beta oligomer. A clone reactive preferentially to unstructured epitope (e.g. linear epitope) was chosen as control, as indicated by an asterisk.

Example 7

Secondary Screen
Immunohistochemistry

Immunohistochemistry was performed on frozen human brain sections, with no fixation or antigen retrieval. In a humidified chamber, non-specific staining was blocked by incubation with serum-free protein blocking reagent (Dako Canada Inc., Mississauga, ON, Canada) for 1 h. The following primary antibodies were used for immunostaining: mouse monoclonal isotype controls IgG1, IgG2a, and IgG2b, and anti-amyloidβ6E10, all purchased from Biolegend, and selected purified clones reactive to the cyclopeptide. All antibodies were used at 1 µg/mL. Sections were incubated at room temperature for 1 h, and washed 3×5 min in TBS-T. Anti-Mouse IgG Horseradish Peroxidase conjugated (1:1000, ECL) was applied to sections and incubated 45 min, then washed 3×5 min in TBS-T. DAB chromogen reagent (Vector Laboratories, Burlington ON, Canada) was applied and sections rinsed with distilled water when the desired level of target to background staining was achieved. Sections were counterstained with Mayer's haematoxylin, dehydrated and cover slips were applied. Slides were examined under a light microscope (Zeiss Axiovert 200M, Carl Zeiss Canada, Toronto ON, Canada) and representative images captured at 20 and 40× magnification using a Leica DC300 digital camera and software (Leica Microsystems Canada Inc., Richmond Hill, ON). Images were optimized in Adobe Photoshop using Levels Auto Correction.

CSF and Brain Extracts

Human brain tissues were obtained from the University of Maryland Brain and Tissue Bank upon approval from the UBC Clinical Research Ethics Board (C04-0595). CSFs were obtained from patients assessed at the UBC Hospital Clinic for Alzheimer's and Related Disorders. The study was approved by the UBC Clinical Research Ethics Board, and written consent from the participant or legal next of kin was obtained prior to collection of CSF samples. Clinical diagnosis of probable AD was based on NINCDS-ADRDA criteria. CSFs were collected in polypropylene tubes, processed, aliquoted into 100 µL polypropylene vials, and stored at −80° C. within 1 hour after lumbar puncture.

Homogenization: Human brain tissue samples were weighed and subsequently submersed in a volume of fresh, ice cold TBS and EDTA-free protease inhibitor cocktail from Roche Diagnostics (Laval QC, Canada) such that the final concentration of brain tissue was 20% (w/v). Tissue was homogenized in this buffer using a mechanical probe homogenizer (3×30 sec pulses with 30 sec pauses in between, all performed on ice). TBS homogenized samples were then subjected to ultracentrifugation (70,000×g for 90 min). Supernatants were collected, aliquoted and stored at −80° C. The protein concentration of TBS homogenates was determined using a BCA protein assay (Pierce Biotechnology Inc, Rockford IL, USA).

CSF: CSF was pooled from 9 donors with AD and 9 donors without AD. Samples were analyzed by SPR using purified IgG at a concentration of 30 micrograms/ml for all antibodies Mouse IgG was used as an antibody control, and all experiments were repeated at least 2 times.

Positive binding in CSF and brain extracts was confirmed using antibody 6E10.

SPR Analysis: 4 brain extracts from AD patients and 4 brain extracts from age-matched controls were pooled and analyzed. Brain samples, homogenized in TBS, included frontal cortex Brodmann area 9. All experiments were performed using a Molecular Affinity Screening System (MASS-1) (Sierra Sensors GmbH, Hamburg, Germany), an analytical biosensor that employs high intensity laser light and high speed optical scanning to monitor binding interactions in real time as described in Example 6. Purified antibodies generated for cyclopeptides described herein were captured on separate flow cells of a protein A-derivatized sensor chip and diluted samples injected over the surfaces for 180 seconds, followed by 120 seconds of dissociation in buffer and surface regeneration. Binding responses were double-referenced by subtraction of mouse control IgG reference surface binding and assay buffer, and the different groups of samples compared.

Results

CSF Brain Extracts and Immunohistochemistry

Several clones were tested for their ability to bind A-beta in CSF, soluble brain extracts and tissue samples of cadaveric AD brains are shown in Table 6. Strength of positivity in Table 6 is shown by the number plus signs.

Table 6 and Table 7 provide data for selected clone's binding selectivity for oligomers over monomer measured as described herein by SPR.

IHC results are also summarized in Table 6 where "+/−" denotes staining similar to or distinct from isotype control but without clear plaque morphology.

Figure 16:
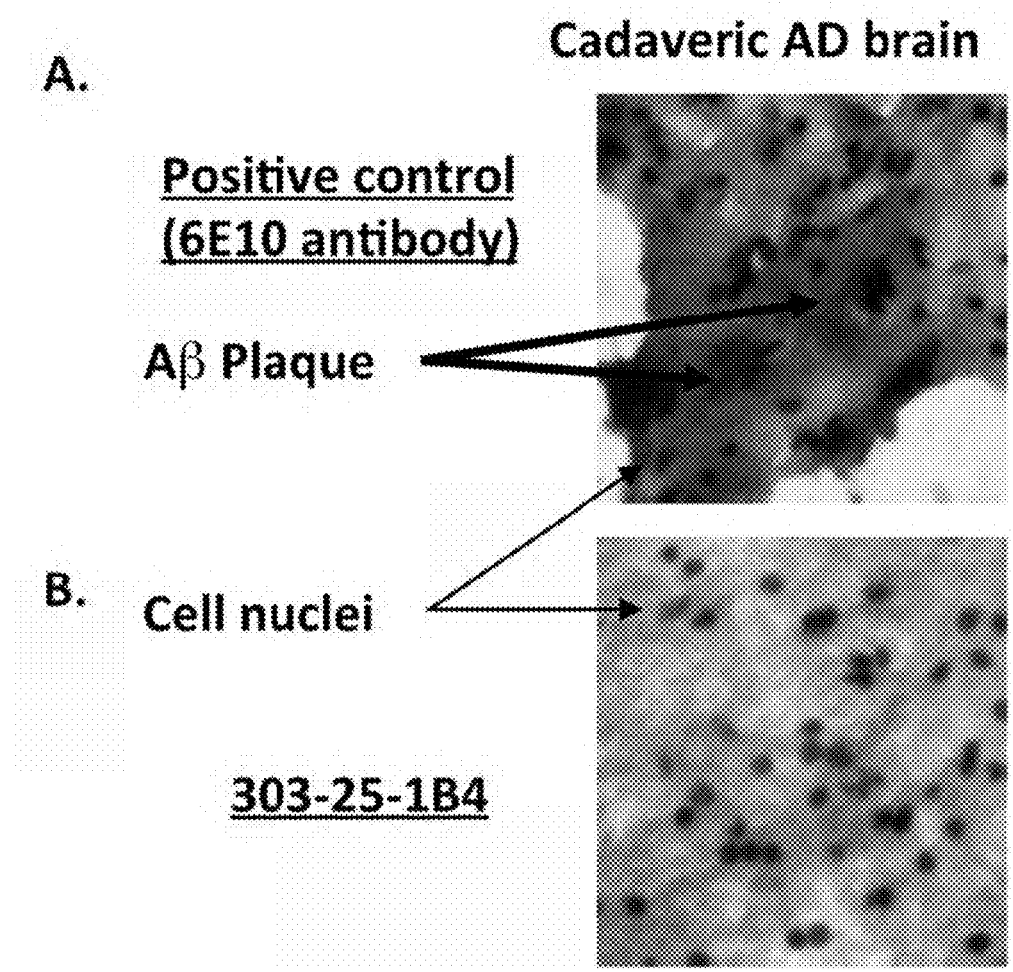
FIG. 16: Immunohistochemical staining of plaque from cadaveric AD brain using 6E10 positive control antibody (A) and an antibody (303-25-1B4) raised against cyclo (CGHDSGG) (SEQ ID NO:2) (B).

FIG. 16 shows an example of the lack of plaque staining on fresh frozen sections with clone 25-1B4 compared to the positive plaque staining seen with 6E10 antibody.

Figure 17:
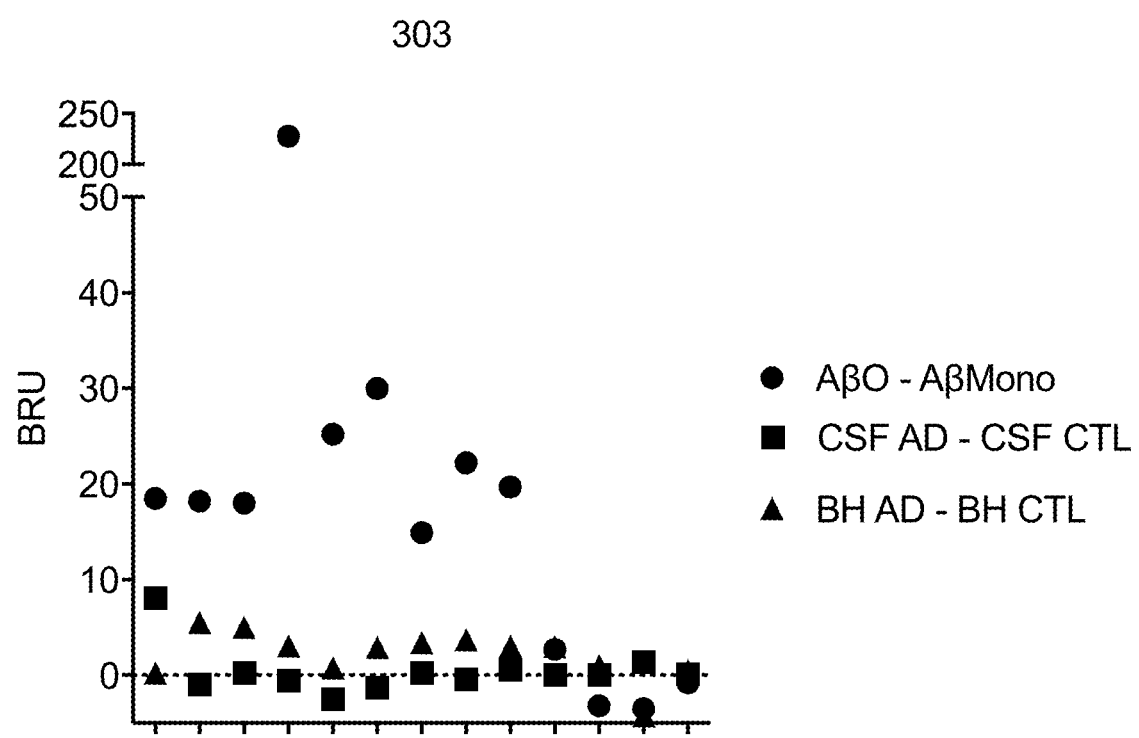
FIG. 17: Secondary Screening of selected and purified antibodies using an SPR indirect (capture) binding assay. SPR binding response of A-beta oligomer to captured antibody minus binding response of A-beta monomer to captured antibody (circle); SPR binding response of pooled soluble brain extract from AD patients to captured antibody minus binding response of pooled brain extract from non-AD controls to captured antibody (triangle); SPR binding response of pooled cerebrospinal fluid (CSF) from AD patients to captured antibody minus binding response of pooled CSF from non-AD controls to captured antibody (square).

FIG. 17 shows, antibodies raised to the cyclopeptide comprising HDSG (SEQ ID NO: 1) bound A-beta oligomer preferentially over monomer and also preferentially bound A-beta in brain extracts and/or CSF of AD patients.

As shown in Tables 6, 7 and FIGS. 16 and 17, antibodies raised to the cyclopeptide comprising HDSG (SEQ ID NO: 1) bound to A-beta in brain extracts and/or CSF, but did not appreciably bind to monomers on SPR, and did not appreciably bind to plaque fibrils by IHC

TABLE 6

Summary of binding characteristics

| Clone # | Oligomers/ Monomers | CSF AD/ Non-AD | Brain Extract AD/ Non-AD | IHC-Plaque Staining |
|---|---|---|---|---|
| cyclo(CGHDSGG) (SEQ ID NO: 2) 25 (1B4) | +++ | +++ | + | − |
| 28 (3C5) | + | − | ++ | + |
| 26 | ++ | − | ++ | − |
| 30 | + | − | ++ | N/A |

*Scoring is relative to other clones in the same sample category.

TABLE 7

A-beta Oligomer binding RU values subtracted for monomer binding

| Clone tested | 303-3C5 |
|---|---|
| RU | 227.7 |

Example 8

Synthetic Oligomer Binding

Figure 18:
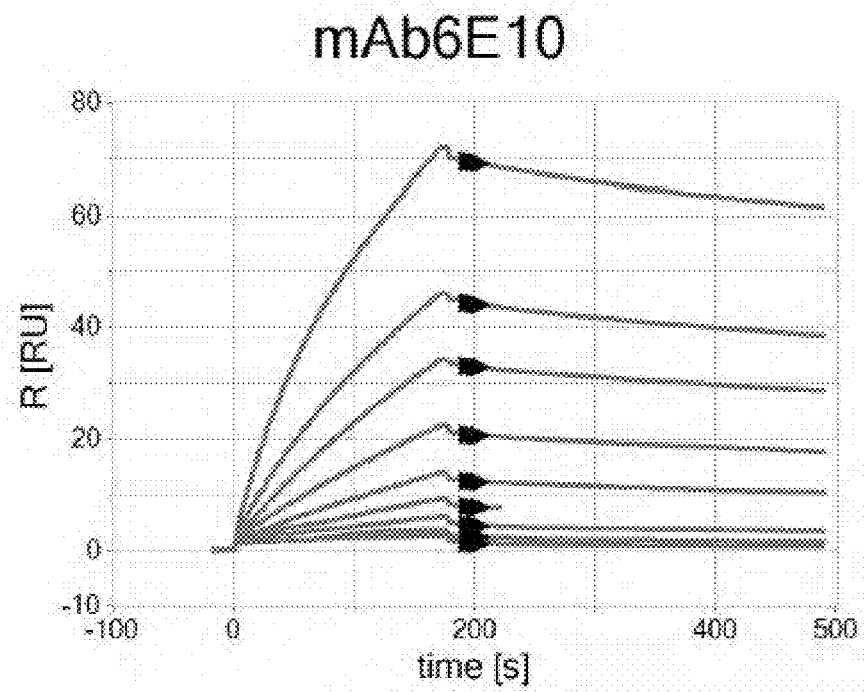
FIG. 18: Verification of Antibody binding to A-beta oligomers. SPR sensorgrams and binding response plots of varying concentrations of commercially-prepared stable A-beta oligomers binding to immobilized antibodies. Panel A shows results with the positive control mAb6E10, Panel B with the negative isotype control and Panel C with antibody raised against cyclo (CGHDSGG) (SEQ ID NO:2). Panel D plots binding of several antibody clones raised against cyclic peptide comprising HDSG (SEQ ID No: 1), with A-beta oligomer at a concentration of 1 micromolar.
Figure 18:
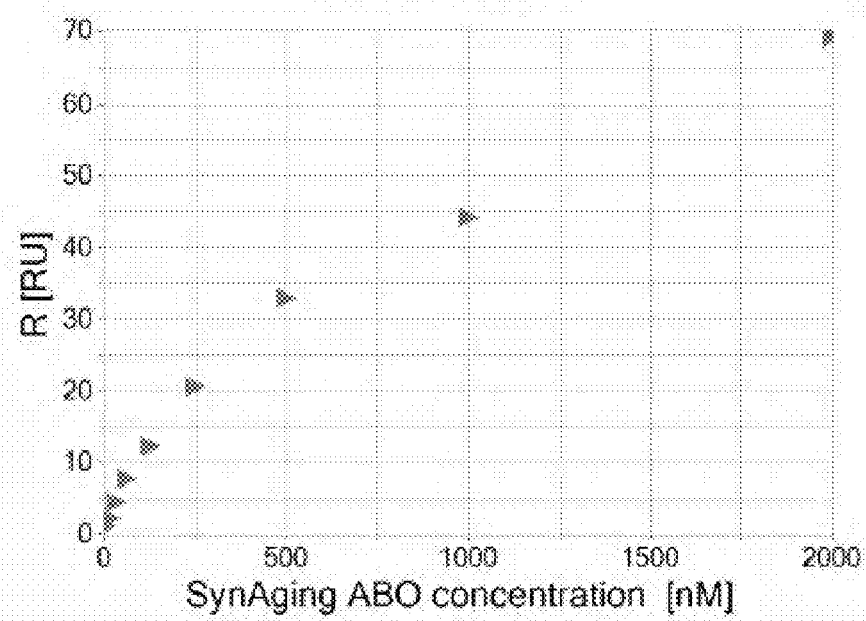
Figure 18:
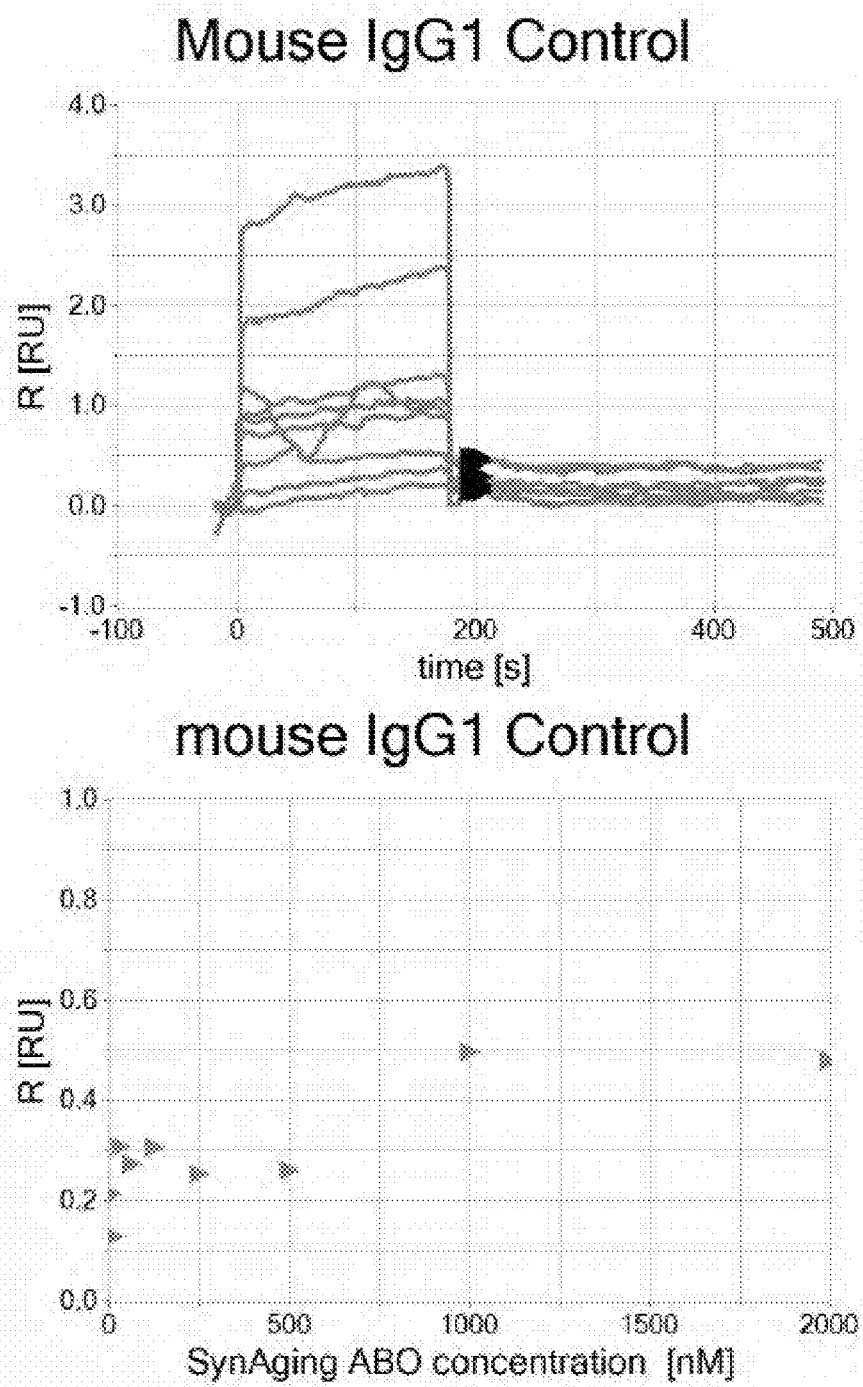
Figure 18:
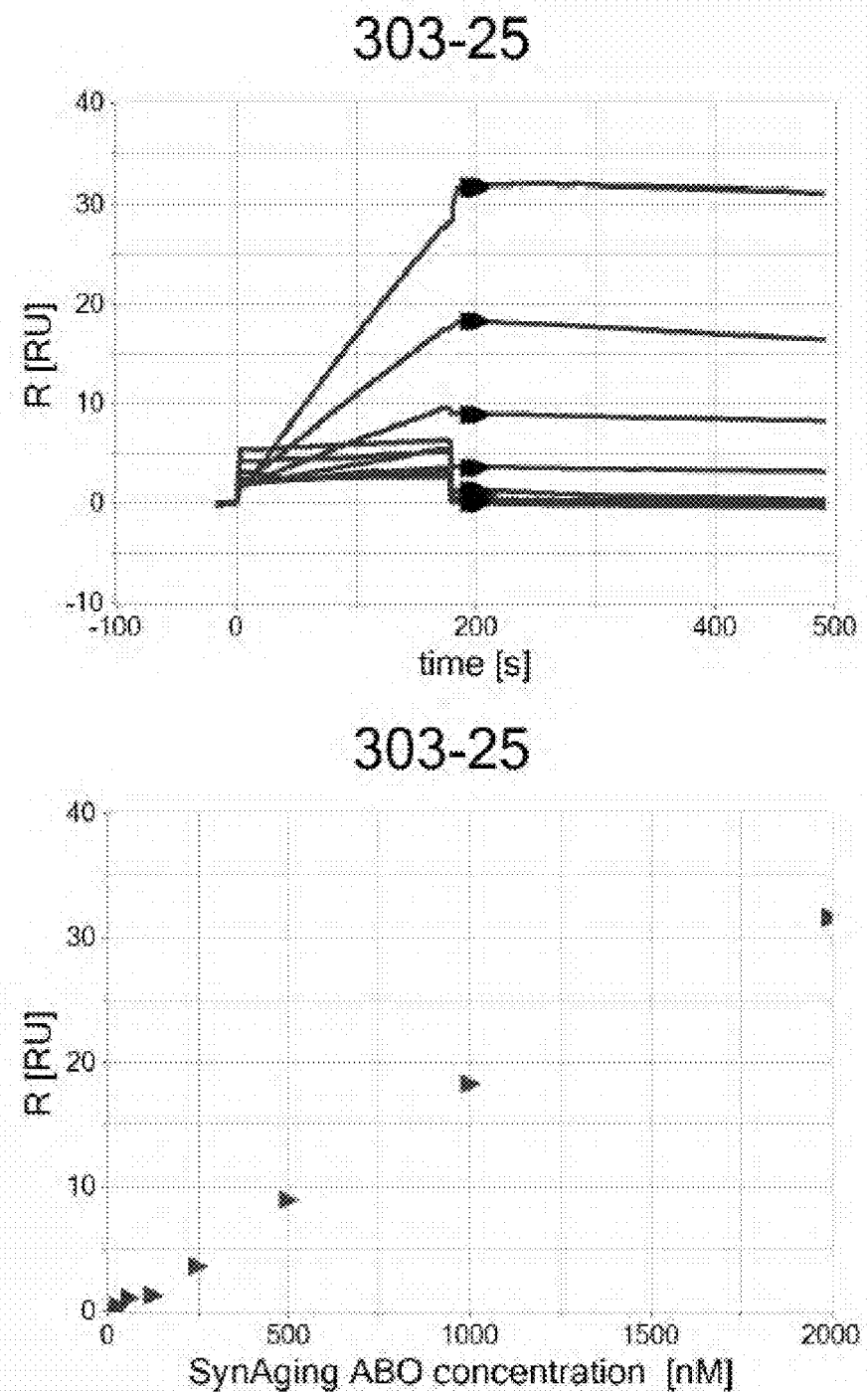
Figure 18:
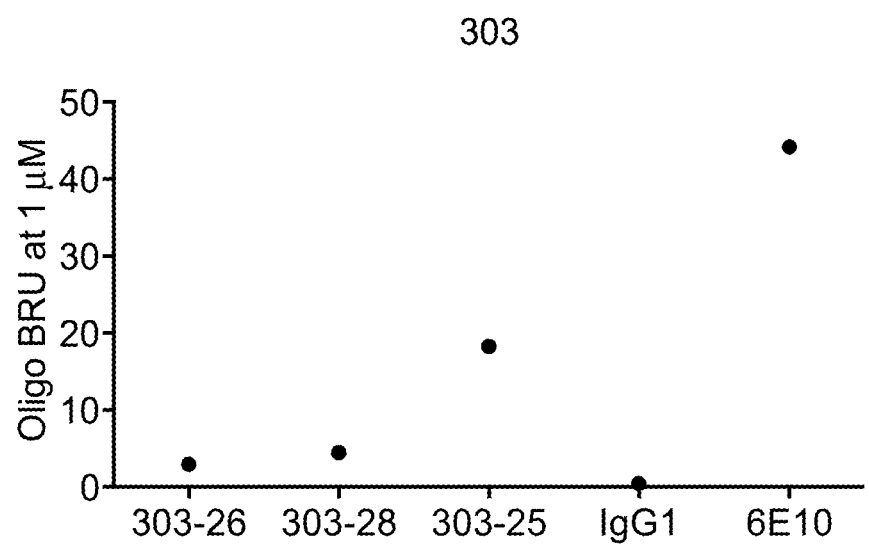

Serial 2-fold dilutions (7.8 nM to 2000 nM) of commercially-prepared synthetic amyloid beta oligomers (SynAging SAS, Vandœuvre-lès-Nancy, were tested for binding to covalently immobilized antibodies. Results for control antibody mAb6E10 is shown in FIG. 18A and for mouse control IgG is shown in FIG. 18B. FIG. 18 C shows results using an antibody raised against cyclo(CGHDSGG) (SEQ ID NO:2).

Example 9

Immunohistochemistry on Formalin Fixed Tissues

Human brain tissue was assessed using antibodies raised to cyclo(CGHDSGG) (SEQ ID NO: 2). The patient had been previously characterized and diagnosed with Alzheimer's disease with a tripartite approach: (i) Bielschowsky silver method to demonstrate senile plaques and neurofibrillary tangles, (ii) Congo red to demonstrate amyloid and (iii) tau immunohistochemistry to demonstrate tangles and to confirm the senile plaques are "neuritic". This tissue was used to test plaque reactivity of selected monoclonal antibody clones. The brain tissues were fixed in 10% buffered formalin for several days and paraffin processed in the Sakura VIP tissue processors. Tissue sections were probed with 1 µg/ml of antibody with and without microwave antigen retrieval (AR). The pan-amyloid beta reactive antibody 6E10 was included along with selected antibody clones as a positive control. Antibodies were diluted in Antibody Diluent (Ventana), color was developed with OptiView DAB (Ventana). The staining was performed on the Ventana Benchmark XT IHC stainer. Images were obtained with an Olympus BX45 microscope. Images were analyzed blind by a professional pathologist with expertise in neuropathology.

As shown in Table 8 below, using fixed tissue, the tested antibodies were negative for specific staining of senile plaque amyloid with or without antigen retrieval. 6E10 was used as the positive control.

TABLE 8

| Epitope | Antibodies to test | Convincing evidence of specific staining of senile plaque amyloid | |
| --- | --- | --- | --- |
| | | Without AR | Plus AR |
| 303 | 25 | Neg | Neg |
| | 28 | Neg | Neg |
| Positive Control | 6E10 | strongly positive | strongly positive |

Example 10

Inhibition of Oligomer Propagation

The biological functionality of antibodies was tested in vitro by examining their effects on propagation of Amyloid Beta (Aβ) aggregation using the Thioflavin T (ThT) binding assay. Aβ aggregation is induced by and propagated through nuclei of preformed small Aβ oligomers, and the complete process from monomeric Aβ to soluble oligomers to insoluble fibrils is accompanied by concomitantly increasing beta sheet formation. This can be monitored by ThT, a benzothiazole salt, whose excitation and emission maxima shifts from 385 to 450 nm and from 445 to 482 nm respectively when bound to beta sheet-rich structures and resulting in increased fluorescence. Briefly, Aβ 1-42 (Bachem Americas Inc., Torrance, CA) was solubilized, sonicated, diluted in Tris-EDTA buffer (pH7.4) and added to wells of a black 96-well microtitre plate (Greiner Bio-One, Monroe, NC) to which equal volumes of cyclopeptide raised antibody or irrelevant mouse IgG antibody isotype controls were added, resulting in a 1:5 molar ratio of Aβ1-42 peptide to antibody. ThT was added and plates incubated at room temperature for 24 hours, with ThT fluorescence measurements (excitation at 440 nm, emission at 486 nm) recorded every hour using a Wallac Victor3v 1420 Multilabel Counter (PerkinElmer, Waltham, MA). Fluorescent readings from background buffer were subtracted from all wells, and readings from antibody only wells were further subtracted from the corresponding wells.

As shown in FIG. 19, Aβ42 aggregation, as monitored by ThT fluorescence, demonstrated a sigmoidal shape characterized by an initial lag phase with minimal fluorescence, an exponential phase with a rapid increase in fluorescence and finally a plateau phase during which the AB molecular species are at equilibrium and during which there is no increase in fluorescence. Co-incubation of Aβ42 with an irrelevant mouse antibody did not have any significant effect on the aggregation process. In contrast, co-incubation of Aβ42 with the test antibodies completely inhibited all phases of the aggregation process. Results obtained with antibody clone 25 (1B4; IgG2a isotype) are shown in FIG. 19. As the ThT aggregation assay mimics the in vivo biophysical/biochemical stages of AB propagation and aggregation from monomers, oligomers, protofibrils and fibrils that is pivotal in AD pathogenesis, the antibodies raised to cyclo CGHDSGG (SEQ ID NO: 2) demonstrate the potential to completely abrogate this process. Isotype control performed using IgG2a showed no inhibition.

Example 11

Achieving the Optimal Profile for Alzheimer's Immunotherapy: Rational Generation of Antibodies Specific for Toxic A-Beta Oligomers Objective: Generate Antibodies Specific for Toxic Amyloid-β Oligomers (AβO)

Background: Current evidence suggests that propagating prion-like strains of AβO, as opposed to monomers and fibrils, are preferentially toxic to neurons and trigger tau pathology in Alzheimer's disease (AD). In addition, dose-limiting adverse effects have been associated with Aβ fibril recognition in clinical trials. These observations suggest that specific neutralization of toxic AβOs may be desirable for safety and efficacy.

Design/Methods: Computational simulations were employed as described herein, using molecular dynamics with standardized force-fields to perturb atomic-level structures of Aβ fibrils deposited in the Protein Data Base. It was hypothesized that weakly-stable regions are likely to be exposed in nascent protofibrils or oligomers. Clustering analysis, curvature, exposure to solvent, solubility, dihedral angle distribution, and Ramachandran angle distributions were all used to characterize the conformational properties of predicted epitopes, which quantify differences in the antigenic profile when presented in the context of the oligomer vs the monomer or fibril. The candidate peptide epitopes were synthesized in a cyclic format that may mimic regional AβO conformation, conjugated to a carrier protein, and used to generate monoclonal antibodies in mice. Purified antibodies were screened by SPR and immunohistochemistry.

Results

Sixty-six IgG clones against 5 predicted epitopes were selected for purification based on their ability to recognize the cognate structured peptide and synthetic AβO, with little or no binding to unstructured peptide, linker peptide, or Aβ monomers. Additional screening identified antibodies that preferentially bound to native soluble AβO in CSF and brain extracts of AD patients compared to controls. Immunohistochemical analysis of AD brain allowed for selection of antibody clones that do not react with plaque.

Conclusion: Computationally identified AβO epitopes allowed for the generation of antibodies with the desired target profile of selective binding to native AD AβOs with no significant cross-reactivity to monomers or fibrils.

Example 12

Toxicity Inhibition Assay

The inhibition of toxicity of A-beta42 oligomers by antibodies raised to the cyclopeptide can be tested in a rat primary cortical neuron assay.

Antibody and control IgG are each adjusted to a concentration such as 2 mg/mL. Various molar ratios of A-beta oligomer and antibody are tested along with a vehicle control, A-beta oligomer alone and a positive control such as the neuroprotective peptide humanin (HNG).

An exemplary set up is shown in Table 9.

Following preincubation for 10 minutes at room temperature, the volume is adjusted to 840 microlitres with culture medium. The solution is incubated for 5 min at 37 C. The solution is then added directly to the primary cortical neurons and cells are incubated for 24 h. Cell viability can be determined using the MTT assay.

TABLE 9

| AβO / AB molar ratio | AβO (µL) | AβO (µM) | AB (µM) | AB (µL) | Medium (µL) | Final volume (µL) |
|---|---|---|---|---|---|---|
| 5/1 | 1.68 | 4.2 | 0.84 | 12.73 | 185.6 | 200 |
| 1/1 | 1.68 | 4.2 | 4.20 | 63.64 | 134.7 | 200 |
| 1/2 | 1.68 | 4.2 | 8.4 | 127.27 | 71.1 | 200 |

AβO working solution: 2.2 mg/mL-500 µM
CTRL vehicle: 1.68 µL of oligomer buffer + 127.3 µL PBS + 711 µL culture medium
CTRL AβO: 1.68 µL of AβO + 127.3 µL PBS + 711 µL culture medium
CTRL HNG: 1.68 µL of AβO + 8.4 µL HNG (100 nM final) + 127.3 µL PBS + 702.6 µL culture medium This test was conducted using other antibodies raised against other cyclopeptides comprising other epitopes predicted by the collective coordinates method described in Example 1. Inhibition of A-beta oligomer toxicity was observed for these other epitopes. Antibodies raised against cyclo(CGHDSGG) (SEQ ID NO: 2) will be tested.

Example 13

In Vivo Toxicity Inhibition Assay

The inhibition of toxicity of A-beta42 oligomers by antibodies raised to the cyclopeptide can be tested in vivo in mouse behavioral assays.

The antibody and an isotype control are each pre-mixed with A-beta42 oligomers at 2 or more different molar ratios prior to intracerebroventricular (ICV) injection into mice. Control groups include mice injected with vehicle alone, oligomers alone, antibody alone, and a positive control such as the neuroprotective peptide humanin. Alternatively, the antibodies can be administered systemically prior to, during, and/or after ICV injection of the oligomers. Starting approximately 4-7 days post ICV injection of oligomers, cognition is assessed in behavioral assays of learning and memory such as the mouse spatial recognition test (SRT), Y-Maze assay, Morris water maze model and novel object recognition model (NOR).

The mouse spatial recognition test (SRT) assesses topographical memory, a measure of hippocampal function (SynAging). The model uses a two-chamber apparatus, in which the chambers differ in shape, pattern and color (i.e. topographical difference). The chambers are connected by a clear Plexiglass corridor. Individual mice are first placed in the apparatus for a 5 min exploration phase where access to only one of the chambers is allowed. Mice are then returned to their home cage for 30 min and are placed back in the apparatus for a 5 min "choice" phase during which they have access to both chambers. Mice with normal cognitive function remember the previously explored chamber and spend more time in the novel chamber. A discrimination index (DI) is calculated as follows: DI=(TN−TF)/(TN+TF), in which TN is the amount of time spent in the novel chamber and TF is the amount of time spent in the familiar chamber. Toxic A-beta oligomers cause a decrease in DI which can be partially rescued by the humanin positive control. Performance of this assay at different time points post ICV injection can be used to evaluate the potential of antibodies raised to the cyclopeptide to inhibit A-beta oligomer toxicity in vivo.

The Y-maze assay (SynAging) is a test of spatial working memory which is mainly mediated by the prefrontal cortex (working memory) and the hippocampus (spatial component). Mice are placed in a Y-shaped maze where they can explore 2 arms. Mice with intact short-term memory will alternate between the 2 arms in successive trials. Mice injected ICV with toxic A-beta oligomers are cognitively impaired and show random behavior with alternation close to a random value of 50% (versus ~70% in normal animals). This impairment is partially or completely reversed by the cholinesterase inhibitor donepezil (Aricept) or humanin, respectively. This assay provides another in vivo assessment of the protective activity of test antibodies against A-beta oligomer toxicity.

The Morris water maze is another widely accepted cognition model, investigating spatial learning and long-term topographical memory, largely dependent on hippocampal function (SynAging). Mice are trained to find a platform hidden under an opaque water surface in multiple trials. Their learning performance in recalling the platform location is based on visual clues and video recorded. Their learning speed, which is the steadily reduced time from their release into the water until finding the platform, is measured over multiple days. Cognitively normal mice require less and less time to find the platform on successive days (learning). For analyzing long-term memory, the test is repeated multiple days after training: the platform is taken away and the number of crossings over the former platform location, or the time of the first crossing, are used as measures to evaluate long-term memory. Mice injected ICV with toxic A-beta oligomers show deficits in both learning and long-term memory and provide a model for evaluating the protective activity of test antibodies.

The Novel Object Recognition (NOR) model utilizes the normal behavior of rodents to investigate novel objects for a significantly longer time than known objects, largely dependent on perirhinal cortex function (SynAging). Mice or rats are allowed to explore two identical objects in the acquisition trial. Following a short inter-trial interval, one of the objects is replaced by a novel object. The animals are returned to the arena and the time spent actively exploring each object is recorded. Normal rodents recall the familiar object and will spend significantly more time exploring the novel object. In contrast, A-beta oligomer-treated rodents exhibit clear cognitive impairment and will spend a similar amount of time investigating both the 'familiar' and 'novel' object. This can be transiently reversed with known clinical cognitive enhancers (e.g. donepezil). The NOR assay can be performed multiple times in longitudinal studies to assess the potential cognitive benefit of test antibodies.

In addition to behavioral assays, brain tissue can be collected and analyzed for levels of synaptic markers (PSD95, SNAP25, synaptophysin) and inflammation markers (IL-1-beta). Mice are sacrificed at ~14 days post-ICV injection of oligomers and perfused with saline. Hippocampi are collected, snap frozen and stored at −80° C. until analyzed. Protein concentrations of homogenized samples are determined by BCA. Concentration of synaptic markers are determined using ELISA kits (Cloud-Clone Corp, USA). Typically, synaptic markers are reduced by 25-30% in mice injected with A-beta oligomers and restored to 90-100% by the humanin positive control. Concentrations of the IL-1-beta inflammatory markers are increased approximately 3-fold in mice injected with A-beta oligomers and this increase is largely prevented by humanin. These assays provide another measure of the protective activity of test antibodies at the molecular level.

Example 14

In Vivo Propagation Inhibition Assay

In vivo propagation of A-Beta toxic oligomers and associated pathology can be studied in various rodent models of Alzheimer's disease (AD). For example, mice transgenic for human APP (e.g. APP23 mice) or human APP and PSEN1 (APPPS1 mice) express elevated levels of A-beta and exhibit gradual amyloid deposition with age accompanied by inflammation and neuronal damage. Intracerebral inoculation of oligomer-containing brain extracts can significantly accelerate this process (13, 14). These models provide a system to study inhibition of A-beta oligomer propagation by test antibodies administered intracerebrally or systemically.

Example 15

CDR Sequencing

Clone 25 (303-25) which was determined to have an IgG2A heavy chain and a kappa light chain was selected for CDR and variable regions of the heavy and light chains.

RT-PCR was carried out using 5' RACE and gene specific reverse primers which amplify the appropriate mouse immunoglobulin heavy chain (IgG1/IgG3/IgG2A) and light chain (kappa) variable region sequences.

The specific bands were excised and cloned into pCR-Blunt II-TOPO vector for sequencing, and the constructs were transformed into *E. coli*

At least 8 colonies of each chain were picked & PCR screened for the presence of amplified regions prior to sequencing. Selected PCR positive clones were sequenced.

The CDR sequences are in Table 10. The consensus DNA sequence and protein sequences of the variable portion of the heavy and light chain are provided in Table 11

TABLE 10

| Chain | CDR | Sequence | SEQ ID NO |
|---|---|---|---|
| Heavy | CDR-H1 | GYTFTSYW | 17 |
|  | CDR-H2 | IDPSDSQT | 18 |
|  | CDR-H3 | SRGGY | 19 |
| Light | CDR-L1 | QDINNY | 20 |
|  | CDR-L2 | YTS | 21 |
|  | CDR-L3 | LQYDNLWT | 22 |

TABLE 11

Consensus DNA sequence and translated protein sequences of the variable region. The complementarity determining regions (CDRs) are underlined according to IMTG/LIGM-DB.

| Isotype | Consensus DNA Sequence | Protein sequence |
|---|---|---|
| IgG2a<br>SEQ ID<br>NO: 23, 24 | ATGGGATGGAGCTGTATCATCCTCTTCTTGGTAGCAACAGCTACA<br>GGTGTCCACTCCCAGGTCCAACTGCAGCAGCCTGGGGCTGAGCTG<br>GTGAGGCCTGGGGCTTCAGTGAAGCTGTCCTGCAAGGCTTCGGC<br>TACACCTTCACCAGCTACTGGATGAACTGGGTGAAGCAGAGGCCT<br>GGACAAGGCCTTGAATGGATTGGTATGATTGATCCTTCAGACAGT<br>CAAACTCACTACAATCAAATGTTCAAGGACAAGGCCACATTGACT<br>GTAGACAAATCCTCCAGCACAGCCTACCTGCAGCTCAGCAGCCTG<br>ACATCTGAGGACTCTGCCGGTCTATTACTGTTCAAGAGGGGCTAC<br>TGGGGCCAAGGCACCACTCTCACAGTCTCCTCA | MGWSCIILFLVATATG<br>VHSQVQLQQDGAELVR<br>DGASVKLSCKASGYTF<br>TSYWMNWVKQRDGQGL<br>EWIGMIDPSDSQTHYN<br>QMFKDKATLTVDKSSS<br>TAYLQLSSLTSEDSAV<br>YYCSRGGYWGQGTTLT<br>VSS |
| Kappa<br>SEQ ID<br>NO: 25, 26 | ATGAGACCGTCTATTCAGTTCCTGGGGCTCTTGTTGTTCTGGCTT<br>CATGGTGCTCAGTGTGACATCCAGATGACACAGTCTCCATCCTCA<br>CTGTCTGCATCTCTGGGAGGCAAAGTCACCATCACTTGCAAGGCA<br>AGCAAGACATTAACAACTATATAGCTTGGTACCAACACAAGCCT<br>GGAAAAGGTCCTAGGCAGCTCATATATTACACATCTACATTGCAG<br>CCAGGCATCCCATCAAGGTTCAGTGGAAGTGGGTCTGGGAGGAT<br>TATTCCTTCACCATCAGCGACCTGGAGCCTGAAGATATTGCAACT<br>TATTATTGTCTACAGTATGATAATCTGTGGACGTTCGGTGGAGGC<br>ACCAAGCTGGAAATCAAA | MRDSIQFLGLLLFWLH<br>GAQCDIQMTQSPSSLS<br>ASLGGKVTITCKASQD<br>INNYIAWYQHKDGKGD<br>RQLIYYTSTLQDGIDS<br>RFSGSGSGRDYSFTIS<br>DLEDEDIATYYCLQYD<br>NLWTFGGGTKLEIK |

TABLE 12

A-beta "Epitope" Sequences and select A-beta sequences with linker

HDSG (SEQ ID NO: 1)

CGHDSGG, cyclo(CGHDSGG) (SEQ ID NO: 2)

HDSGY (SEQ ID NO: 4)

RHDSG (SEQ ID NO: 5)

RHDS (SEQ ID NO: 6)

GHDSG (SEQ ID NO: 7)

GHDSGG (SEQ ID NO: 8)

TABLE 12-continued

A-beta "Epitope" Sequences and select A-beta sequences with linker

GGHDSGG (SEQ ID NO: 9)

GHDSGGG (SEQ ID NO: 10)

HDSGYE (SEQ ID NO: 11)

CGHDSGGC (SEQ ID NO: 12)

RHDSGY (SEQ ID NO: 13)

DSGY (SEQ ID NO: 14)

DSGYEV (SEQ ID NO: 15)

FRHDSG (SEQ ID NO: 16)

Cyclo(CGHDSG-PEG2); CGHDSG-PEG2(SEQ ID NO: 27)

Cyclo(C-PEG2-HDSGG); C-PEG2-HDSGG (SEQ ID NO: 28)

TABLE 13

DAEFRHDSGYEVHHQKLVFFAEDVGSNKGAIIGLMVGGVVIA (SEQ ID NO: 3)

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Specifically, the sequences associated with each accession numbers provided herein including for example accession numbers and/or biomarker sequences (e.g. protein and/or nucleic acid) provided in the Tables or elsewhere, are incorporated by reference in its entirely.

The scope of the claims should not be limited by the preferred embodiments and examples, but should be given the broadest interpretation consistent with the description as a whole.

CITATIONS FOR REFERENCES REFERRED TO IN THE SPECIFICATION

[1] Gabriela A. N. Crespi, Stefan J. Hermans, Michael W. Parker, and Luke A. Miles. Molecular basis for mid-region amyloid-b capture by leading Alzheimer's disease immunotherapies *SCIENTIFIC REPORTS*|5: 9649, 2015|DOI: 10.1038/srep09649

[2] Vincent J. Hilser and Ernesto Freire. Structure-based calculation of the equilibrium folding pathway of proteins. correlation with hydrogen exchange protection factors. *J. Mol. Biol.*, 262:756-772, 1996. The COREX approach.

[3] Samuel I. A. Cohen, Sara Linse, Leila M. Luheshi, Erik Hellstrand, Duncan A. White, Luke Rajah, Daniel E. Otzen, Michele Vendruscolo, Christopher M. Dobson, and Tuomas P. J. Knowles. Proliferation of amyloid-β42 aggregates occurs through a secondary nucleation mechanism. Proc. Natl.l Acad. Sci. USA, 110(24):9758-9763, 2013.

[4] Pietro Sormanni, Francesco A. Aprile, and Michele Vendruscolo. The camsol method of rational design of protein mutants with enhanced solubility. Journal of Molecular Biology, 427(2):478-490, 2015.

[5] Deborah Blacker, M D, ScD; Marilyn S. Albert, PhD; Susan S. Bassett, PhD; Rodney C. P. Go, PhD; Lindy E. Harrell, M D, PhD; Marshai F. Folstein, M D Reliability and Validity of NINCDS-ADRDA Criteria for Alzheimer's Disease The National Institute of Mental Health Genetics Initiative. *Arch Neurol.* 1994; 51(12):1198-1204. doi:10.1001/archneur.1994.00540240042014.

[6] Hamley, I. W. PEG-Peptide Conjugates 2014; 15, 1543-1559; dx.doi.org/10.1021/bm500246w

[7] Roberts, M J et al Chemistry for peptide and protein PEGylation 64: 116-127.

[8] J. X. Lu, W. Qiang, W. M. Yau, C. D. Schwieters, S. C. Meredith, R. Tycko, MOLECULAR STRUCTURE OF BETA-AMYLOID FIBRILS IN ALZHEIMER'S DISEASE BRAIN TISSUE. CELL Vol. 154 p. 1257 (2013)

[9] Y. Xiao, B. MA, D. McElheny, S. Parthasarathy, F. Long, M. Hoshi, R. Nussinov, Y. Ishii, A BETA (1-42) FIBRIL STRUCTURE ILLUMINATES SELF-RECOGNITION AND REPLICATION OF AMYLOID IN ALZHEIMER'S DISEASE. NAT. STRUCT. MOL. BIOL. Vol. 22 p. 499 (2015).

[10] A. Petkova, W. Yau, R. Tycko EXPERIMENTAL CONSTRAINTS ON QUATERNARY STRUCTURE IN ALZHEIMER'S BETA-AMYLOID FIBRILS BIOCHEMISTRY V. 45 498 2006.

[11] Yu Y Z, Wang W B, Chao A, Chang Q, Liu S, Zhao M, et al. Strikingly reduced amyloid burden and improved behavioral performance in Alzheimer's disease mice immunized with recombinant chimeric vaccines by hexavalent foldable A_1-15 fused to toxin-derived carrier proteins. J Alzheimers Dis 2014; 41:243-60.

[12] Wang, H C; Yu, Y Z; Liu, S; Zhao, M and Q Xu, Peripherally administered sera antibodies recognizing amyloid-beta oligomers mitigate Alzheimer's disease-like pathology and cognitive decline in aged 3×Tg-AD mice, Vaccine 2016.

[13] Franziska Langer, Yvonne S Eisele, Sarah K Fritschi, Matthias Staufenbiel, Lary C Walker, Mathias Jucker (2011) Soluble A{beta} Seeds Are Potent Inducers of Cerebral {beta}-Amyloid Deposition. J Neurosci 31: 41. 14488-14495 October.

[14] Sarah K Fritschi, Franziska Langer, Stephan A Kaeser, Luis F Maia, Erik Portelius, Dorothea Pinotsi, Clemens F Kaminski, David T Winkler, Walter Maetzler, Kathy Keyvani, Philipp Spitzer, Jens Wiltfang, Gabriele S Kaminski Schierle, Henrik Zetterberg, Matthias Staufenbiel, Mathias Jucker (2014) Highly potent soluble amyloid-β seeds in human Alzheimer brain but not cerebrospinal fluid. Brain: a journal of neurology 137: Pt 11. 2909-2915 November

The invention claimed is:

1. A cyclic compound comprising: an amyloid beta (A-beta) peptide the peptide consisting of HDSG (SEQ ID NO: 1), and a linker, wherein the linker is covalently coupled to the A-beta peptide N-terminus residue and the A-beta C-terminus residue, wherein the linker comprises 3, 4 or 5 amino acids.

2. The cyclic compound of claim 1, wherein the linker comprises amino acids GCG or CGC.

3. The cyclic compound of claim 1, wherein the linker comprises amino acids GCG.

4. The cyclic compound of claim 1, wherein the compound further comprises a detectable label.

5. An immunogen comprising the cyclic compound of claim 1.

6. The immunogen of claim 5, wherein the compound is coupled to a carrier protein or immunogenicity enhancing agent.

7. The immunogen of claim 6, wherein the carrier protein is bovine serum albumin (BSA), or the immunogenicity-enhancing agent is Keyhole Limpet Haemocyanin (KLH).

8. A composition comprising the compound of claim 1 or an immunogen comprising said compound.

9. The composition of claim 8, further comprising an adjuvant.

10. The composition of claim 9, wherein the adjuvant comprises aluminum phosphate, aluminum hydroxide, CpG oligonucleotides, or polyphosphazene.

11. A kit comprising: (a) a compound comprising: an A-beta peptide, the peptide consisting of HDSG (SEQ ID NO: 1), and a linker, wherein the linker is covalently coupled to the A-beta peptide N-terminus residue and the A-beta C-terminus residue; or (b) an immunogen comprising said compound.

12. A method of making an antibody that specifically binds to the A-beta peptide in the compound of claim 1, comprising administering the compound; an immunogen comprising said compound or a composition comprising said compound or said immunogen to a subject and isolating antibody and/or cells expressing antibody specific or selective for the compound or immunogen administered and/or A-beta oligomers.

13. A method of inducing an immune response in a subject, comprising administering to the subject the compound or a combination of compounds of claim 1.

14. The method of claim 13, comprising isolating cells and/or antibodies that specifically or selectively bind the A-beta peptide in the compound or immunogen administered.

15. A method of treating Alzheimer's Disease (AD) and/or other A-beta amyloid related diseases, the method comprising administering to a subject in need thereof the cyclic compound of claim 1, or an immunogen or pharmaceutical composition comprising said cyclic compound, to a subject in need thereof.

16. The method of claim 15, wherein more than one immunogen is administered.

* * * * *